(12) United States Patent
Nozaki et al.

(10) Patent No.: US 9,580,696 B2
(45) Date of Patent: Feb. 28, 2017

(54) METHOD FOR PRODUCING γ-GLUTAMYLVALYLGLYCINE OR A SALT THEREOF

(71) Applicant: Ajinomoto Co., Inc., Chuo-ku (JP)

(72) Inventors: Hiroyuki Nozaki, Kawasaki (JP); Isao Abe, Kawasaki (JP); Jun Takakura, Kawasaki (JP); Rie Takeshita, Kawasaki (JP); Hideyuki Suzuki, Kyoto (JP); Shunichi Suzuki, Kawasaki (JP)

(73) Assignee: Ajinomoto Co., Inc., Chuo-ku (JP)

( * ) Notice: Subject to any disclaimer, the term of this patent is extended or adjusted under 35 U.S.C. 154(b) by 259 days.

(21) Appl. No.: 14/243,458

(22) Filed: Apr. 2, 2014

(65) Prior Publication Data

US 2014/0212920 A1    Jul. 31, 2014

Related U.S. Application Data

(63) Continuation of application No. PCT/JP2012/075908, filed on Oct. 5, 2012.

(30) Foreign Application Priority Data

Oct. 7, 2011 (JP) ................................. 2011-223058

(51) Int. Cl.

| | |
|---|---|
| *C12P 21/02* | (2006.01) |
| *C12N 9/10* | (2006.01) |
| *C07K 5/093* | (2006.01) |
| *C07K 5/02* | (2006.01) |

(52) U.S. Cl.

CPC ............ *C12N 9/104* (2013.01); *C07K 5/0819* (2013.01); *C12P 21/02* (2013.01); *C07K 5/0215* (2013.01); *Y02P 20/52* (2015.11)

(58) Field of Classification Search

CPC .... C07K 5/0215; C07K 5/0819; C12N 9/104; C12P 21/02; Y02P 20/52

See application file for complete search history.

(56) References Cited

U.S. PATENT DOCUMENTS

| | | |
|---|---|---|
| 7,288,389 B2 | 10/2007 | Hara et al. |
| 7,531,340 B2 | 5/2009 | Hara et al. |
| 7,736,871 B2 | 6/2010 | Hara et al. |
| 7,736,876 B2 | 6/2010 | Hara et al. |
| 8,039,232 B2 | 10/2011 | Hara et al. |
| 8,329,428 B2 | 12/2012 | Hara et al. |
| 8,389,241 B2 | 3/2013 | Hara et al. |
| 8,399,417 B2 | 3/2013 | Nagasaki et al. |
| 2005/0019864 A1 | 1/2005 | Hara et al. |
| 2008/0050773 A1 | 2/2008 | Hara et al. |
| 2008/0166761 A1 | 7/2008 | Hara et al. |
| 2008/0274530 A1 | 11/2008 | Hara et al. |
| 2010/0105864 A1 | 4/2010 | Yoneda et al. |
| 2010/0120698 A1 | 5/2010 | Nagasaki et al. |
| 2010/0183792 A1 | 7/2010 | Nagasaki et al. |
| 2010/0267082 A1 | 10/2010 | Hara et al. |
| 2011/0046046 A1 | 2/2011 | Hara et al. |
| 2011/0071075 A1 | 3/2011 | Takeuchi et al. |
| 2012/0003693 A1 | 1/2012 | Hara et al. |
| 2013/0011873 A1 | 1/2013 | Hara et al. |
| 2013/0122544 A1 | 5/2013 | Hara et al. |

FOREIGN PATENT DOCUMENTS

| | | |
|---|---|---|
| EP | 2 156 752 A1 | 2/2010 |
| EP | 2 156 846 A1 | 2/2010 |
| EP | 2 269 646 A1 | 1/2011 |
| EP | 2 275 138 A1 | 1/2011 |
| JP | 02-231085 A | 9/1990 |
| JP | 08-119916 A | 5/1996 |
| WO | WO 2004/011653 A1 | 2/2004 |
| WO | 2005/075652 | 8/2005 |
| WO | WO 2007/055388 A2 | 5/2007 |
| WO | WO 2007/055393 A1 | 5/2007 |
| WO | WO 2008/139945 A1 | 11/2008 |
| WO | WO 2008/139946 A1 | 11/2008 |
| WO | WO 2008/139947 A1 | 11/2008 |
| WO | WO 2009/107660 A1 | 9/2009 |
| WO | WO 2009/119554 A1 | 10/2009 |
| WO | 2013/051685 | 4/2013 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Hideyuki Suzuki et al., "Transformation of γ-glutamyltranspeptidase to glutaryl-7-aminocephalosporanic acid acylase: utilization of the three-dimensional structure to introduce an effective modification", Bioscience & Industry, 2008, vol. 66, No. 12, pp. 660-666.
Chiaki Yamada et al., "Improvement of the Glutaryl-7-Aminocephalosporanic Acid Acylase Activity of a Bacterial γ-Glutamyltranspeptidase", Applied and Environmental Microbiology, Jun. 2008, vol. 74, No. 11, pp. 3400-3409.
Hideyuki Suzuki et al., "γ-Glutamyltranspeptidase: A new member of Ntn-hydrolase superfamily", Protein, Nucleic Acid and Enzyme, 2001, vol. 46, No. 12, pp. 1842-1848.
Hideyuki Suzuki et al., "γ-Glutamyl compounds and their enzymatic production using bacterial γ-glutamyltranspeptidase", Amino Acids, 2007, vol. 32, pp. 333-340.

(Continued)

*Primary Examiner* — Delia Ramirez
(74) *Attorney, Agent, or Firm* — Oblon, McClelland, Maier & Neustadt, L.L.P.

(57) ABSTRACT

A method for producing γ-Glu-Val-Gly comprising the step of reacting Val-Gly with a γ-glutamyl group donor in the presence of a γ-glutamyltransferase, a microorganism containing the enzyme, or a processed product thereof to generate γ-Glu-Val-Gly, wherein the γ-glutamyltransferase consists of a large subunit and a small subunit, and the small subunit has a specific mutation.

19 Claims, 2 Drawing Sheets

(56) References Cited

OTHER PUBLICATIONS

Hidehiko Kumagai et al., "Syntheses of γ-Glutamyl Peptides by γ-Glutamyltranspeptidase from *E. coli*", Annals New York Academy of Sciences, 1990, vol. 613, pp. 647-651.

Toshihiro Okada et al., "Crystal Structure of the γ-Glutamyltranspeptidase Precursor Protein from *Escherichia coli* Structural Changes Upon Autocatalytic Processing and Implications for the Maturation Mechanism", The Journal of Biological Chemistry, Jan. 26, 2007, vol. 282, No. 4, pp. 2433-2439.

Toshihiro Okada et al., "Crystal Structures of γ-glutamyltranspeptidase from *Escherichia coli*, a key enzyme in glutathione metabolism, and its reaction intermediate," PNAS, Apr. 25, 2006, vol. 103, No. 17, pp. 6471-6476.

Hideyuki Suzuki et al., "How is the catalytic pocket of the mature γ-glutamyltranspeptidase formed upon autocatalytic processing of its precursor?", Protein Nucleic Acid and Enzyme, 2009, vol. 54, No. 3, pp. 245-251.

International Search Report issued Dec. 18, 2012, in International Application No. PCT/JP2012/075908.

English translation of the International Preliminary Report on Patentability and Written Opinion issued Apr. 17, 2014 in PCT/JP2012/075908.

Hideyuki Suzuki, et al., "Improvement of the Flavor of Amino Acids and Peptides Using Bacterial γ-glutamyltranspeptidase" Recent Highlights in Flavor Chemistry & Biology, 2007, pp. 227-232.

Hideyuki Suzuki, et al., "A Single Amino Acid Substitution Converts γ-Glutamyltranspeptidase to a Class IV Cephalosporin Acylase (Glutaryl-7-Aminocephalosporanic Acid Acylase)", Applied and Environmental Microbiology, vol. 70, No. 10, Oct. 2004, pp. 6324-6328.

Amy L. Morrow, et al., "Characterization of *Helicobacter pylori* γ-Glutamyltranspeptidase Reveals the Molecular Basis for Substrate Specificity and a Critical Role for the Tyrosine 433-Containing Loop in Catalysis", Biochemistry, vol. 46, 2007, pp. 13407-13414.

Ping-Lin Ong, et al., "Residues Arg114 and Arg337 are critical for the proper function of *Escherichia coli* γ-glutamyltranspeptidase", Biochemical and Biophysical Research Communications, vol. 366, 2008, pp. 294-300.

Huei-Fen Lo, et al., "Site-directed mutagenesis of conserved Thr407, Asp433 and Met464 residues in small subunit of *Escherichia coli* γ-glutamyltranspeptidase", Indian Journal of Biochemistry & Biophysics, vol. 44, Aug. 2007, pp. 197-203.

Wataru Hashimoto, et al., "Effect of Site-Directed Mutations on Processing and Activity of γ-Glutamyltranspeptidase of *Escherichia coli* K-12", J. Biochem., vol. 118, No. 1, 1995, pp. 75-80.

Wataru Hashimoto, et al., "*Escherichia coli* γ-Glutamyltranspeptidse Mutants Deficient In Processing to Subunits", Biochemical and Biophysical Research Communications, vol. 189, No. 1, Nov. 30, 1992, pp. 173-178.

Yong-Qiang Gu, et al., "Specificity of the wound-induced leucine aminopeptidase (LAP-A) of tomato", Eur. J. Biochem., vol. 267, 2000, pp. 1178-1187.

Charles G. Miller, et al., "Peptidase-Deficient Mutants of *Escherichia coli*" Journal of Bacteriology, vol. 135, No. 2, Aug. 1978, pp. 603-611.

Extended European Search Report issued on Mar. 6, 2015 in Application No. 12838509.3.

Hideyuki Suzuki, et al., "Enzymatic synthesis of gamma-glutamylvaline to improve the bitter taste of valine", Journal of Agricultural and Food Chemistry, vol. 52, No. 3, XP002735891, Feb. 11, 2004, pp. 577-580.

European Communication Pursuant to Article 94(3) EPC issued Apr. 7, 2016 in Patent Application No. 12 838 509.3.

Minami Hiromichi, et al., "A mutant Bacillus Subtilis y-Glutamyltranspeptidase Specialized in Hydrolysis Activity" FEMS Microbiology Letters, vol. 224, No. 2, Jul. 29, 2003, pp. 169-173.

* cited by examiner

Fig. 1

```
consensus       1:TTHXSVVDKDGNAVAVTYTLNTTFGTGIVAGXXGILLNNXMDDFSAKPGV  50
E. coli         1:TTHYSVVDKDGNAVAVTYTLNTTFGTGIVAGESGILLNNQMDDFSAKPGV  50
Sh. flexneri 5 str. 8401        1:TTHYSVVDKDGNAVAVTYTLNTTFGTGIVAGESGILLNNQMDDFSAKPGV  50
Sh. dysenteriae Sd197           1:TTHYSVVDKDGNAVAVTYTLNTTFGTGIVAGESGILLNNQMDDFSAKPGV  50
Sh. boydii Sb227                1:TTHYSVVDKDGNAVAVTYTLNTTFGTGIVAGESGILLNNQMDDFSAKPGV  50
S. typhimurium ATCC700720       1:TTHFSVVDKDGNAVAVTYTLNTTFGTGIVAGNTGILLNNQMDDFSAKPGV  50
S. enterica SC-B67              1:TTHFSVVDKDGNAVAVTYTLNTTFGTGIVAGNTGILLNNQMDDFSAKPGV  50
S. typhi Ty2                    1:TTHFSVVDKDGNAVAVTYTLNTTFGTGIVAGNTGILLNNEMDDFSAKPGV  50
K. pneumoniae ATCC202080        1:TTHFSVVDKDGNAVAVTYTLNTTFGTGIVAGDSGILLNNQMDDFSAKPGV  50
S. enterica ATCC 9150           1:TTHFSVVDKDGNAVAVTYTLNTTFGTGIVAGNTGILLNNQMDDFSAKPGV  50
K. pneumoniae KPN308894         1:TTHFSVVDKDGNAVAVTYTLNTTFGTGIVAGNSGILLNNQMDDFSAKPGV  50
En. cloaceae EBC103795          1:TTHFSVVDKDGNAVAVTYTLNTTFGTGIVAGNSGILLNNEMDDFSAKPGV  50
                                  *.************************. ********** consensus       51:PNVYGLVGGDANAVXPXKRPLSSMSPTIVVXGKTWLVTGSPGGSRIITT 100
E. coli         51:PNVYGLVGGDANAVGPNKRPLSSMSPTIVVKDGKTWLVTGSPGGSRIITT 100
Sh. flexneri 5 str. 8401        51:PNVYGLVGGDANAVGPNKRPLSSMSPTIVVKDGKTWLVTGSPGGSRIITT 100
Sh. dysenteriae Sd197           51:PNVYGLVGGDANAVGPNKRPLSSMSPTIVVKDGKTWLVTGSPGGSRIITT 100
Sh. boydii Sb227                51:PNVYGLVGGDANAVGPNKRPLSSMSPTIVVKDGKTWLVTGSPGGSRIITT 100
S. typhimurium ATCC700720       51:PNVYGLVGGDANAVGPKKRPLSSMSPTIVVKEGKTWLVTGSPGGSRIITT 100
S. enterica SC-B67              51:PNVYGLVGGDANAVGPKKRPLSSMSPTIVVKEGKTWLVTGSPGGSRIITT 100
S. typhi Ty2                    51:PNVYGLVGGDANAVEPKKRPLSSMSPTIVVKDGKTWLVTGSPGGSRIITT 100
K. pneumoniae ATCC202080        51:PNVYGLVGGDANAVEPKKRPLSSMSPTIVVKDGKTWLVTGSPGGSRIITT 100
S. enterica ATCC 9150           51:PNVYGLVGGDANAVGPKKRPLSSMSPTIVVKDGKTWLVTGSPGGSRIITT 100
K. pneumoniae KPN308894         51:PNVYGLVGGDANAVGPKKRPLSSMSPTIVVKDGKTWLVTGSPGGSRIITT 100
En. cloaceae EBC103795          51:PNVYGLVGGDANAVGPKKRPLSSMSPTIVVKDGKTWLVTGSPGGSRIITT 100
                                   **************. *. *. **********.***************
```

Fig. 2

| | | |
|---|---|---|
| consensus | | |
| E. coli | 101 | VLQMVVNXIDXGXNVAEATNAPRFHHQWLPDELRVEKGFSPDTXKLLEXX : 150 |
| Sh. flexneri 5 str. 8401 | 101 | VLQMVVNSIDYGLNVAEATNAPRFHHQWLPDELRVEKGFSPDTLKLLEAK : 150 |
| Sh. dysenteriae Sd197 | 101 | VLQMVVNSIDYGMNVAEATNAPRFHHQWLPDELRVEKGFSPDTLKLLEAK : 150 |
| Sh. boydii Sb227 | 101 | VLQMVVNSIDYGMNVAEATNAPRFHHQWLPDELRVEKGFSPDTLKLLEAK : 150 |
| S. typhimurium ATCC700720 | 101 | VLQMVVNSIDFGMNVAEATNAPRFHHQWLPDELRVEKGFSPDTLKLLEGK : 150 |
| S. enterica SC-B67 | 101 | VLQMVVNSIDFGMNVAEATNAPRFHHQWLPDELRVEKGFSPDTLKLLEGK : 150 |
| S. typhi Ty2 | 101 | VLQMVVNSIDFGMNVAEATNAPRFHHQWLPDELRVEKGFSPDTLKLLEAK : 150 |
| K. pneumoniae ATCC202080 | 101 | VLQMVVNTIDFGMNVAEATNAPRFHHQWLPDELRVEKGFSPDTLKLLEAK : 150 |
| S. enterica ATCC 9150 | 101 | VLQMVVNSIDFGMNVAEATNAPRFHHQWLPDELRVEKGFSPDTIKLLEGK : 150 |
| K. pneumoniae KPN308894 | 101 | VLQMVVNTIDFGMNVAEATNAPRFHHQWLPDELRVEKGFSPDTLKLLEAK : 150 |
| En. cloaceae EBC103795 | 101 | VLQMVVNSIDFGMNVAEATNAPRFHHQWLPDELRVEKGFSPDTIKLLEQR : 150 |
| | | ****..*..**********************.*** . |

| | | |
|---|---|---|
| consensus | | |
| E. coli | 151 | GQKVAXKEAMGSTQSIMVGPDGXLXGASDPRSXDDLXAGY : 190 |
| Sh. flexneri 5 str. 8401 | 151 | GQKVALKEAMGSTQSIMVGPDGELYGASDPRSVDDLTAGY : 190 |
| Sh. dysenteriae Sd197 | 151 | GQKVALKEAMGSTQSIMVGPDGELYGASDPRSVDDLTAGY : 190 |
| Sh. boydii Sb227 | 151 | GQKVALKEAMGSTQSIMVGPDGELYGASDPRSVDDLTAGY : 190 |
| S. typhimurium ATCC700720 | 151 | GQKVALKEAMGSTQSIMVGPDGELYGASDPRSVDDLTAGY : 190 |
| S. enterica SC-B67 | 151 | GQKVALKEAMGSTQSIMVGPDGELYGASDPRSVDDLTAGY : 190 |
| S. typhi Ty2 | 151 | GQKVALKEAMGSTQSIMVGPDGELYGASDPRSVDDLTAGY : 190 |
| K. pneumoniae ATCC202080 | 151 | GQKVALKEAMGSTQSIMVGPDGMLYGASDPRSPDDLTAGY : 190 |
| S. enterica ATCC 9150 | 151 | GQKVALKEAMGSTQSIMVGPDGALYGASDPRSVDDLTAGY : 190 |
| K. pneumoniae KPN308894 | 151 | GQKVALKEAMGSTQSIMVGPDGMLYGASDPRSPDDLTAGY : 190 |
| En. cloaceae EBC103795 | 151 | GQKVAVKEAMGSTQSIMVGPDGALFGASDPRSVDDLSAGY : 190 |
| | | ****.*****************.*.*** |

METHOD FOR PRODUCING γ-GLUTAMYLVALYLGLYCINE OR A SALT THEREOF

CROSS-REFERENCE TO RELATED APPLICATIONS

The present application is a continuation of and claims the benefits of priority to International Application No. PCT/JP2012/075908, filed Oct. 5, 2012, the entire contents of which are incorporated herein by reference. International Application No. PCT/JP2012/075908 claims the benefits of priority to Japanese Patent Application No. 2011-223058, filed Oct. 7, 2011.

TECHNICAL FIELD

The present invention relates to a method for producing γ-glutamylvalylglycine or a salt thereof, and a mutant of γ-glutamyltransferase preferably used for the method. γ-Glutamylvalylglycine is useful in the fields of food, drug, and so forth.

BACKGROUND ART

A certain kind of peptides such as γ-glutamylvalylglycine (L-γ-glutamyl-L-valyl-glycine, henceforth referred to as "γ-Glu-Val-Gly") have a calcium receptor agonistic activity (Patent document 1). Such peptides having a calcium-receptor activation action are known to be able to impart kokumi taste to foods and drinks (Patent document 2), improve tastes of low fat diets, especially fat-like thickness and smoothness (Patent document 3), improve feeling of body of sweet taste substances, and improve bitterness peculiar to sweet taste substances (Patent document 4).

Moreover, such peptides as described above are known to have a prophylactic or curative effect on diarrhea (Patent document 5) and diabetes (Patent document 6), and a bicarbonate secretion promoting effect in the alimentary tract (Patent document 7).

As described above, wide application of γ-Glu-Val-Gly in the field of food, drug, and so forth is expected.

As methods for producing tripeptides, chemical synthesis methods and enzymatic methods are generally known. As one of the chemical synthesis methods, a method of selectively γ-glutamylating a dipeptide by using N-protected glutamic anhydride to obtain a tripeptide is known (Patent document 10). As the enzymatic methods, there is known, for example, a method of reacting a dipeptide having an esterified or amidated carboxyl terminus and an amino acid having free amino group (for example, an amino acid of which carboxyl group is protected) in the presence of a peptide-producing enzyme to produce a tripeptide (Patent document 8).

As an enzyme that catalyzes the reaction of transferring γ-glutamyl group to a dipeptide, γ-glutamyl transferase (also called γ-glutamyl transpeptidase, henceforth also referred to as "GGT") is known. It was reported that in a reaction of Val-Gly (valylglycine) and γ-glutamyl-p-nitroanilide as a glutamine donor in the presence of that enzyme, the activity of the enzyme was detected by color development of p-nitroaniline (Non-patent document 1), but generation of γ-Glu-Val-Gly was not confirmed.

GGT of Escherichia coli consists of two subunits, a large subunit and a small subunit, and the ggt gene coding for GGT comprises ORFs (open reading frames) coding for a leader peptide, the large subunit, and the small subunit (Patent document 9). With advance of the transcription and translation of the ggt gene, transfer of the translation product to the periplasm, cleavage of the leader peptide and processing for generating the large subunit and the small subunit occur to generate the mature GGT.

As for researches concerning the structural analysis of GGT, it was reported that the D433N mutation (Non-patent document 2) or the Y444 mutation and G484 mutation (Non-patent document 3) of Escherichia coli GGT impart a novel acylase activity, specifically an ability to hydrolyze glutaryl-7-aminocephalosporanic acid, to GGT, or improve such an ability. Non-patent document 3 (Yamada et al.) specifically describes N411G, N411H, N411Y, Q430I, Q430V, D433A, D433G, D433L, D433N, Y444A, Y444F, Y444G, Y444H, Y444I, Y444L, Y444V, G484A, P460V, L461F, and S462T mutations.

Further, as information concerning the structure around the active center of GGT, it was reported that Y444 in GGT of Escherichia coli (Non-patent document 3) or Y433 in GGT of Helicobacter Pylori (Non-patent document 4) locates in the lid-loop that covers the substrate-binding site.

Furthermore, it was also reported that Arg114 and Arg337 are important for the function of GGT of Escherichia coli (Non-patent document 5), and this reference describes R114K, R114L, R114D, R337K, R337L, and R337D mutations.

Further, it is also reported that most of mutants of Escherichia coli GGT having mutations at Thr407, Asp433, and Met464 in the small subunit lost the activity (Non-patent document 6). This reference describes N411G, N411H, N411Y, Q430I, Q430V, D433A, D433G, D433L, D433N, Y444A, Y444F, Y444G, Y444H, Y444I, Y444L, Y444V, G484A, P460V, L461F, and S462T mutations.

In addition, influences of T391, T392, H393, Q390 and V396 mutations (Non-patent document 7), and R513 and R571 mutations (Non-patent document 8) on processing into the subunits of Escherichia coli GGT or the GGT activity were reported. The former reference describes T391A, T391S, T392A, H393G, Q390A, and V396T mutations, and the latter reference describes R513A, R513G, R571A, and R571G mutations.

However, any mutation or combination of mutations preferred for the γ-glutamylation of Val-Gly is not known.

For the decomposition of Val-Gly, it was reported that PepA hydrolyzes Val-Gly (Non-patent document 9), and PepA- and PepN-deficient Escherichia coli does not decompose Val-Gly (Non-patent document 10), but activity of pepD for decomposing Val-Gly is not known.

PRIOR ART REFERENCES

Patent Documents

Patent document 1: WO2007/055388
Patent document 2: WO2007/055393
Patent document 3: WO2008/139945
Patent document 4: WO2008/139946
Patent document 5: WO2008/139947
Patent document 6: WO2009/107660
Patent document 7: WO2009/119554
Patent document 8: WO2004/011653
Patent document 9: Japanese Patent Laid-open (Kokai) No. 02-231085
Patent document 10: Japanese Patent Laid-open No. 08-119916

Non-Patent Documents

Non-patent document 1: Suzuki, H. et al. (2008) Improvement of the flavor of amino acids and peptides using bacterial γ-glutamyltranspeptidase, In Recent Highlights in Flavor Chemistry & Biology, Ed. by Hofmann, T. et al., pp. 227-232, Deutsche Forschungsanstalt fur Lebensmittelchemie
Non-patent document 2: Suzuki, H. et al., Applied and Environmental Microbiology, 70 (10), 6324-6328, 2004
Non-patent document 3: Yamada, C. et al., Appl. Environ. Microbiol., 74(11):3400-3409, 2008
Non-patent document 4: Morrow, A. L. et al., Biochemistry., 20; 46(46):13407-13414, 2007
Non-patent document 5: Ong, P. L. et al., Biochem. Biophys. Res. Commun., 366(2):294-300, 2008
Non-patent document 6: Lo, H. F. et al, Indian J. Biochem. Biophys., 44(4):197-203, 2007
Non-patent document 7: Hashimoto, W. et al., J. Biochem., 118(1):75-80, 1995
Non-patent document 8: Hashimoto, W. et al., Biochem. Biophys. Res. Commun., 189(1):173-178, 1992
Non-patent document 9: Gu, Y. Q. et al., Eur. J. Biochem., 267:1178-1187, 2000
Non-patent document 10: Miller, C. G. et al., Journal of Baccteriol., 135(2):603-611, 1978

DISCLOSURE OF THE INVENTION

Object to be Achieved by the Invention

An object of the present invention is to provide a mutant of GGT suitable for the γ-glutamylation of Val-Gly, and a method for producing γ-Glu-Val-Gly or a salt thereof using such a mutant GGT.

Means for Achieving the Object

The inventor of the present invention conducted various researches in order to achieve the aforementioned object, as a result, they found mutations of GGT suitable for the γ-glutamylation of Val-Gly, and accomplished the present invention.

The present invention thus relates to the followings.

(1) A method for producing γ-Glu-Val-Gly comprising the step of reacting Val-Gly with a γ-glutamyl group donor in the presence of a γ-glutamyltransferase, a microorganism containing the enzyme, or a processed product thereof to generate γ-Glu-Val-Gly, wherein:

the γ-glutamyltransferase consists of a large subunit and a small subunit, and the small subunit has the amino acid sequence of the positions 391 to 580 of SEQ ID NO: 2 or the amino acid sequence having a homology of 90% or more to the foregoing amino acid sequence, and has a mutation for one or more residues corresponding to one or more residues selected from the following residues in the amino acid sequence of SEQ ID NO: 2:
N411, T413, Q430, P441, V443, Y444, L446, A453, D472, G484, S498, Q542, D561, S572.

(2) The method as described above, wherein the mutation corresponds to a mutation selected from the following mutations:
N411(Q)
T413(H, N, A)
Q430(M, N)
P441A
V443(E, L, G, N, Q, A)
Y444(D, E, N, A)
L446A
A453S
D472 (I)
G484 (S, A, E)
S498C
Q542H
D561N
S572K.

(3) The method as described above, wherein the mutation is a mutation corresponding to any one of the following mutations:
N411Q, Q430M, Y444A, Y444D, Y444E, G484S, (T413A+Y444E), (T413H+Y444E), (T413N+Y444E), (Q430N+Y444E), (Q430N+Y444D), (Q430N+Y444N), (P441A+Y444E), (V443A+Y444E), (V443E+Y444E), (V443G+Y444E), (V443L+Y444E), (V443N+Y444E), (V443Q+Y444E), (Y444E+L446A), (Y444E+A453S), (Y444E+D472I), (Y444E+G484A), (Y444E+G484S), (Y444E+S498C), (Y444E+Q542H), (Y444E+D561N), (T413N+Y444E+V443A), (T413N+Y444E+A453S), (T413N+Y444E+S498C), (T413N+Y444E+Q542H), (G484S+Y444E+V443A), (G484S+Y444E+Q542H), (Q430N+Y444E+T413N), (T413H+Y444E+G484S), (T413N+Y444E+G484S), (T413N+Y444E+G484S+V443A), (T413N+Y444E+G484S+A453S), (T413N+Y444E+G484S+Q542H), (T413N+Y444E+G484S+S572K) (T413N+Y444E+G484S+Q430N), (T413N+Y444E+G484E+S498C).

(4) The method as described above, wherein the large subunit has the amino acid sequence of the positions 26 to 390 of SEQ ID NO: 2 or the amino acid sequence having a homology of 90% or more to the foregoing amino acid sequence.

(5) The method as described above, wherein the large subunit has a mutation corresponding to any one of the following mutations in the amino acid sequence of SEQ ID NO: 2:
P27H, E38K, L127V, F174A, F174I, F174L, F174M, F174V, F174W, F174Y, T246R, T276N, V301L.

(6) The method as described above, wherein the small subunit has the amino acid sequence of SEQ ID NO: 13 except for the aforementioned mutation.

(7) The method as described above, wherein the small subunit has the amino acid sequence of:
the positions 391 to 580 of SEQ ID NO: 2, the positions 391 to 580 of SEQ ID NO: 3, the positions 392 to 581 of SEQ ID NO: 4, the positions 388 to 577 of SEQ ID NO: 5, the positions 391 to 580 of SEQ ID NO: 6, the positions 391 to 580 of SEQ ID NO: 7, the positions 391 to 580 of SEQ ID NO: 8, the positions 400 to 589 of SEQ ID NO: 9, the positions 391 to 580 of SEQ ID NO: 10, the positions 392 to 581 of SEQ ID NO: 11, or the positions 392 to 581 of SEQ ID NO: 12, or any one of these amino acid sequences including substitutions, deletions, insertions, additions, or inversions of one or several amino acid residues, except for the aforementioned mutation.

(8) The method as described above, wherein the large subunit has the amino acid sequence of:
the positions 26 to 390 of SEQ ID NO: 2, the positions 26 to 390 of SEQ ID NO: 3, the positions 26 to 391 of SEQ ID NO: 4, the positions 26 to 387 of SEQ ID NO: 5, the positions 25 to 390 of SEQ ID NO: 6, the positions 25 to 390 of SEQ ID NO: 7, the positions 25 to 390 of SEQ ID NO: 8, the positions 33 to 399 of SEQ ID NO: 9, the positions 25 to 390 of SEQ ID NO: 10, the positions 25 to 391 of SEQ ID NO: 11, or the positions 25 to 391 of SEQ ID NO: 12, or any one of these amino acid sequences including substitutions, deletions, insertions, additions, or inversions of one or several amino acid residues, except for the aforementioned mutation.

(9) The method as described above, wherein the γ-glutamyl group donor is L-glutamine.

(10) The method as described above, wherein the γ-glutamyltransferase, the microorganism containing the enzyme, or the processed product thereof is a microorganism containing the enzyme, or a processed product thereof, and the microorganism is a bacterium belonging to the family Enterobacteriaceae.

(11) The method as described above, wherein the microorganism is an *Escherichia* bacterium.

(12) The method as described above, wherein the microorganism is *Escherichia coli*.

(13) The method as described above, wherein the microorganism is deficient in peptidase D.

(14) The method as described above, wherein the reaction is performed in the presence of a metal chelating agent.

(15) A mutant γ-glutamyltransferase consisting of the following large subunit and small subunit:

(A) a large subunit which has the amino acid sequence of the positions 26 to 390 of SEQ ID NO: 2 or the amino acid sequence including substitutions, deletions, insertions, additions, or inversions of one or several amino acid residues, and able to form a complex having the γ-glutamyltransferase activity with any one of the following small subunit;

(B) a small subunit which has the amino acid sequence of the positions 391 to 580 of SEQ ID NO: 2 or the amino acid sequence including substitutions, deletions, insertions, additions, or inversions of one or several amino acid residues, has any one of the following mutations, and able to form a complex having the γ-glutamyltransferase activity with the above large subunit:

Y444D, Y444E, (T413A+Y444E), (T413H+Y444E), (T413N+Y444E), (Q430N+Y444E), (Q430N+Y444D), (Q430N+Y444N), (P441A+Y444E), (V443A+Y444E), (V443E+Y444E), (V443G+Y444E), (V443L+Y444E), (V443N+Y444E), (V443Q+Y444E), (Y444E+L446A), (Y444E+A453S), (Y444E+D472I), (Y444E+G484A), (Y444E+G484S), (Y444E+S498C), (Y444E+Q542H), (Y444E+D561N), (T413N+V443A+Y444E), (T413N+Y444E+A453S), (T413N+Y444E+S498C), (T413N+Y444E+Q542H), (G484S+Y444E+V443A), (G484S+Y444E+Q542H), (Q430N+Y444E+T413N), (T413H+Y444E+G484S), (T413N+Y444E+G484S), (T413N+Y444E+G484S+V443A), (T413N+Y444E+G484S+A453S), (T413N+Y444E+G484S+Q542H), (T413N+Y444E+G484S+S572K), (T413N+Y444E+G484S+Q430N), (T413N+Y444E+G484E+S498C).

(16) The mutant γ-glutamyltransferase as described above, wherein the large subunit has any one of the following mutations:
P27H, E38K, L127V, F174A, F174I, F174L, F174M, F174V, F174W, F174Y, T246R, T276N, V301L.

BRIEF DESCRIPTION OF THE DRAWINGS

FIG. 1 shows alignment of the amino acid sequences of the GGT small subunits of various bacteria. The strains of the bacteria are as follows. The numerals described before and after the amino acid sequences represent positions from the N-terminus of the small subunit. Relations of the amino acid sequences and the amino acid sequences described in Sequence Listing are also shown.

Consensus: consensus sequence (SEQ ID NO: 13)
*E. coli*: *Escherichia coli* (SEQ ID NO: 2, 391 to 580)
*Sh. flexneri* 5 str. 8401: *Shigella flexneri* 5 str. 8401 (SEQ ID NO: 3, 391 to 580)
*Sh. dysenteriae* Sd197: *Shigella dysenteriae* Sd197 (SEQ ID NO: 4, 392 to 581)
*Sh. boydii* Sb227: *Shigella boydii* strain Sb227 (SEQ ID NO: 5, 388 to 577)
*S. typhimurium* ATCC700720: *Salmonella enterica typhimurium* strain ATCC 700720 (also designated as *Salmonella typhimurium* LT2, SEQ ID NO: 6, 391 to 580)
*S. enterica* SC-B67: *Salmonella enterica enterica choleraesuis* strain SC-B67 (SEQ ID NO: 7, 391 to 580)
*S. typhi* Ty2: *Salmonella enterica typhi* strain Ty2 (SEQ ID NO: 8, 391 to 580)
*K. pneumoniae* ATCC202080: *Klebsiella pneumoniae* strain ATCC 202080 (SEQ ID NO: 9, 400 to 589)
*S. enterica* ATCC 9150: *Salmonella enterica* subsp. *enterica* serovar *Paratyphi* A str. ATCC 9150 (SEQ ID NO: 10, 391 to 580)
*K. pneumoniae* KPN308894: *Klebsiella pneumoniae* clone KPN 308894 (SEQ ID NO: 11, 392 to 581)
*En. cloaceae* EBC103795: *Enterobacter cloaceae* clone EBC103795 (SEQ ID NO: 12, 392 to 581)
FIG. 2 shows continuation of FIG. 1.

EMBODIMENTS FOR CARRYING OUT THE INVENTION

Hereafter, the present invention will be explained in detail.

The method for producing γ-Glu-Val-Gly or a salt thereof of the present invention comprises the step of reacting Val-Gly or a salt thereof with a γ-glutamyl group donor in the presence of GGT, a microorganism containing the enzyme, or a processed product thereof to generate γ-Glu-Val-Gly or a salt thereof. The method of the present invention is characterized in that GGT consists of a large subunit and a small subunit, and at least the small subunit has a specific mutation. Hereafter, GGT having such a specific mutation and the method for producing γ-Glu-Val-Gly or a salt thereof using it will be explained.

In this specification, amino acids are L-amino acids, unless especially mentioned.

<1> Mutant GGT

GGT having the aforementioned specific mutation (also referred to as "mutant GGT") can be obtained by modifying a ggt gene coding for GGT not having the specific mutation, so that the encoded GGT has the specific mutation, and expressing the obtained modified ggt gene. GGT not having the aforementioned specific mutation may be referred to as a wild-type GGT, and a ggt gene coding for the wild-type GGT may be referred to as a wild-type ggt gene. The wild-type GGT may have other mutations, so long as it does not have the specific mutation. The specific mutation will be explained later.

Examples of the wild-type GGT include GGT encoded by the ggt gene of *Escherichia coli* and homologues thereof, for example, GGT of *Escherichia coli*, and GGTs of other microorganisms, especially those of which small subunit has a similar structure.

The nucleotide sequence of the ggt gene of the *Escherichia coli* K-12 strain is described in Japanese Patent Laid-open No. 02-231085. Further, the nucleotide sequence of the ggt gene of the *Escherichia coli* K-12 W3110 strain is registered in the database as 4053592.4055334 of GenBank accession AP009048. The nucleotide sequence of this ggt gene is shown in SEQ ID NO: 1. Further, the amino acid sequence encoded by this nucleotide sequence is shown in SEQ ID NO: 2. In SEQ ID NO: 2, the positions 1 to 25 correspond to the leader peptide, the positions 26 to 390 correspond to the large subunit, and the positions 391 to 580 correspond to the small subunit.

As GGT homologues homologous to GGT of *Escherichia coli*, those containing a small subunit having an amino acid sequence showing a homology of 90% or more to the site corresponding to the small subunit in the amino acid sequence shown in SEQ ID NO: 2 (positions 391 to 580) are preferred. As the GGT homologues, those containing a large subunit having an amino acid sequence showing a homology of 90% or more to the site corresponding to the large subunit in the amino acid sequence shown in SEQ ID NO: 2 (positions 26 to 390) are preferred. Specific examples include GGTs of bacteria belonging to the family Enterobacteriaceae. Although the bacteria belonging to the family Enterobacteriaceae are not particularly limited, they include bacteria belonging to the genera of *Escherichia, Enterobacter, Erwinia, Klebsiella, Pantoea, Photorhabdus, Providencia, Salmonella, Serratia, Shigella, Morganella, Yersinia*, and so forth. In particular, bacteria classified into the family Enterobacteriaceae according to the taxonomy used in the NCBI (National Center for Biotechnology Information) database (http(colon)//www(dot)ncbi(dot)nlm(dot)nih(dot)gov/Taxonomy/Browser/wwwtax(dot)cgi?id=91347) are preferred. Specific examples include, for example, *Shigella flexneri, Shigella dysenteriae, Shigella boydii, Salmonella typhimurium, Klebsiella pneumoniae, Salmonella enterica, Enterobacter cloacae*, and so forth. The amino acid sequences of GGTs of *Shigella flexneri* 5 str. 8401 (GenBank accession ABF05491), *Shigella dysenteriae* Sd197 (GenBank accession ABB63568), *Shigella boydii* Sb227 (GenBank accession ABB67930), *Salmonella enterica typhimurium* strain ATCC 700720 (also designated as *Salmonella typhimurium* LT2, GenBank accession AAL22411), *Salmonella enterica enterica choleraesuis* strain SC-B67 (GenBank accession AAX67386), *Salmonella enterica typhi* strain Ty2 (GenBank accession AAO71440), *Klebsiella pneumoniae* ATCC 202080 (U.S. Pat. No. 6,610,836, SEQ ID NO: 10810), *Salmonella enterica* subsp. *enterica* serovar *Paratyphi* A str. ATCC 9150 (GenBank accession AAV79214), *Klebsiella pneumoniae* clone KPN308894 (WO02/077183, SEQ ID NO: 60310), and *Enterobacter cloacae* clone EBC103795 (WO02/077183, SEQ ID NO: 56162) are shown in SEQ ID NOS: 3 to 12.

The positions of the leader peptide, the large subunit, and the small subunit in each GGT are shown in Table 1. Further, alignment of the amino acid sequences of the small subunits of those GGTs is shown in FIGS. 1 and 2. The consensus sequence of the small subunit amino acid sequences is shown in FIGS. 1 and 2 and SEQ ID NO: 13. Further, identities of the small subunits of those bacteria and the small subunit of *Escherichia coli* are shown in Table 1. The amino acid codes used in FIGS. 1 and 2 are as follows. Specific examples of X include the amino acid residues locating at positions corresponding to the positions of X in the GGT small subunits of the bacteria described in the alignment shown in FIGS. 1 and 2. For example, X at the position 4 of SEQ ID NO: 13 is Tyr or Phe.

A: Ala, C: Cys, D: Asp, E: Glu, F: Phe, G: Gly, H: His, I: Ile, K: Lys, L: Leu, M: Met, N: Asn, P: Pro, Q: Gln, R: Arg, S: Ser, T: Thr, V: Val, W: Trp, X: Xaa, Y: Tyr

TABLE 1

| Bacterium | SEQ ID NO | Leader peptide | Large subunit | Small subunit | Identity of small subunit (%) |
|---|---|---|---|---|---|
| *Escherichia coli* | 2 | 1-25 | 26-390 | 391-580 | |
| *Shigella flexneri* 5 str. 8401 | 3 | 1-25 | 26-390 | 391-580 | 99 |
| *Shigella dysenteriae* Sd197 | 4 | 1-25 | 26-391 | 392-581 | 99 |
| *Shigella boydii* strain Sb227 | 5 | 1-25 | 26-387 | 388-577 | 99 |
| *Salmonella enterica typhimurium* strain ATCC 700720 | 6 | 1-24 | 25-390 | 391-580 | 95 |
| *Salmonella enterica enterica choleraesuis* strain SC-B67 | 7 | 1-24 | 25-390 | 391-580 | 95 |
| *Salmonella enterica typhi* strain Ty2 | 8 | 1-24 | 25-390 | 391-580 | 95 |
| *Klebsiella pneumoniae* strain ATCC 202080 | 9 | 1-32 | 33-399 | 400-589 | 95 |
| *Salmonella enterica* subsp. *enterica* serovar *Paratyphi* A str. ATCC 9150 | 10 | 1-24 | 25-390 | 391-580 | 94 |
| *Klebsiella pneumoniae* clone KPN308894 | 11 | 1-24 | 25-391 | 392-581 | 95 |
| *Enterobacter cloacae* clone EBC103795 | 12 | 1-24 | 25-391 | 392-581 | 93 |

Preferred examples of the wild-type GGT are those having the amino acid sequence of SEQ ID NO: 13 in the small subunit.

The mutant GGT of the present invention has one or more mutations at one or more residues selected from the following residues in the small subunit:
N411, T413, Q430, P441, V443, Y444, L446, A453, D472, G484, S498, Q542, D561, S572.

In the above indications, the letters on the left side of the numerals represent type of amino acid residue, and the numerals represent position in GGT. The position of amino acid residue is represented as the position on the amino acid sequence of the GGT precursor (protein consisting of the leader peptide, the large subunit, and the small subunit connected in this order) encoded by ORFs of the ggt gene. For example, the amino acid residue of the N-terminus of the GGT small subunit of *Escherichia coli* corresponds to the position 26 of SEQ ID NO: 2. The term amino acid sequence of GGT may henceforth mean the amino acid sequence of the GGT precursor, unless especially indicated.

The amino acid residue existing at the position of the mutation after the substitution may be any amino acid residue so long as it is an amino acid residue other than the original amino acid residue, and specific examples of the mutation include those selected from the following mutations:
N411Q
T413(H, N, A)
Q430(M, N)
P441A
V443(E, L, G, N, Q, A)
Y444(D, E, N, A)
L446A
A453S
D472I
G484(S, A, E)
S498C
Q542H
D561N
S572K.

The meanings of the letters representing the type of amino acid in the indications of the mutations are the same as those described above. The numerals represent the positions of the mutation. The letters on the left side of the numerals represent the amino acid residues existing in the wild-type, and the letters on the right side of the numerals represent the amino acid residue existing after the mutation. For example, "N411Q" means a substitution of Gln residue for the Asn residue at the position 411. Further, the letters in the parentheses on the right side of the numerals collectively represent amino acid residues existing after the mutation. For example, T413(H, N, A) means substitution of His, Asn or Ala residue for the Thr residue at the position 413.

More specific examples of the mutant GGT of the present invention include those having any one of the following mutations in the small subunit. The collective indications of two or more mutations using the symbol "+" means a double mutation or a more multiple mutation. For example, (N411Q+Q430N) means that the mutant GGT simultaneously has the N411Q mutation and the Q430N mutation. N411Q, T413H, T413N, T413A, Q430M, Q430N, P441A, V443E, V443L, V443G, V443N, V443Q, V443A, Y444D, Y444E, Y444N, Y444A, L446A, A453S, D472I, G484S, G484A, G484E, S498C, Q542H, D561N, S572K,
(N411Q+Q430N),
(N411Q+S572K)
(T413N+G484E)
(T413N+G484S)
(T413A+Y444E)
(T413H+Y444E)
(T413N+Y444E)
(Q430N+Y444E)
(Q430N+Y444D)
(Q430N+Y444N)
(P441A+Y444E)
(V443A+Y444E)
(V443E+Y444E)
(V443G+Y444E)
(V443L+Y444E)
(V443N+Y444E)
(V443Q+Y444E)
(V443A+Y444E)
(Y444E+L446A)
(Y444E+A453S)
(Y444E+D472I)
(Y444E+G484A)
(Y444E+G484S)
(Y444E+Q542H)
(Y444E+D561N)
(T413N+Y444E+V443A)
(T413N+Y444E+A453S)
(T413N+Y444E+S498C)
(T413N+Y444E+Q542H)
(G484S+Y444E+T276N)
(G484S+Y444E+V443A)
(G484S+Y444E+Q542H)
(Q430N+Y444E+T413N)
(T413H+Y444E+G484S)
(T413N+Y444E+G484S)
(T413N+Y444E+G484S+V443A)
(T413N+Y444E+G484S+A453S)
(T413N+Y444E+G484S+Q542H)
(T413N+Y444E+G484S+S572K)
(T413N+Y444E+G484S+Q430N)
(T413N+Y444E+G484E+S498C)

As for the aforementioned mutations, the positions 413, 472, and 572 are novel mutation sites, and N411Q, Q430M, Q430N, Q430P, Q430S, Q430Y, Y444D, Y444E, D472S, and G484S are novel mutations.

Among the aforementioned mutations, preferred are those with which generation of γ-Glu-Val-Gly was confirmed in Example 5. Further, those especially preferred for the method of the present invention are those with which γ-Glu-Val-Gly generation amount of 40 mM or more concerning a single mutation, or 60 mM or more concerning a complex mutation was obtained in Example 5. For example, the enzyme having N411Q, Q430M, Y444A, Y444D, Y444E, G484S, a double mutation, triple mutation, or quadruple mutation of the foregoing mutations is preferred.

Further, from another aspect, the Y444E mutation or a complex mutation of the Y444E mutation and one or more other mutations among the aforementioned mutations is also preferred.

Furthermore, as the mutant γ-glutamyltransferase of the present invention, especially preferred are mutant enzymes showing a higher activity compared with the known mutant γ-glutamyltransferase having the Y444A mutation (Glu-Val-Gly production amount observed in Example 5 is 52.5 mM), such as the enzymes having Y444D, Y444E, a double mutation, triple mutation, or quadruple mutation of the aforementioned mutations.

As for GGTs of microorganisms other than *Escherichia coli*, the positions of the mutations thereof corresponding to the mutations on the amino acid sequence of GGT of *Escherichia coli* are represented by the corresponding positions in GGT of *Escherichia coli* determined in alignment of the amino acid sequences of the GGTs of the other microorganisms and the amino acid sequence of GGT of *Escherichia coli*. For example, an amino acid residue of a position 100 in an amino acid sequence of GGT of a certain microorganism corresponds to the position 101 of the amino acid sequence of GGT of *Escherichia coli* in the alignment, that amino acid residue of the position 100 is regarded as the amino acid residue of the position 101. In the present invention, a residue corresponding to a specific residue in SEQ ID NO: 2 means a residue corresponding to the specific amino acid residue in the amino acid sequence of SEQ ID NO: 2 in the alignment of the amino acid sequence of SEQ ID NO: 2 and an objective sequence, as described above. Similarly, a mutation corresponding to a specific mutation in SEQ ID NO: 2 is a mutation at a residue corresponding to a residue of the specific mutation in the amino acid sequence of SEQ ID NO: 2 in the alignment of the amino acid sequence of SEQ ID NO: 2 and an objective sequence, as described above.

As a means for performing the alignment, known gene analysis software can be used. Specific examples of such software include DNASIS produced by Hitachi Solutions, GENETYX produced by Genetyx, and so forth (Elizabeth C. Tyler et al., Computers and Biomedical Research, 24(1), 72-96, 1991; Barton G J et al., Journal of Molecular Biology, 198(2), 327-37, 1987).

The positions of the mutations do not necessarily represent the absolute positions from the N-terminus in the amino acid sequences of mutant GGTs, and represent relative positions with respect to the amino acid sequence shown in SEQ ID NO: 2. For example, if one amino acid residue of GGT having the amino acid sequence shown in SEQ ID NO: 2 is deleted at a position on the N-terminus side with respect to a position n, this position n becomes an (n−1) position from the N-terminus. However, even in such a case, the amino acid residue of this position is regarded as the amino acid residue of the position n. An absolute position of an amino acid substitution can be determined on the basis of alignment of an amino acid sequence of an objective GGT and the amino acid sequence of SEQ ID NO: 2. The method for performing the alignment for this case is the same as the method described above.

Although the mutant GGT of the present invention may not contain a mutation in the large subunit, it may have any of the mutations shown below:
P27H, E38K, L127V, F174A, F174I, F174L, F174M, F174V, F174W, F174Y, T246R, T276N, V301L.

Examples of the combination of the mutations of the small subunit and the large subunit include the following combinations:
(E38K+Y444E)
(F174A+Y444E)
(F174I+Y444E)
(F174L+Y444E)
(F174M+Y444E)
(F174V+Y444E)
(F174W+Y444E)
(F174Y+Y444E)
(T246R+Y444E)
(V301L+Y444E)
(T413N+Y444E+P27H)
(T413N+Y444E+E38K)
(T413N+Y444E+L127V)
(T413N+Y444E+T276N)
(G484S+Y444E+T276N)
(G484S+Y444E+P27H)

Furthermore, the mutant GGT of the present invention may be a conservative variant of the proteins having the aforementioned amino acid sequences, i.e., a homologue, an artificially modified protein or the like of the proteins concerning the amino acid sequence thereof, such as any of the amino acid sequences of SEQ ID NOS: 2 to 12, so long as the GGT activity is not degraded. That is, the mutant GGT of the present invention may have any of the aforementioned amino acid sequences including, in addition to the aforementioned specific mutations, substitutions, deletions, insertions, additions, or inversions of one or several amino acid residues. Although the number meant by the term "one or several" can differ depending on the positions of amino acid residues in the three-dimensional structure or the types of amino acid residues of the protein, specifically, it is preferably 1 to 20, more preferably 1 to 10, still more preferably 1 to 5. The conservative mutation is typically a conservative substitution. The conservative substitution is a mutation wherein substitution takes place mutually among Phe, Trp, and Tyr, if the substitution site is an aromatic amino acid; among Leu, Ile and Val, if the substitution site is a hydrophobic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having a hydroxyl group. Substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like can be a result of a naturally-occurring mutation due to an individual difference, difference of species, or the like of a microorganism from which the gene is derived (mutant or variant).

Further, GGT having such a conservative mutation as described above can be a protein showing a homology of, for example, 80% or more, preferably 90% or more, more preferably 95% or more, still more preferably 97% or more, particularly preferably 99% or more, to any of the amino acid sequences of SEQ ID NOS: 2 to 12, and having the GGT activity.

In this specification, "homology" can mean "identity".

Further, GGT may be a protein encoded by a DNA that is able to hybridize with a prove having a nucleotide sequence complementary to the nucleotide sequence of SEQ ID NO: 1, or a probe that can be prepared from the complementary sequence under stringent conditions, and having the GGT activity. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, for example, conditions of hybridization at 42° C. and washing with a buffer containing 1×SSC and 0.1% SDS at 42° C., more preferably conditions of hybridization at 65° C. and washing with a buffer containing 0.1×SSC and 0.1% SDS at 65° C. The factors affecting the stringency for hybridization include various factors other than the aforementioned temperature conditions, and those skilled in the art can realize a stringency corresponding to the stringency exemplified above by using an appropriate combination of the various factors.

The probe used for the hybridization may be a part of a complementary sequence of the ggt gene. Such a probe can be produced by PCR using oligonucleotides synthesized on the basis of a known gene sequence as primers and a DNA fragment containing the nucleotide sequence as a template. For example, when a DNA fragment having a length of about 300 bp is used as the probe, the washing conditions of the hybridization can be, for example, 50° C., 2×SSC and 0.1% SDS.

The mutant GGT of the present invention can be produced by inserting a mutant ggt gene coding for it into an appropriate vector, and introducing the obtained recombinant vector into an appropriate host to allow expression thereof. Further, a microorganism containing the mutant GGT used for the method for producing γ-Glu-Val-Gly described later can be obtained by introducing the recombinant vector into an appropriate host microorganism.

The ggt gene having the specific mutation can be obtained by, for example, modifying a nucleotide sequence of a wild-type ggt gene, for example, a ggt gene coding for any of the amino acid sequences of SEQ ID NOS: 2 to 12, by the site-directed mutagenesis method, so that the amino acid residue of the specific position of the encoded GGT is replaced with another amino acid residue.

Examples of the site-directed mutagenesis method for introducing an objective mutation at an intended site of DNA include, for example, a method using PCR (Higuchi, R., 61, in PCR technology, Erlich, H. A. Eds., Stockton Press, 1989; Carter P., Meth. In Enzymol., 154, 382, 1987), as well as a method of using a phage (Kramer, W. and Frits, H. J., Methods in Enzymology, 154, 350, 1987; Kunkel, T. A. et al., Methods in Enzymology, 154, 367, 1987), and so forth.

The vector into which a mutant ggt gene is incorporated is not particularly limited so long as a vector that can replicate in the host is chosen. When *Escherichia coli* is used as the host, examples of such a vector include plasmids that can autonomously replicate in this bacterium. For example, pUC19, pET, pGEMEX, pGEM-T and so forth can be used. Preferred examples of the host include *Escherichia coli* strains. However, other than these, any of microorganisms in which a replication origin and a mutant ggt gene of a constructed recombinant DNA can function, a recombinant DNA can be expressed, and the mutant ggt gene can be expressed can be used as the host. As the host, for example, Gram-negative bacteria including *Escherichia* bacteria such as *Escherichia coli*, *Enterobacter* bacteria, *Pantoea* bacteria, and so forth, and Gram-positive bacteria including *Bacillus* bacteria, *Corynebacterium* bacteria, and so forth can be used. For example, *Bacillus subtilis* is known to secrete produced GGT out of cells (Xu et al., Journal of Bacteriology, Vol. 178, No. 14, 1996), and a mutant GGT may be secreted out of cells. In addition, an objective mutant ggt gene may be expressed by using cells of yeast, mold, or the like.

Examples of transformation methods include treating recipient cells with calcium chloride to increase permeability for DNA, which has been reported for *Escherichia coli* K-12 (Mandel, M. and Higa, A., J. Mol. Biol., 53:159-162, 1970), preparing competent cells from cells which are at the growth phase, followed by transformation with DNA, which has been reported for *Bacillus subtilis* (Duncan, C. H., Wilson, G. A. and Young, F. E., Gene, 1:153-167, 1977), and so forth. Alternatively, a method of making DNA-recipient cells into protoplasts or spheroplasts, which can easily take up recombinant DNA, followed by introducing a recombinant DNA into the cells, which is known to be applicable to *Bacillus subtilis*, actinomycetes and yeasts (Chang, S, and Choen, S. N., Mol. Gen. Genet., 168:111-115, 1979; Bibb, M. J., Ward, J. M. and Hopwood, O. A., Nature, 274:398-400, 1978; Hinnen, A., Hicks, J. B. and Fink, G. R., Proc. Natl. Sci., USA, 75:1929-1933, 1978) can also be employed. In addition, transformation of microorganisms can also be performed by the electroporation method (Japanese Patent Laid-open No. 2-207791).

The promoter for expressing the mutant ggt gene may be a promoter inherent to the ggt gene, or a promoter of another gene. Examples of promoters of other genes include rpoH promoter, lac promoter, trp promoter, trc promoter, tac promoter, PR promoter and PL promoter of lambda phage, tet promoter, and so forth.

Further, as a vector into which the ggt gene is inserted, an expression vector containing a promoter suitable for gene expression may also be used.

A transformant introduced with the recombinant DNA containing the mutant ggt gene obtained as described above can be cultured in an appropriate medium containing a carbon source, a nitrogen source, inorganic ions, and organic nutrients if needed to allow expression of the mutant GGT.

When a microorganism that expresses a mutant ggt gene is used for producing γ-Glu-Val-Gly, the microorganism is preferably deficient in the peptidase D (PepD). The term "deficient in PepD" means that the microorganism is completely deficient in PepD, or the microorganism has a reduced amount or activity of PepD compared with a wild-type strain. The inventors of the present invention found that PepD is deeply involved in the decomposition of Val-Gly in *Escherichia coli*. By making a microorganism that expresses a mutant GGT deficient in PepD, the generation amount of γ-Glu-Val-Gly, which is generated from Val-Gly as a substrate, can be increased.

The microorganism can be made deficient in PepD by, for example, reducing expression of the pepD gene coding for PepD. The expression of the pepD gene can be reduced by modifying the pepD gene on a chromosome so that a wild-type RNA or wild-type protein is not expressed, for example, by disrupting the pepD gene. As methods for such gene disruption, there are the method utilizing a linear DNA such as the method called "Red-driven integration" (Datsenko, K. A. and Wanner, B. L., Proc. Natl. Acad. Sci. USA, 97:6640-6645, 2000), and the method based on the combination of the Red-driven integration method and the λ phage excision system (Cho, E. H., Gumport, R. I., Gardner, J. F., J. Bacteriol., 184:5200-5203, 2002) (refer to WO2005/010175), the methods utilizing a plasmid having a temperature sensitive replication origin, a plasmid capable of conjugative transfer, a suicide vector not having a replication origin in a host, and so forth (U.S. Pat. No. 6,303,383, or Japanese Patent Laid-open No. 05-007491).

The nucleotide sequence of the pepD gene of *Escherichia coli* and the amino acid sequence encoded by this gene are shown in SEQ ID NOS: 14 and 15, respectively. Further, the nucleotide sequence of pepA, pepB, pepE, and pepN genes, which are other peptidase genes of *Escherichia coli*, are shown in SEQ ID NOS: 16, 18, 20, and 22, respectively. Further, the amino acid sequences encoded by these genes are shown in SEQ ID NOS: 17, 19, 21, and 23, respectively. So long as the microorganism that expresses a mutant ggt gene is deficient in PepD, it may be deficient in another arbitrary peptidase.

<2> Method for Producing γ-Glu-Val-Gly or Salt Thereof.

By reacting Val-Gly or a salt thereof with a γ-glutamyl group donor in the presence of the mutant GGT obtained as described above, a microorganism containing the mutant GGT, or a processed product thereof to generate γ-Glu-Val-Gly or a salt thereof, γ-Glu-Val-Gly or a salt thereof can be produced.

A microorganism containing the mutant GGT can be produced by culturing a microorganism into which the mutant ggt gene has been introduced in an expressible form under conditions enabling expression of the gene to allow growth of cells. The medium used for the culture is not particularly limited so long as the objective microorganism can grow in it, and there can be used a conventional medium containing a carbon source, a nitrogen source, a sulfur source, inorganic ions, and other organic components as required.

As the carbon source, saccharides such as glucose, fructose, sucrose, glycerol, ethanol, molasses and starch hydrolysate, and organic acids such as fumaric acid, citric acid and succinic acid can be used.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

Examples of the sulfur source include inorganic sulfur compounds, such as sulfates, sulfites, sulfides, hyposulfites and thiosulfates.

As organic trace amount nutrients, it is desirable to add required substances such as vitamin $B_1$, yeast extract and so forth in appropriate amounts. Other than these, potassium phosphate, magnesium sulfate, iron ions, manganese ions and so forth are added in small amounts.

The culture conditions can be appropriately chosen according to the microorganism to be used. The culture is preferably performed at a culture temperature of, for example, 20 to 45° C., preferably 24 to 45° C. The culture is preferably performed as aeration culture at an oxygen concentration of 5 to 50%, desirably about 10%, with respect to the saturated concentration. Further, pH during the culture is preferably 5 to 9. For adjusting pH, inorganic or organic acidic or alkaline substances, such as calcium carbonate, ammonia gas, and aqueous ammonia, can be used.

By culturing the microorganism preferably for about 10 to 120 hours under such conditions as described above, the mutant GGT is accumulated in the periplasm of cells.

In addition, by appropriately choosing the host to be used and designing the ggt gene, it is also possible to accumulate GGT in cells or produce GGT with allowing secretion thereof out of cells.

The mutant GGT may be used in a state of being contained in cells, or may be used as a crude enzyme fraction extracted from the cells or a purified enzyme. The mutant GGT can be extracted by the same method as those for conventional extraction of a periplasmic enzyme, for example, osmotic shock method, freezing and thawing method, and so forth. Further, the mutant GGT can be purified by an appropriate combination of methods usually used for purification of enzyme, such as ammonium sulfate fractionation, ion exchange chromatography, hydrophobic chromatography, affinity chromatography, gel filtration chromatography, and electrofocusing. When GGT is produced and secreted out of cells, the mutant GGT collected from the medium can be used.

The processed product of the microorganism containing mutant GGT is not particularly limited so long as it contains the mutant GGT in a state that the mutant GGT can function, and examples include disrupted cells, cell extract, partially purified products thereof, purified enzyme, and so forth, as well as cells immobilized with acrylamide, carrageenan, or the like, immobilized enzymes comprising the mutant GGT immobilized on a solid phase such as resin, and so forth.

In the presence of the mutant GGT, a microorganism containing the mutant GGT or a processed product thereof obtained as described above, Val-Gly and a γ-glutamyl group donor are reacted.

Val-Gly or a salt thereof can be produced by a chemical synthesis method using formyl-L-valine and glycine ethyl ester as the starting materials (Journal of the American Chemical Society, 80, 1154-1158, 1958). Alternatively, it is also possible to use a chemical synthesis method using N-carboxyanhydride of valine (valine-NCA) and glycine as the starting materials (Canadian Journal of Chemistry, 51 (8), 1284-87, 1973). Further, other methods known as peptide synthesis methods can also be used ("Fundamentals and Experiments of Peptide Synthesis", Maruzen Co., Ltd., 1985).

Further, when Val-Gly to be used is in the form of a salt, it may be any salt so long as a chemically acceptable salt is used. Specific examples of the "chemically acceptable salt" include, for acidic groups such as carboxyl group, ammonium salt, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine, and dicyclohexylamine, salts with basic amino acids such as arginine and lysine, and for basic groups, salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and salts with organic sulfonic acid such as methanesulfonic acid, benzenesulfonic acid, and p-toluenesulfonic acid.

Furthermore, when γ-Glu-Val-Gl obtained by the method of the present invention is in the form of a salt, it may be a chemically and pharmaceutically acceptable edible salt, and examples include, for acidic groups such as carboxyl group, ammonium salts, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine, and dicyclohexylamine, salts with basic amino acids such as arginine and lysine, and for basic groups, salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and salts with organic sulfonic acid such as methanesulfonic acid, benzenesulfonic acid, and p-toluenesulfonic acid. When it is used for foods, it is sufficient that it is an edible salt.

Peptide production using an enzymatic reaction can be performed by using any of the following methods reported as methods for producing a peptide, namely, a condensation reaction using an N-protected and C-non-protected carboxyl component and an N-non-protected and C-protected amine component (reaction 1), a substitution reaction using an N-protected and C-protected carboxyl component and an N-non-protected and C-protected amine component (reaction 2), a substitution reaction using an N-non-protected and C-protected carboxyl component and an N-non-protected and C-protected amine component (reaction 3), a substitution reaction using an N-non-protected and C-protected carboxyl component and an N-non-protected and C-non-protected amine component (reaction 4), or a transfer reaction using an N-non-protected and C-protected carboxyl component and an N-non-protected and C-non-protected amine component (reaction 5), and purifying Val-Gly or a salt thereof from the reaction product.

Examples of the reaction 1 include, for example, the method for producing Z-aspartylphenylalanine methyl ester from Z-aspartic acid and phenylalanine methyl ester (Japanese Patent Laid-open No. 53-92729), examples of the reaction 2 include, for example, the method for producing acetylphenylalanylleucinamide from acetylphenylalanine ethyl ester and leucinamide (Biochemical J., 163, 531, 1977), examples of the reaction 3 include, for example, the method for producing arginylleucinamide from arginine ethyl ester and leucinamide (WO90/01555), examples of the reaction 4 include, for example, the method for producing tyrosylalanine from tyrosine ethyl ester and alanine (EP 278787 A1, EP 359399 B1), and examples of the reaction 5 include, for example, the method for producing alanylglutamine from alanine methyl ester and glutamine (W2004/011653). It is possible to apply the above reactions to the production of Val-Gly or a salt thereof. In such a case, by reacting valine having an esterified or amidated carboxyl group and glycine having free amino group in the presence of a peptide-producing enzyme, and purifying Val-Gly from the reaction product, Val-Gly can be produced.

The γ-glutamyl group donor can be chosen from γ-glutamyl compounds. Examples include, for example, glutamine, glutamic acid γ-alkyl esters such as glutamic acid γ-methyl ester, salts thereof, and so forth. Among these, glutamine and a salt thereof are preferred. This salt may also be such a chemically acceptable salt as explained above, and the definition thereof is the same as described above.

The reaction of Val-Gly or a salt thereof and the γ-glutamyl group donor may be performed by the batch method or the column method. When the batch method is used, Val-Gly or a salt thereof, the γ-glutamyl group donor and the mutant GGT, a microorganism containing the mutant GGT, or a processed product thereof can be mixed in a reaction mixture contained in a reaction vessel. The reaction may be performed as a standing reaction, or with stirring. When the column method is used, a reaction mixture containing Val-Gly or a salt thereof and the γ-glutamyl group donor can be passed thorough a column filled with such immobilized cells or immobilized enzyme as described above.

The reaction mixture preferably consists of water or a buffer containing Val-Gly or a salt thereof and the γ-glutamyl group donor, and preferably has pH of 6.0 to 10.0, more preferably 6.5 to 9.0.

The reaction time or the flow rate of the reaction mixture can be appropriately determined according to the concentrations of the substrates, amount of the mutant GGT with respect to the substrates, and so forth. Specifically, for example, the amount of the enzyme to be added can be determined by measuring the enzyme activity under a certain condition, and determining the amount on the basis of the measured activity value. For example, the enzyme activity can be measured by using an appropriate amount of enzyme with a composition of the reaction mixture of 0.1 M glutamine, 0.1 M Val-Gly, and 0.1 M potassium phosphate (pH 7.6), a reaction temperature of 37° C., and a reaction time of 1 to 10 minutes. For example, when the amount of the enzyme which produces 1 μmol of γ-Glu-Val-Gly in 1 minute under the aforementioned conditions is defined to be 1 U, the reaction can be performed with substrate concentrations of 1 to 2000 mM glutamine as the γ-glutamyl group donor and 1 to 2000 mM Val-Gly, as well as an enzyme concentration of 0.1 to 100 U/ml.

The reaction temperature is usually 15 to 50° C., preferably 15 to 45° C., more preferably 20 to 40° C.

Although the molar ratio of Val-Gly or a salt thereof and the γ-glutamyl group donor in the reaction mixture may vary depending on the type of the γ-glutamyl group donor used for the reaction, the molar ratio of Val-Gly:γ-glutamyl group donor is usually preferably 1:0.1 to 1:10. The concentrations of Val-Gly and the γ-glutamyl group donor in the reaction mixture are usually 1 to 2000 mM, preferably 100 to 2000 mM, more preferably 100 to 1000 mM.

The amount of the mutant GGT to the substrates is usually 0.01 to 1000 U, preferably 0.1 to 500 U, more preferably 0.1 to 100 U, with respect to 1 mmol of the substrates.

When a microorganism containing the mutant GGT or a processed product thereof is used, if a peptidase, especially PepD, is contained, Val-Gly as the substrate and/or γ-Glu-Val-Gly as the product may be easily decomposed. Therefore, it is preferable to use a PepD-deficient strain as the microorganism. Alternatively, the peptidase activity can also be suppressed by adding a metal chelating agent which chelates metal ions required for the enzyme activity of peptidase, such as $Co^{2+}$, $Mn^{2+}$, and $Fe^{2+}$, to the reaction mixture. Examples of the metal chelating agent include EDTA and so forth. The concentration of the metal chelating agent in the reaction mixture is usually 0.01 to 500 mM, preferably 0.01 to 100 mM, more preferably 0.1 to 10 mM. When a purified mutant GGT or purified mutant GGT not containing the peptidase activity is used, the metal chelating agent is unnecessary, but it may be contained.

As described above, γ-Glu-Val-Gly is produced in the reaction mixture. γ-Glu-Val-Gly or a salt thereof can be collected from the reaction mixture by, for example, various chromatography techniques such as ion exchange chromatography, reversed phase high performance liquid chromatography, and affinity chromatography, crystallization and recrystallization from a solution, and so forth.

EXAMPLES

Hereafter, the present invention will be still more specifically explained with reference to examples.

Example 1

Construction of GGT Expression Plasmid

A GGT expression plasmid was constructed by inserting the ggt gene of *Escherichia coli* into an expression plasmid pSF12_Sm_Aet containing the rpoH promoter described below.

First, in order to delete the NdeI recognition site (restriction site originated in the pUC18) contained in the plasmid pSF_Sm_Aet derived from pUC18 containing a peptide-producing enzyme gene derived from the *Sphingobacterium* sp. FERM BP-8124 and the phoC promoter (WO2006/075486 A1), PCR was performed by using pSF_Sm_Aet as the template and primers having the sequences of SEQ ID NOS: 24 and 25 with "Quik Change Site-Directed Mutagenesis Kit" of Stratagene according to the manufacturer's protocol. The obtained PCR product was digested with DpnI, and then the *Escherichia coli* JM109 strain was transformed with the reaction mixture, applied to the LB agar medium containing 100 mg/L of ampicillin sodium (Amp), and cultured at 25° C. for 36 hours. Plasmids were extracted from the grown colonies of the transformants in a known manner, the nucleotide sequences thereof were confirmed by using 3100 Genetic Analyzer (Applied Biosystems), and the plasmid having the objective structure was designated as pSF1_Sm_Aet. The FERM BP-8124 strain was designated as AJ110003, and deposited at the independent administrative agency, National Institute of Advanced Industrial Science and Technology, International Patent Organism Depository (Tsukuba Central 6, 1-1, Higashi 1-Chome, Tsukuba-shi, Ibaraki-ken, 305-8566, Japan) on Jul. 22, 2002 in line with the provisions of the Budapest Treaty, and assigned with an accession number of FERM BP-8124.

Then, in order to introduce the NdeI recognition sequence into pSF1_Sm_Aet at the site of the start methionine moiety of the peptide-producing enzyme gene derived from *Sphingobacterium* sp. FERM BP-8124, PCR was performed by using pSF1_Sm_Aet as the template and primers having the sequences of SEQ ID NOS: 26 and 27 with "Quik Change Site-Directed Mutagenesis Kit" mentioned above. The obtained PCR product was digested with DpnI, and then the *Escherichia coli* JM109 strain was transformed with the reaction mixture, applied to the LB agar medium containing 100 mg/L of Amp, and cultured at 25° C. for 24 hours. Plasmids were extracted from the grown colonies of the transformants in a known manner, the nucleotide sequences thereof were confirmed by using 3100 Genetic Analyzer (Applied Biosystems), and the plasmid having the objective structure was designated as pSF2_Sm_Aet.

Then, the phoC promoter of pSF2_Sm_Aet was replaced with the rpoH promoter according to the following method. The rpoH promoter region was obtained by PCR from the *Escherichia coli* W3110 strain genomic DNA. PCR was performed by using the W3110 strain genomic DNA as the template, a primer having the sequence of SEQ ID NO: 28 (rpoH promoter region having a nucleotide sequence containing the XbaI recognition sequence at the 5' end) as the sense primer, a primer having the sequence of SEQ ID NO: 29 (complementary nucleotide sequence of the rpoH promoter region having a nucleotide sequence containing the NdeI recognition sequence at the 5' end) as the antisense primer, and KOD-plus- (Toyobo) as the polymerase, with 30 cycles of 94° C. for 30 seconds, 52° C. for 1 minute, and 68° C. for 30 seconds according to the manufacturer's protocol.

Then, the obtained PCR product was digested with XbaI/NdeI, and subjected to agarose gel electrophoresis, a portion of the DNA of about 0.4 kb was excised, and the DNA was ligated to the pSF2_Sm_Aet fragment (about 4.7 kb) digested with XbaI/NdeI by using DNA Ligation Kit Ver. 2.1 (Takara Bio). The *Escherichia coli* JM109 strain was transformed with the reaction mixture, applied to the LB agar medium containing 100 mg/L of Amp, and cultured at 25° C. for 36 hours. Plasmids were extracted from the grown colonies of the transformants in a known manner, the nucleotide sequences thereof were confirmed by using 3100 Genetic Analyzer (Applied Biosystems), and the plasmid having the objective structure was designated as pSF12_Sm_Aet.

The ggt gene of the *Escherichia coli* was obtained by PCR from the *Escherichia coli* W3110 strain genomic DNA. PCR was performed by using the W3110 strain genomic DNA as the template, a primer having the sequence of SEQ ID NO: 30 (region containing the initiation codon of the ggt gene having a nucleotide sequence containing the NdeI recognition sequence at the 5' end) as the sense primer, a primer having the sequence of SEQ ID NO: 31 (complementary nucleotide sequence of the region containing the initiation codon of the ggt gene having a nucleotide sequence containing the PstI recognition sequence at the 5' end) as the antisense primer, and KOD-plus- (Toyobo), with 30 cycles of 94° C. for 30 seconds, 52° C. for 1 minute, and 68° C. for 120 seconds according to the manufacturer's protocol. Then, the obtained PCR product was digested with NdeI/PstI, and subjected to agarose gel electrophoresis, a portion of the objective DNA of about 1.8 kb was excised, and the DNA was ligated to the pSF12_Sm_Aet fragment digested with NdeI/PstI (about 3.0 kb) by using DNA Ligation Kit Ver. 2.1 (Takara Bio). The *Escherichia coli* JM109 strain was transformed with the reaction mixture, applied to the LB agar medium containing 100 mg/L of Amp, and cultured at 25° C. for 36 hours. Plasmids were extracted from the grown colonies of the transformants in a known manner, the nucleotide sequences thereof were confirmed by using 3100 Genetic Analyzer (Applied Biosystems), and the plasmid having the objective structure was designated as pSF12_ggt.

Example 2

Preparation of pepA Gene-, pepB Gene-, pepD Gene-, pepE Gene- and pepN Gene-Disrupted Strains Derived from *Escherichia coli* JM 109 Strain From the *Escherichia coli* JM109 strain as a parent strain, PepA, PepB, PepD, PepE, and PepN non-producing strains were constructed. PepA is encoded by the pepA gene (GenBank Accession: 7439053, SEQ ID NO: 16), PepB is encoded by the pepB gene (GenBank Accession: 7437614, SEQ ID NO: 18), PepD is encoded by the pepD gene (GenBank Accession: 7438954, SEQ ID NO: 14), PepE is encoded by the pepE gene (GenBank Accession: 7438857, SEQ ID NO: 20), and PepN is encoded by the pepN gene (GenBank Accession: 7438913, SEQ ID NO: 22).

Each gene was disrupted by a method consisting of a combination of the method called "Red-driven integration", first developed by Datsenko and Wanner (Proc. Natl. Acad. Sci. USA, vol. 97, No. 12, pp. 6640-6645, 2000), and an excision system derived from λ phage (J. Bacteriol., 2002 September, 184 (18):5200-3, Interactions between integrase and excisionase in the phage lambda excisive nucleoprotein complex, Cho E H, Gumport R I, and Gardner J F) (refer to WO2005/010175). According to the "Red-driven integration" method, using a PCR product obtained by using synthetic oligonucleotides in which a part of a target gene is designed on the 5' side, and a part of antibiotic resistance gene is designed on the 3' side, respectively, as primers, a gene-disrupted strain can be constructed in one step. By further using the excision system derived from λ phage in combination, the antibiotic resistance gene incorporated into the gene-disrupted strain can be eliminated.

As the template for PCR, the plasmid pMW118-attL-Cm-attR was used. pMW118-attL-Cm-attR (WO2006/078039) is a plasmid obtained by inserting attL and attR genes, which are the attachment sites of λ phage, and the cat gene, which is an antibiotic resistance gene, into pMW118 (Nippon Gene), and the genes are inserted in the order of attL-cat-attR. PCR was performed by using synthetic oligonucleotides as primers having sequences corresponding to the both ends of these attL and attR at the 3' ends and a sequence corresponding to a part of the pepA, pepB, pepD, pepE or pepN gene as the objective gene at the 5' ends.

That is, a DNA fragment for disruption of the pepA gene was prepared by performing PCR using pMW118-attL-Cm-attR as the template, the primers having the sequences of SEQ ID NOS: 32 and 33, and KOD-plus- of Toyobo, with 30 cycles of 94° C. for 30 seconds, 52° C. for 1 minute, and 68° C. for 120 seconds according to the manufacturer's protocol.

The DNA fragment for disruption of the pepB gene was obtained as follows. Namely, a fragment of about 1.0 kb locating upstream of the pepB gene was amplified by performing PCR using the *Escherichia coli* W3110 strain genomic DNA as the template, the primers having the sequences of SEQ ID NOS: 34 and 35, and KOD-plus- with 30 cycles of 94° C. for 30 seconds, 52° C. for 1 minute, and 68° C. for 60 seconds according to the manufacturer's protocol (DNA fragment A). Similarly, a fragment of about 1.0 kb locating downstream of the pepB gene was amplified by performing PCR using the primers having the sequences of SEQ ID NOS: 36 and 37, and KOD-plus- with 30 cycles of 94° C. for 30 seconds, 52° C. for 1 minute, and 68° C. for 60 seconds according to the manufacturer's protocol (DNA fragment B). Further, a fragment of about 1.6 kb was amplified by performing PCR using the plasmid pMW118-attL-Cm-attR as the template, the primers having the sequences of SEQ ID NOS: 38 and 39, and KOD-plus- with 30 cycles of 94° C. for 30 seconds, 52° C. for 1 minute, and 68° C. for 120 seconds according to the manufacturer's protocol (DNA fragment C). By using the obtained DNA fragments A, B and C in amounts of 50, 10, and 50 ng, respectively, PCR was performed by using KOD-plus- with 10 cycles of 94° C. for 2 minutes, 52° C. for 30 seconds, and 68° C. for 2 minutes according to the manufacturer's protocol. Then, second PCR was performed by using 1 μl of each of the obtained PCR products as the template together with the primers having the sequences of SEQ ID NOS: 34 and 37, and KOD-plus- with 30 cycles of 94° C. for 30 seconds, 52° C. for 1 minute, and 68° C. for 4 minutes according to the manufacturer's protocol to obtain the DNA fragment for disruption of the pepB gene.

The DNA fragment for disruption of the pepD gene was prepared by performing PCR using the primers having the sequences of SEQ ID NOS: 40 and 41 and KOD-plus- with 30 cycles of 94° C. for 30 seconds, 52° C. for 1 minute, and 68° C. for 120 seconds according to the manufacturer's protocol.

The DNA fragment for disruption of the pepE gene was prepared by performing PCR using the primers having the sequences of SEQ ID NOS: 42 and 43 and KOD-plus- with 30 cycles of 94° C. for 30 seconds, 52° C. for 1 minute, and 68° C. for 120 seconds according to the manufacturer's protocol.

The DNA fragment for disruption of the pepN gene was prepared by performing PCR using the primers having the sequences of SEQ ID NOS: 44 and 45 and KOD-plus- with 30 cycles of 94° C. for 30 seconds, 52° C. for 1 minute, and 68° C. for 120 seconds according to the manufacturer's protocol.

The DNA fragments for gene disruption obtained as described above were each purified by agarose gel electrophoresis, and introduced into the *Escherichia coli* JM109 strain harboring the plasmid pKD46 having temperature sensitive replication ability by electroporation. The plasmid pKD46 (Proc. Natl. Acad. Sci. USA, 97:12:6640-45, 2000) includes a total 2,154 nucleotide DNA fragment of phage λ (GenBank/EMBL accession no. J02459, nucleotide positions 31088 to 33241) containing genes coding for the Red recombinase of the λ Red homologous recombination system (γ, β, exo genes) under the control of the arabinose-inducible $P_{araB}$ promoter. The plasmid pKD46 is necessary for integration of the DNA fragments for gene disruption into the chromosome of the JM109 strain. Competent cells for electroporation were prepared as follows. Namely, *Escherichia coli* JM109 strain harboring the plasmid pKD46 was cultured at 30° C. for 20 hours in the LB medium containing 100 mg/L of Amp, and the culture was diluted 50 times with 2 ml of the SOB medium (Molecular Cloning A Laboratory Manual, 2nd edition, Sambrook, J. et al., Cold Spring Harbor Laboratory Press (1989)) containing Amp (100 mg/L). The cells in the obtained diluted suspension were grown at 30° C. to an $OD_{600}$ of about 0.3, then added with 70 μl of 10% (v/v) L-arabinose, and cultured at 37° C. for 1 hour. Then, the obtained culture fluid was concentrated 65 times, and the cells were washed three times with 10% (v/v) glycerol and thereby made electrocompetent. Electroporation was performed by using 30 μl of the competent cells and about 100 ng of the PCR product.

After the electroporation, 0.27 mL of the SOC medium (Molecular Cloning A Laboratory Manual, 2nd edition, Sambrook, J. et al., Cold Spring Harbor Laboratory Press (1989)) was added to the cell suspension, and the cells were cultured at 37° C. for 3 hours, and then cultured at 37° C. on the LB agar medium containing chloramphenicol (Cm, 50 mg/L), and Cm resistant recombinant strains were chosen. Then, in order to remove the pKD46 plasmid, the strains were cultured at 42° C. on the LB agar medium containing Cm (50 mg/L), the obtained colonies were examined for the Amp resistance and the Amp sensitive strains where pKD46 had been removed were obtained. Disruption of the pepA gene, pepB gene, pepD gene, pepE gene, and pepN gene of the mutants identified with the Cm resistance gene was confirmed by PCR. The obtained pepA gene-, pepB gene-, pepD gene-, pepE gene-, and pepN gene-disrupted strains were designated as JM109ΔpepA:att-cat strain, JM109ΔpepB:att-cat strain, JM109ΔpepD:att-cat strain, JM109ΔpepE:att-cat strain, and JM109ΔpepN:att-cat strain, respectively.

Then, in order to remove the att-cat gene introduced into the pepA gene, pepB gene, pepD gene, pepE gene, and pepN gene, pMW-intxis-ts was used as the helper plasmid. pMW-intxis-ts is a plasmid carrying a gene coding for phage integrase (Int) and a gene coding for excisionase (Xis), and having temperature sensitive replication ability. If pMW-intxis-ts is introduced into a cell, it recognizes attL or attR on the chromosome to cause recombination, thus the gene between attL and attR is excised, and only the attB sequence remains on the chromosome. Competent cells of the JM109ΔpepA:att-cat strain, JM109ΔpepB:att-cat strain, JM109ΔpepD:att-cat strain, JM109ΔpepE:att-cat strain, and JM109ΔpepN:att-cat strain obtained above were prepared in a conventional manner, transformed with pMW-intxis-ts, and cultured at 30° C. on the LB agar medium containing 100 mg/L of Amp, and Amp resistant strains were chosen. Then, in order to remove the pMW-intxis-ts plasmid, the transformants were cultured at 42° C. on the LB agar medium, and Amp resistance and Cm resistance of the obtained colonies were examined to obtain Cm and Amp sensitive strains, which were strains where att-cat and pMW-intxis-ts had been removed, and the pepA gene, the pepB gene, the pepD gene, the pepE gene, or the pepN gene had been disrupted. These strains were designated as JM109ΔpepA strain, JM109ΔpepB strain, JM109ΔpepD strain, JM109ΔpepE strain, and JM109ΔpepN strain, respectively.

Example 3

Construction of Mutant ggt Genes

In order to construct mutant ggt genes, PCR was performed by using primers corresponding to various mutant ggt genes (SEQ ID NOS: 46 to 211) and pSF12_ggt mentioned in Example 1 as the template with "Quik change Site-Directed Mutagenesis Kit" of Stratagene according to the manufacturer's protocol. The relations between the mutations and the primers are shown in Tables 2 to 5.

After each of the obtained PCR products was digested with DpnI, the *Escherichia coli* JM109ΔpepA strain, JM109ΔpepB strain, JM109ΔpepD strain, JM109ΔpepE strain, and JM109ΔpepN strain were each transformed with the reaction mixture, applied to the LB agar medium containing 100 mg/L of Amp, and cultured at 25° C. for 36 hours. Plasmids were extracted from the grown colonies of the transformants in a known manner, the nucleotide sequences thereof were confirmed by using 3100 Genetic Analyzer (Applied Biosystems), and the objective transformants were used for further examination.

The plasmids introduced with various mutations were given with designations consisting of pSF12-ggt and indication of type of the mutation. For example, a plasmid having a mutant ggt gene coding for a mutant GGT having the Y444E mutation is described as pSF12-ggt(Y444E).

TABLE 2

| SEQ ID NO | Sequence | Introduced mutation |
|---|---|---|
| 46 | CCGAACGTTGCGGGGCTGGTGG | Y444A |
| 47 | CCACCAGCCCCGCAACGTTCGG | |
| 48 | CCGAACGTTGATGGGCTGGTGG | Y444D |
| 49 | CCACCAGCCCATCAACGTTCGG | |
| 50 | CCGAACGTTGAAGGGCTGGTGG | Y444E |
| 51 | CCACCAGCCCTTCAACGTTCGG | |
| 52 | CCGAACGTTAACGGGCTGGTGG | Y444N |
| 53 | CCACCAGCCCGTTAACGTTCGG | |
| 54 | GCTTAATAACGCGATGGATGATTTC | Q430A |
| 55 | GAAATCATCCATCGCGTTATTAAGC | |
| 56 | GCTTAATAACTGCATGGATGATTTC | Q430C |
| 57 | GAAATCATCCATGCAGTTATTAAGC | |
| 58 | GCTTAATAACGATATGGATGATTTC | Q430D |
| 59 | GAAATCATCCATATCGTTATTAAGC | |
| 60 | GCTTAATAACGAAATGGATGATTTC | Q430E |
| 61 | GAAATCATCCATTTCGTTATTAAGC | |
| 62 | GCTTAATAACTTTATGGATGATTTC | Q430F |
| 63 | GAAATCATCCATAAAGTTATTAAGC | |
| 64 | GCTTAATAACGGCATGGATGATTTC | Q430G |
| 65 | GAAATCATCCATGCCGTTATTAAGC | |
| 66 | GCTTAATAACCATATGGATGATTTC | Q430H |
| 67 | GAAATCATCCATATGGTTATTAAGC | |
| 68 | GCTTAATAACATTATGGATGATTTC | Q430I |
| 69 | GAAATCATCCATAATGTTATTAAGC | |
| 70 | GCTTAATAACAAAATGGATGATTTC | Q430K |
| 71 | GAAATCATCCATTTTGTTATTAAGC | |
| 72 | GCTTAATAACCTGATGGATGATTTC | Q430L |
| 73 | GAAATCATCCATCAGGTTATTAAGC | |
| 74 | GCTTAATAACATGATGGATGATTTC | Q430M |
| 75 | GAAATCATCCATCATGTTATTAAGC | |
| 76 | GCTTAATAACAACATGGATGATTTC | Q430N |
| 77 | GAAATCATCCATGTTGTTATTAAGC | |
| 78 | GCTTAATAACCCGATGGATGATTTC | Q430P |
| 79 | GAAATCATCCATCGGGTTATTAAGC | |
| 80 | GCTTAATAACCGCATGGATGATTTC | Q430R |
| 81 | GAAATCATCCATGCGGTTATTAAGC | |
| 82 | GCTTAATAACAGCATGGATGATTTC | Q430S |
| 83 | GAAATCATCCATGCTGTTATTAAGC | |
| 84 | GCTTAATAACACCATGGATGATTTC | Q430T |
| 85 | GAAATCATCCATGGTGTTATTAAGC | |
| 86 | GCTTAATAACGTGATGGATGATTTC | Q430V |
| 87 | GAAATCATCCATCACGTTATTAAGC | |
| 88 | GCTTAATAACTGGATGGATGATTTC | Q430W |
| 89 | GAAATCATCCATCCAGTTATTAAGC | |
| 90 | GCTTAATAACTATATGGATGATTTC | Q430Y |
| 91 | GAAATCATCCATATAGTTATTAAGC | |
| 92 | CCAGATGGATGCGTTCTCCGCC | D433A |
| 93 | GGCGGAGAACGCATCCATCTGG | |

TABLE 3

| SEQ ID NO | Sequence | Introduced mutation |
|---|---|---|
| 94 | CCAGATGGATTGCTTCTCCGCC | D433C |
| 95 | GGCGGAGAAGCAATCCATCTGG | |
| 96 | CCAGATGGATGAATTCTCCGCC | D433E |
| 97 | GGCGGAGAATTCATCCATCTGG | |
| 98 | CCAGATGGATTTTTTCTCCGCC | D433F |
| 99 | GGCGGAGAAAAAATCCATCTGG | |
| 100 | CCAGATGGATGGCTTCTCCGCC | D433G |
| 101 | GGCGGAGAAGCCATCCATCTGG | |
| 102 | CCAGATGGATCATTTCTCCGCC | D433H |
| 103 | GGCGGAGAAATGATCCATCTGG | |
| 104 | CCAGATGGATATTTTCTCCGCC | D433I |
| 105 | GGCGGAGAAAATATCCATCTGG | |
| 106 | CCAGATGGATAAATTCTCCGCC | D433K |
| 107 | GGCGGAGAATTTATCCATCTGG | |
| 108 | CCAGATGGATCTGTTCTCCGCC | D433L |
| 109 | GGCGGAGAACAGATCCATCTGG | |
| 110 | CCAGATGGATATGTTCTCCGCC | D433M |
| 111 | GGCGGAGAACATATCCATCTGG | |
| 112 | CCAGATGGATAACTTCTCCGCC | D433N |
| 113 | GGCGGAGAAGTTATCCATCTGG | |
| 114 | CCAGATGGATCCGTTCTCCGCC | D433P |
| 115 | GGCGGAGAACGGATCCATCTGG | |
| 116 | CCAGATGGATCAGTTCTCCGCC | D433Q |
| 117 | GGCGGAGAACTGATCCATCTGG | |
| 118 | CCAGATGGATCGCTTCTCCGCC | D433R |

TABLE 3-continued

| SEQ ID NO | Sequence | Introduced mutation |
|---|---|---|
| 119 | GGCGGAGAAGCGATCCATCTGG | |
| 120 | CCAGATGGATAGCTTCTCCGCC | D433S |
| 121 | GGCGGAGAAGCTATCCATCTGG | |
| 122 | CCAGATGGATACCTTCTCCGCC | D433T |
| 123 | GGCGGAGAAGGTATCCATCTGG | |
| 124 | CCAGATGGATGTGTTCTCCGCC | D433V |
| 125 | GGCGGAGAACACATCCATCTGG | |
| 126 | CCAGATGGATTGGTTCTCCGCC | D433W |
| 127 | GGCGGAGAACCAATCCATCTGG | |
| 128 | CCAGATGGATTATTTCTCCGCC | D433Y |
| 129 | GGCGGAGAAATAATCCATCTGG | |
| 130 | GCAGCCCGCGGCGAAACTGGCACG | F174A |
| 131 | CGTGCCAGTTTCGCCGCGGGCTGC | |
| 132 | GCAGCCCGCGATTAAACTGGCACG | F174I |
| 133 | CGTGCCAGTTTAATCGCGGGCTGC | |
| 134 | GCAGCCCGCGCTGAAACTGGCACG | F174L |
| 135 | CGTGCCAGTTTCAGCGCGGGCTGC | |
| 136 | GCAGCCCGCGATGAAACTGGCACG | F174M |
| 137 | CGTGCCAGTTTCATCGCGGGCTGC | |

TABLE 4

| SEQ ID NO | Sequence | Introduced mutation |
|---|---|---|
| 138 | GCAGCCCGCGGTGAAACTGGCACG | F174V |
| 139 | CGTGCCAGTTTCACCGCGGGCTGC | |
| 140 | GCAGCCCGCGTGGAAACTGGCACG | F174W |
| 141 | CGTGCCAGTTTCCACGCGGGCTGC | |
| 142 | GCAGCCCGCGTATAAACTGGCACG | F174Y |
| 143 | CGTGCCAGTTTATACGCGGGCTGC | |
| 144 | GTGGTGAAAATTGGTAAAACCTG | D472I |
| 145 | CAGGTTTTACCAATTTTCACCAC | |
| 146 | CTATAAAGGCCGCATTGCGGAAC | T246R |
| 147 | GTTCCGCAATGCGGCCTTTATAG | |
| 148 | GATCCATATCCTGCAAATCCTCAATATTC | V301L |
| 149 | GAATATTGAGGATTTGCAGGATATGGATC | |
| 150 | GCTGAACACCAACTTCGGTACGG | T413N |
| 151 | CCGTACCGAAGTTGGTGTTCAGC | |
| 152 | GTAGCCCAGGCAGCAGCCGGATCATC | G484S |

TABLE 4-continued

| SEQ ID NO | Sequence | Introduced mutation |
|---|---|---|
| 153 | GATGATCCGGCTGCTGCCTGGGCTAC | |
| 154 | GTGATGCCAACAGCGTCGGGCCGAAC | A453S |
| 155 | GTTCGGCCCGACGCTGTTGGCATCAC | |
| 156 | CGTACCGAACGCGGAAGGGCTGG | V443A/Y444E |
| 157 | CCAGCCCTTCCGCGTTCGGTACG | |
| 158 | GCTGAACACCGCGTTCGGTACGG | T413A |
| 159 | CCGTACCGAACGCGGTGTTCAGC | |
| 160 | GCTGAACACCCATTTCGGTACGG | T413H |
| 161 | CCGTACCGAAATGGGTGTTCAGC | |
| 162 | GTAGCCCAGGCGCGAGCCGGATCATC | G484A |
| 163 | GATGATCCGGCTCGCGCCTGGGCTAC | |
| 164 | GTAGCCCAGGCGAAAGCCGGATCATC | G484E |
| 165 | GATGATCCGGCTTTCGCCTGGGCTAC | |
| 166 | GGTGTGGAGAAAGATGTCTTC | E38K |
| 167 | GAAGACATCTTTCTCCACACC | |
| 168 | CGATATGTTCGTGGATGATCAGG | L127V |
| 169 | CCTGATCATCCACGAACATATCG | |
| 170 | GGTGGTGAATTGCATCGATTATG | S498C |
| 171 | CATAATCGATGCAATTCACCACC | |
| 172 | GAAGCAAAAGGTCATAAAGTGGCGC | Q542H |
| 173 | GCGCCACTTTATGACCTTTTGCTTC | |
| 174 | GGTCGAACGCAACCCGATAAGCG | T276N |
| 175 | CGCTTATCGGGTTGCGTTCGACC | |
| 176 | CCGACCCGCGCAAAGTGGATGATTTAAC | S572K |
| 177 | GTTAAATCATCCACTTTGCGCGGGTCGG | |

TABLE 5

| SEQ ID NO | Sequence | Introduced mutation |
|---|---|---|
| 178 | CTATACGCTGCAGACCACCTTCG | N411Q |
| 179 | CGAAGGTGGTCTGCAGCGTATAG | |
| 180 | CCGGGCGTAGCGAACGTTGAAG | P441A/Y444E |
| 181 | CTTCAACGTTCGCTACGCCCGG | |
| 182 | GTACCGAACGAAGAAGGGCTGG | V443E/Y444E |
| 183 | CCAGCCCTTCTTCGTTCGGTAC | |
| 184 | GTACCGAACGGCGAAGGGCTGG | V443G/Y444E |
| 185 | CCAGCCCTTCGCCGTTCGGTAC | |
| 186 | GTACCGAACCTGGAAGGGCTGG | V443L/Y444E |
| 187 | CCAGCCCTTCCAGGTTCGGTAC | |

TABLE 5-continued

| SEQ ID NO | Sequence | Introduced mutation |
|---|---|---|
| 188 | GTACCGAACAACGAAGGGCTGG | V443N/Y444E |
| 189 | CAGCCCTTCGTTGTTCGGTAC | |
| 190 | GTACCGAACCAGGAAGGGCTGG | V443Q/Y444E |
| 191 | CCAGCCCTTCCTGGTTCGGTAC | |
| 192 | GTTGAAGGGCGGTGGGCGGTG | Y444E/L446A |
| 193 | CACCGCCCACCGCCCCTTCAAC | |
| 194 | GGTTGGGCCGAACGGTGAGTTGTAC | D561N |
| 195 | GTACAACTCACCGTTCGGCCCAACC | |
| 196 | GCCGCCGCGCATCCTGCGCCGCC | P27H |
| 197 | GGCGGCGCAGGATGCGCGGCGGC | |
| 198 | GTAATCAAACTTGCCATTACTCAGTG | T392C |
| 199 | CACTGAGTAATGGCAAGTTTGATTAC | |

Example 4

*Escherichia coli* Strains Deficient in Each Peptidase and Evaluation of Val-Gly Degradation Ability Thereof The JM109ΔpepA strain, JM109ΔpepB strain, JM109ΔpepD strain, JM109ΔpepE strain, and JM109ΔpepN strain were transformed with pUC18, respectively.

Each of the obtained transformants was cultured at 25° C. for 22 hours using the LB medium [1.0% (w/v) peptone, 0.5% (w/v) yeast extract, and 1.0% (w/v) NaCl] containing 100 mg/L of Amp. The cells in the obtained culture fluid were washed with a 0.2 M potassium phosphate buffer (pH 8.0), and a cell suspension was prepared with the same buffer. A reaction mixture containing 100 mM Val-Gly, 0.2 M potassium phosphate buffer (pH 8.0), and the cells was prepared. The cell density was such a density that the reaction mixture diluted 51 times showed an absorbance of 0.2 at 610 nm. When a metal salt was added to the reaction mixture, it was added at a final concentration of 0.1 mM. When ethylenediaminetetraacetic acid (EDTA) was added, it was added by using a 500 mM aqueous solution thereof produced by Nakarai Tesque (pH 8.0) at a final concentration of 1 mM. The reaction conditions were 20° C. and 20 hours, and Val-Gly was quantified by HPLC after completion of the reaction. The quantification conditions were as follows.

As the column, Synergi 4μ Hydro-RP 80A produced by Phenomenex (particle size: 4 microns, internal diameter: 4.6 mm, length: 250 mm) was used. As the eluent, Solution A (50 mM sodium dihydrogenphosphate, pH 2.5, pH was adjusted with phosphoric acid) and Solution B (1:1 mixture of Solution A and acetonitrile) were used. The column temperature was 40° C., and the detection UV wavelength was 210 nm. As the gradient of the eluent, used were 0 to 5% Solution B for 0 to 5 minutes, 5% Solution B for 5 to 15 minutes, 5 to 80% Solution B for 15 to 30 minutes, 80 to 0% Solution B for 30 to 30.1 minutes, and 0% Solution B for 30.1 to 50 minutes.

The results are shown in Table 6.

TABLE 6

| | Host bacterium strain | | | | | |
|---|---|---|---|---|---|---|
| | JM109 | JM109 | JM109 | JM109 | JM109 | JM109 |
| | | | Deficient gene | | | |
| | — | ΔpepA | ΔpepB | ΔpepD | ΔpepE | ΔpepN |
| | | | Harbored plasmid | | | |
| | pUC18 | pUC18 | pUC18 | pUC18 | pUC18 | pUC18 |
| No addition | 89.4 | 85.8 | 84.5 | 93.8 | 81.4 | 61.0 |
| 0.1 mM CoCl₂ | 0.0 | 0.0 | 0.0 | 86.8 | 0.0 | 0.0 |
| 0.1 mM MgCl₂ | 84.7 | 78.5 | 79.7 | 85.6 | 78.8 | 58.5 |
| 0.1 mM MnSO₄ | 0.0 | 0.0 | 0.0 | 85.7 | 0.0 | 0.0 |
| 0.1 mM NiSO₄ | 80.5 | 71.6 | 75.5 | 87.3 | 75.1 | 0.0 |
| 0.1 mM ZnSO₄ | 74.7 | 73.4 | 71.7 | 93.2 | 73.8 | 0.0 |
| 0.1 mM FeSO₄ | 0.0 | 0.0 | 0.0 | 90.3 | 0.0 | 0.0 |
| 1 mM EDTA | 94.0 | 91.9 | 91.2 | 91.3 | 90.1 | 90.1 |

As shown in Table 2, the cells of *Escherichia coli* wild-type strain decomposed Val-Gly in the presence of Co$^{2+}$, Mn$^{2+}$, or Fe$^{2+}$ ions. These results revealed that PepD mainly participates in the decomposition of Val-Gly. In addition, when these metal ions were not added, decomposition of Val-Gly was suppressed to some extent by addition of 1 mM EDTA.

Example 5

Evaluation of γ-glutamylation of Val-Gly by Mutant GGT Enzymes

The JM109ΔpepD strain was transformed with the plasmids described in Example 3. The transformants were cultured at 25° C. for 22 hours by using the TB medium [Terrific Broth, Molecular Cloning A Laboratory Manual, 3rd edition, Sambrook, J. et al., Cold Spring Harbor Laboratory Press (2001)] containing 100 mg/L of Amp. Each of the obtained culture fluids and an equivalent volume of a test solution (0.2 M L-glutamine, 0.2 M Val-Gly, pH of the test solution was adjusted to pH 7.6 with NaOH) were mixed to start the reaction. The reaction conditions were 20° C. and 4 hours, and γ-Glu-Val-Gly was quantified by HPLC after completion of the reaction. HPLC was performed under the same conditions as those of Example 4.

The results are shown in Tables 7 to 9.

TABLE 7

| Amino acid substitution | | | | γ-Glu-Val-Gly |
|---|---|---|---|---|
| 1 | 2 | 3 | 4 | (mM) |
| | | | | 4.8 |
| E38 | K | | | 5.8 |
| F174 | I | | | 4.8 |
| N411 | Q | | | 43.4 |
| T392 | C | | | 20.0 |
| T413 | N | | | 4.2 |
| T413 | H | | | 7.0 |
| Q430 | A | | | 5.3 |
| Q430 | C | | | 9.6 |
| Q430 | D | | | 11.7 |
| Q430 | E | | | 9.9 |
| Q430 | F | | | 8.2 |
| Q430 | G | | | 4.7 |
| Q430 | H | | | 9.6 |
| Q430 | I | | | 9.0 |
| Q430 | K | | | 9.2 |
| Q430 | L | | | 9.1 |
| Q430 | M | | | 40.8 |

TABLE 7-continued

| Amino acid substitution | | | | γ-Glu-Val-Gly |
|---|---|---|---|---|
| 1 | 2 | 3 | 4 | (mM) |
| Q430 N | | | | 6.8 |
| Q430 P | | | | 8.3 |
| Q430 R | | | | 1.3 |
| Q430 S | | | | 9.5 |
| Q430 T | | | | 4.6 |
| Q430 V | | | | 5.4 |
| Q430 W | | | | 3.8 |
| Q430 Y | | | | 14.6 |
| D433 A | | | | 10.8 |
| D433 C | | | | 0.3 |
| D433 E | | | | 38.6 |
| D433 F | | | | 0.1 |
| D433 G | | | | 19.0 |
| D433 H | | | | 0.2 |
| D433 I | | | | 0.1 |
| D433 K | | | | 0.1 |
| D433 L | | | | 0.1 |
| D433 M | | | | 0.3 |
| D433 N | | | | 5.7 |
| D433 P | | | | 0.2 |
| D433 Q | | | | 0.2 |
| D433 R | | | | 0.1 |
| D433 S | | | | 5.6 |
| D433 T | | | | 0.2 |
| D433 V | | | | 0.1 |
| D433 W | | | | 0.1 |

TABLE 8

| Amino acid substitution | | | | γ-Glu-Val-Gly |
|---|---|---|---|---|
| 1 | 2 | 3 | 4 | (mM) |
| D433 Y | | | | 0.2 |
| Y444 A | | | | 52.5 |
| Y444 D | | | | 62.4 |
| Y444 E | | | | 63.3 |
| S572 K | | | | 25.9 |
| G484 E | | | | 6.9 |
| G484 S | | | | 47.9 |
| E38 K | Y444 E | | | 65.3 |
| F174 A | Y444 E | | | 61.9 |
| F174 I | Y444 E | | | 62.6 |
| F174 L | Y444 E | | | 64.8 |
| F174 M | Y444 E | | | 65.2 |
| F174 V | Y444 E | | | 66.6 |
| F174 W | Y444 E | | | 62.8 |
| F174 Y | Y444 E | | | 65.2 |
| T246 R | Y444 E | | | 66.0 |
| V301 L | Y444 E | | | 66.1 |
| T392 C | Y444 A | | | 54.0 |
| T392 C | Y444 E | | | 19.9 |
| N411 Q | Q430 N | | | 21.3 |
| N411 Q | D433 E | | | 0.0 |
| N411 Q | S572 K | | | 40.9 |
| T413 N | Q430 N | | | 4.1 |
| T413 N | G484 E | | | 17.1 |
| T413 N | G484 S | | | 22.4 |
| T413 N | S572 K | | | 4.4 |
| T413 A | Y444 E | | | 64.0 |
| T413 H | Y444 E | | | 70.8 |
| T413 N | Y444 E | | | 65.4 |
| Q430 N | Y444 A | | | 53.6 |
| Q430 N | Y444 E | | | 63.2 |
| Q430 N | Y444 D | | | 64.7 |
| Q430 N | Y444 N | | | 61.9 |
| D433 E | Y444 A | | | 9.3 |
| D433 E | Y444 E | | | 8.5 |
| P441 A | Y444 E | | | 63.1 |
| V443 A | Y444 E | | | 68.4 |
| V443 E | Y444 E | | | 60.8 |
| V443 G | Y444 E | | | 67.4 |
| V443 L | Y444 E | | | 61.3 |

TABLE 8-continued

| Amino acid substitution | | | | γ-Glu-Val-Gly |
|---|---|---|---|---|
| 1 | 2 | 3 | 4 | (mM) |
| V443 N | Y444 E | | | 60.8 |
| V443 Q | Y444 E | | | 64.4 |
| Y444 E | L446 A | | | 64.5 |
| Y444 E | A453 S | | | 64.2 |
| Y444 E | D472 I | | | 64.1 |

TABLE 9

| Amino acid substitution | | | | γ-Glu-Val-Gly |
|---|---|---|---|---|
| 1 | 2 | 3 | 4 | (mM) |
| Y444 E | G484 A | | | 65.5 |
| Y444 E | G484 S | | | 60.1 |
| Y444 E | S498 C | | | 66.7 |
| Y444 E | Q542 H | | | 66.1 |
| Y444 E | D561 N | | | 65.4 |
| P27 H | T413 N | Y444 E | | 64.9 |
| P27 H | Y444 E | G484 S | | 62.1 |
| E38 K | T413 N | Y444 E | | 62.6 |
| L127 V | T413 N | Y444 E | | 62.8 |
| T276 N | T413 N | Y444 E | | 63.1 |
| T276 N | Y444 E | G484 S | | 64.5 |
| T413 H | Y444 E | G484 S | | 66.5 |
| T413 N | Q430 N | Y444 E | | 65.8 |
| T413 N | V443 A | Y444 E | | 62.8 |
| T413 N | Y444 E | A453 S | | 62.6 |
| T413 N | Y444 E | S498 C | | 62.6 |
| T413 N | Y444 E | Q542 H | | 64.0 |
| T413 N | Y444 E | G484 S | | 60.3 |
| V443 A | Y444 E | G484 S | | 65.0 |
| Y444 E | G484 S | Q542 H | | 63.4 |
| T413 N | V443 A | Y444 E | G484 S | 62.4 |
| T413 N | Y444 E | A453 S | G484 S | 61.2 |
| T413 N | Y444 E | G484 S | Q542 H | 61.3 |
| T413 N | Y444 E | G484 S | S572 K | 62.1 |
| T413 N | Y444 E | G484 S | S498 C | 60.8 |
| T413 N | Q430 N | Y444 E | G484 S | 69.9 |
| T413 N | Y444 E | G484 E | S498 C | 60.8 |

Example 6

Evaluation of γ-Glutamylation of Val-Gly by Mutant GGT Enzyme-Expressing Strains Prepared by Using *Escherichia coli* Strains Deficient in Each Peptidase as Host The *Escherichia coli* JM109 strain, JM109ΔpepA strain, JM109ΔpepB strain, JM109ΔpepD strain, JM109ΔpepE strain, and JM109ΔpepN strain were transformed with pUC18, pSF12-ggt, or pSF12-ggt (Y444E) to obtain transformants. Each of the obtained transformants was cultured at 25° C. for 20 hours using the LB medium [1.0% (w/v) peptone, 0.5% (w/v) yeast extract, and 1.0% (w/v) NaCl] containing 100 mg/L of Amp. The obtained culture fluid was centrifuged to separate the culture fluid into wet cells and supernatant, and the wet cells were suspended in the supernatant to prepare a cell suspension so that the suspension diluted 51 times had an absorbance of 0.4 at 610 nm. This cell suspension and an equivalent volume of a test solution (0.2 M potassium phosphate buffer (pH 8.0), 0.2 M L-glutamine, 0.2 M Val-Gly) were mixed to start the reaction. The reaction conditions were 20° C. and 20 hours, and γ-Glu-Val-Gly and Val-Gly were quantified by HPLC after completion of the reaction under the same conditions as those of Example 4. The results are shown in Table 10.

TABLE 10

| Strain | | Harbored plasmid | Val-Gly (mM) | γ-Glu-Val-Gly (mM) |
|---|---|---|---|---|
| JM109 | | pSF12-ggt | 59.2 | 1.8 |
| JM109 | ΔpepA | pSF12-ggt | 62.8 | 1.8 |
| JM109 | ΔpepB | pSF12-ggt | 59.6 | 1.9 |
| JM109 | ΔpepD | pSF12-ggt | 85.1 | 2.9 |
| JM109 | ΔpepE | pSF12-ggt | 59.3 | 1.7 |
| JM109 | ΔpepN | pSF12-ggt | 60.7 | 2.1 |
| JM109 | | pSF12-ggt (Y444E) | 38.4 | 34.5 |
| JM109 | ΔpepA | pSF12-ggt (Y444E) | 42.7 | 33.3 |
| JM109 | ΔpepB | pSF12-ggt (Y444E) | 39.4 | 31.0 |
| JM109 | ΔpepD | pSF12-ggt (Y444E) | 48.3 | 36.1 |
| JM109 | ΔpepE | pSF12-ggt (Y444E) | 36.7 | 31.2 |
| JM109 | ΔpepN | pSF12-ggt (Y444E) | 38.3 | 30.6 |

Explanation of Sequence Listing
SEQ ID NO: 1: Nucleotide sequence of *Escherichia coli* ggt gene
SEQ ID NO: 2: Amino acid sequence of *Escherichia coli* GGT
SEQ ID NO: 3: Amino acid sequence of *Shigella flexneri flexneri* 5 str. 8401 GGT
SEQ ID NO: 4: Amino acid sequence of *Shigella dysenteriae* Sd197 GGT
SEQ ID NO: 5: Amino acid sequence of *Shigella boydii* strain Sb227 GGT
SEQ ID NO: 6: Amino acid sequence of *Salmonella Typhimurium* ATCC 700720 GGT
SEQ ID NO: 7: Amino acid sequence of *Salmonella enterica enterica choleraesuis* strain SC-B67 GGT
SEQ ID NO: 8: Amino acid sequence of *Salmonella enterica typhi* strain Ty2 GGT
SEQ ID NO: 9: Amino acid sequence of *Klebsiella pneumoniae* ATCC 202080 GGT
SEQ ID NO: 10: Amino acid sequence of *Salmonella enterica* subsp. *enterica* serovar A str. ATCC 9150 Paratyphi GGT
SEQ ID NO: 11: Amino acid sequence of *Klebsiella pneumoniae* clone KPN308894 GGT
SEQ ID NO: 12: Amino acid sequence of *Enterobacter cloaceae* clone EBC103795 GGT
SEQ ID NO: 13: Consensus sequence of various GGT small subunits
SEQ ID NO: 14: Nucleotide sequence of *Escherichia coli* pepD gene
SEQ ID NO: 15: Amino acid sequence of *Escherichia coli* PepD
SEQ ID NO: 16: Nucleotide sequence of *Escherichia coli* pepA gene
SEQ ID NO: 17: Amino acid sequence of *Escherichia coli* PepA
SEQ ID NO: 18: Nucleotide sequence of *Escherichia coli* pepB gene
SEQ ID NO: 19: Amino acid sequence of *Escherichia coli* PepB
SEQ ID NO: 20: Nucleotide sequence of *Escherichia coli* pepE gene
SEQ ID NO: 21: Amino acid sequence of *Escherichia coli* PepE
SEQ ID NO: 22: Nucleotide sequence of *Escherichia coli* pepN gene
SEQ ID NO: 23: Amino acid sequence of *Escherichia coli* PepN
SEQ ID NOS: 24 to 31: PCR primers for preparation of pSF12_ggt
SEQ ID NOS: 32 to 45: PCR primers for disruption of various peptidase genes
SEQ ID NOS: 46 to 199: PCR primers for introduction of mutation

INDUSTRIAL APPLICABILITY

The mutant GGT of the present invention has a high activity for catalyzing γ-glutamylation of Val-Gly. Therefore, according to the method for producing γ-Glu-Val-Gly using the mutant GGT of the present invention, γ-Glu-Val-Gly can be efficiently produced by using Val-Gly as a raw material.

What is claimed is:

1. A method for producing γ-Glu-Val-Gly comprising reacting Val-Gly with a γ-glutamyl group donor in the presence of a γ-glutamyltransferase such that γ-Glu-Val-Gly is generated, wherein the γ-glutamyltransferase comprises a large subunit and a small subunit, wherein the large subunit has an amino acid sequence having no less than 90% identity to the amino acid sequence of the positions 26 to 390 of the amino acid sequence of SEQ ID NO: 2, wherein the glutamic acid at the position corresponding to position 38 of SEQ ID NO: 2 is modified by a substitution, wherein the small subunit has an amino acid sequence having no less than 90% sequence identity to the amino acid sequence of the positions 391 to 580 of the amino acid sequence of SEQ ID NO: 2, and wherein the tyrosine at the position corresponding to position 444 of SEQ ID NO: 2 is modified by a substitution.

2. The method according to claim 1, wherein the tyrosine at the position corresponding to position 444 of SEQ ID NO: 2 is substituted with aspartic acid, glutamic acid, asparagine, or alanine.

3. The method according to claim 1, wherein the small subunit has an amino acid substitution corresponding to a substitution in SEQ ID NO: 2 selected from the group consisting of Y444D, Y444E, Y444A, (T413A+Y444E), (T413H+Y444E), (T413N+Y444E), (Q430N+Y444E), (Q430N+Y444D), (Q430N+Y444N), (P441A+Y444E), (V443A+Y444E), (V443E+Y444E), (V443G+Y444E), (V443L+Y444E), (V443N+Y444E), (V443Q+Y444E), (Y444E+L446A), (Y444E+A453S), (Y444E+D472I), (Y444E+G484A), (Y444E+G484S), (Y444E+S498C), (Y444E+Q542H), (Y444E+D561N), (T413N+Y444E+V443A), (T413N+Y444E+A453S), (T413N+Y444E+S498C), (T413N+Y444E+Q542H), (G484S+Y444E+V443A), (G484S+Y444E+Q542H), (Q430N+Y444E+T413N), (T413H+Y444E+G484S), (T413N+Y444E+G484S), (T413N+Y444E+G484S+V443A), (T413N+Y444E+G484S+A453S), (T413N+Y444E+G484S+Q542H), (T413N+Y444E+G484S+S572K), (T413N+Y444E+G484S+Q430N), and (T413N+Y444E+G484E+S498C).

4. The method according to claim 1, wherein the glutamic acid at the position corresponding to position 38 of SEQ ID NO: 2 is substituted with lysine.

5. The method according to claim 1, wherein the small subunit has the amino acid sequence of SEQ ID NO: 13 except that the tyrosine at the position 54 of SEQ ID NO: 13 corresponding to position 444 of SEQ ID NO: 2 is modified by a substitution.

6. The method according to claim 1, wherein the small subunit has the amino acid sequence of
the positions 391 to 580 of SEQ ID NO: 2 except that the tyrosine at the position 444 of SEQ ID NO: 2 is substituted with aspartic acid, glutamic acid, asparagine, or alanine,
the positions 391 to 580 of SEQ ID NO: 3 except that the tyrosine at the position 444 of SEQ ID NO: 3 corresponding to the position 444 of SEQ ID NO: 2 is substituted with aspartic acid, glutamic acid, asparagine, or alanine,
the positions 392 to 581 of SEQ ID NO: 4 except that the tyrosine at the position 445 of SEQ ID NO: 4 corresponding to the position 444 of SEQ ID NO: 2 is substituted with aspartic acid, glutamic acid, asparagine, or alanine,
the positions 388 to 577 of SEQ ID NO: 5 except that the tyrosine at the position 441 of SEQ ID NO: 5 corresponding to the position 444 of SEQ ID NO: 2 is substituted with aspartic acid, glutamic acid, asparagine, or alanine,
the positions 391 to 580 of SEQ ID NO: 6 except that the tyrosine at the position 444 of SEQ ID NO: 6 corresponding to the position 444 of SEQ ID NO: 2 is substituted with aspartic acid, glutamic acid, asparagine, or alanine,
the positions 391 to 580 of SEQ ID NO: 7 except that the tyrosine at the position 444 of SEQ ID NO: 7 corresponding to the position 444 of SEQ ID NO: 2 is substituted with aspartic acid, glutamic acid, asparagine, or alanine,
the positions 391 to 580 of SEQ ID NO: 8 except that the tyrosine at the position 444 of SEQ ID NO: 8 corresponding to the position 444 of SEQ ID NO: 2 is substituted with aspartic acid, glutamic acid, asparagine, or alanine,
the positions 400 to 589 of SEQ ID NO: 9 except that the tyrosine at the position 453 of SEQ ID NO: 9 corresponding to the position 444 of SEQ ID NO: 2 is substituted with aspartic acid, glutamic acid, asparagine, or alanine,
the positions 391 to 580 of SEQ ID NO: 10 except that the tyrosine at the position 444 of SEQ ID NO: 10 corresponding to the position 444 of SEQ ID NO: 2 is substituted with aspartic acid, glutamic acid, asparagine, or alanine,
the positions 392 to 581 of SEQ ID NO: 11 except that the tyrosine at the position 445 of SEQ ID NO: 11 corresponding to the position 444 of SEQ ID NO: 2 is substituted with aspartic acid, glutamic acid, asparagine, or alanine, or
the positions 392 to 581 of SEQ ID NO: 12 except that the tyrosine at the position 445 of SEQ ID NO: 12 corresponding to the position 444 of SEQ ID NO: 2 is substituted with aspartic acid, glutamic acid, asparagine, or alanine.

7. The method according to claim 1, wherein the large subunit has the amino acid sequence of:
the positions 26 to 390 of SEQ ID NO: 2 except that the glutamic acid at the position 38 of SEQ ID NO: 2 is substituted with lysine,
the positions 26 to 390 of SEQ ID NO: 3 except that the glutamic acid at the position 38 of SEQ ID NO: 3 corresponding to the position 38 of SEQ ID NO: 2 is substituted with lysine,
the positions 26 to 391 of SEQ ID NO: 4 except that the glutamic acid at the position 39 of SEQ ID NO: 4 corresponding to the position 38 of SEQ ID NO: 2 is substituted with lysine,
the positions 26 to 387 of SEQ ID NO: 5 except that the glutamic acid at the position 35 of SEQ ID NO: 5 corresponding to the position 38 of SEQ ID NO: 2 is substituted with lysine,
the positions 25 to 390 of SEQ ID NO: 6 except that the glutamic acid at the position 38 of SEQ ID NO: 6 corresponding to the position 38 of SEQ ID NO: 2 is substituted with lysine,
the positions 25 to 390 of SEQ ID NO: 7 except that the glutamic acid at the position 38 of SEQ ID NO: 7 corresponding to the position 38 of SEQ ID NO: 2 is substituted with lysine,
the positions 25 to 390 of SEQ ID NO: 8 except that the glutamic acid at the position 38 of SEQ ID NO: 8 corresponding to the position 38 of SEQ ID NO: 2 is substituted with lysine, or
the positions 25 to 390 of SEQ ID NO: 10 except that the glutamic acid at the position 38 of SEQ ID NO: 10 corresponding to the position 38 of SEQ ID NO: 2 is substituted with lysine.

8. The method according to claim 1, wherein the γ-glutamyl group donor comprises L-glutamine or a salt thereof.

9. The method according to claim 1, wherein the reacting of Val-Gly with the γ-glutamyl group donor occurs in the presence of a microorganism containing the γ-glutamyltransferase, and the microorganism containing the γ-glutamyltransferase is a bacterium belonging to the family Enterobacteriaceae.

10. The method according to claim 9, wherein the microorganism containing the γ-glutamyltransferase is an *Escherichia* bacterium.

11. The method according to claim 10, wherein the microorganism containing the γ-glutamyltransferase is *Escherichia coli*.

12. The method according to claim 9, wherein the microorganism containing the γ-glutamyltransferase is deficient in peptidase D.

13. The method according to claim 1, wherein the reacting of Val-Gly with the γ-glutamyl group donor occurs in the presence of a metal chelating agent.

14. The method according to claim 1, wherein the reacting of Val-Gly with the γ-glutamyl group donor occurs in the presence of a microorganism containing the γ-glutamyltransferase or in the presence of a processed product of the microorganism, and the processed product of the microorganism has the γ-glutamyltransferase and is selected from the group consistent of the disrupted microorganism, an extract of the microorganism, a partially purified product of the microorganism, the purified γ-glutamyltransferase, the microorganism immobilized in acrylamide or carrageenan, and the γ-glutamyltransferase immobilized on a solid phase.

15. The method according to claim 1, wherein the small subunit has the amino acid sequence of SEQ ID NO: 13 except that the tyrosine at the position 54 of SEQ ID NO: 13 corresponding to the position 444 of SEQ ID NO: 2 is substituted with aspartic acid, glutamic acid, asparagine, or alanine.

16. The method according to claim 2, wherein the glutamic acid at the position corresponding to position 38 of SEQ ID NO: 2 is substituted with lysine.

17. The method according to claim 3, wherein the glutamic acid at the position corresponding to position 38 of SEQ ID NO: 2 is substituted with lysine.

18. The method according to claim 1, wherein the small subunit has the amino acid sequence of the positions 391 to 580 of SEQ ID NO: 3 except that the tyrosine at the position 444 of SEQ ID NO: 3 corresponding to position 444 of SEQ ID NO: 2 is modified by a substitution, the positions 392 to 581 of SEQ ID NO: 4 except that the tyrosine at the position 445 of SEQ ID NO: 4 corresponding to position 444 of SEQ ID NO: 2 is modified by a substitution, the positions 388 to 577 of SEQ ID NO: 5 except that the tyrosine at the position 441 of SEQ ID NO: 5 corresponding to position 444 of SEQ ID NO: 2 is modified by a substitution, the positions 391 to 580 of SEQ ID NO: 6 except that the tyrosine at the position 444 of SEQ ID NO: 6 corresponding to position 444 of SEQ ID NO: 2 is modified by a substitution, the positions 391 to 580 of SEQ ID NO: 7 except that the tyrosine at the position 444 of SEQ ID NO: 7 corresponding to position 444 of SEQ ID NO: 2 is modified by a substitution, the positions 391 to 580 of SEQ ID NO: 8 except that the tyrosine at the position 444 of SEQ ID NO: 8 corresponding to position 444 of SEQ ID NO: 2 is modified by a substitution, the positions 400 to 589 of SEQ ID NO: 9 except that the tyrosine at the position 453 of SEQ ID NO: 9 corresponding to position 444 of SEQ ID NO: 2 is modified by a substitution, the positions 391 to 580 of SEQ ID NO: 10 except that the tyrosine at the position 444 of SEQ ID NO: 10 corresponding to position 444 of SEQ ID NO: 2 is modified by a substitution, the positions 392 to 581 of SEQ ID NO: 11 except that the tyrosine at the position 445 of SEQ ID NO: 11 corresponding to position 444 of SEQ ID NO: 2 is modified by a substitution, or the positions 392 to 581 of SEQ ID NO: 12 except that the tyrosine at the position 445 of SEQ ID NO: 12 corresponding to position 444 of SEQ ID NO: 2 is modified by a substitution.

19. The method according to claim 1, wherein the large subunit has the amino acid sequence of:

the positions 26 to 390 of SEQ ID NO: 3 except that the glutamic acid at the position 38 of SEQ ID NO: 3 corresponding to the position 38 of SEQ ID NO: 2 is modified by a substitution, the positions 26 to 391 of SEQ ID NO: 4 except that the glutamic acid at the position 39 of SEQ ID NO: 4 corresponding to the position 38 of SEQ ID NO: 2 is modified by a substitution, the positions 26 to 387 of SEQ ID NO: 5 except that the glutamic acid at the position 35 of SEQ ID NO: 5 corresponding to the position 38 of SEQ ID NO: 2 is modified by a substitution, the positions 25 to 390 of SEQ ID NO: 6 except that the glutamic acid at the position 38 of SEQ ID NO: 6 corresponding to the position 38 of SEQ ID NO: 2 is modified by a substitution, the positions 25 to 390 of SEQ ID NO: 7 except that the glutamic acid at the position 38 of SEQ ID NO: 7 corresponding to the position 38 of SEQ ID NO: 2 is modified by a substitution, the positions 25 to 390 of SEQ ID NO: 8 except that the glutamic acid at the position 38 of SEQ ID NO: 8 corresponding to the position 38 of SEQ ID NO: 2 is modified by a substitution, or the positions 25 to 390 of SEQ ID NO: 10 except that the glutamic acid at the position 38 of SEQ ID NO: 10 corresponding to the position 38 of SEQ ID NO: 2 is modified by a substitution.

\* \* \* \* \*

SEQUENCE LISTING

```
<160> NUMBER OF SEQ ID NOS: 199

<210> SEQ ID NO 1
<211> LENGTH: 1743
<212> TYPE: DNA
<213> ORGANISM: Escherichia coli
<220> FEATURE:
<221> NAME/KEY: CDS
<222> LOCATION: (1)..(1743)

<400> SEQUENCE: 1 atg ata aaa ccg acg ttt tta cgc cgg gtg gcc att gct gct ctg ctc      48
Met Ile Lys Pro Thr Phe Leu Arg Arg Val Ala Ile Ala Ala Leu Leu
1               5                   10                  15 tca gga agt tgt ttt agc gcc gcc gcc gcg cct cct gcg ccg ccc gtc      96
Ser Gly Ser Cys Phe Ser Ala Ala Ala Ala Pro Pro Ala Pro Pro Val
                20                  25                  30 tcg tat ggt gtg gag gaa gat gtc ttc cac ccg gta cgc gcg aaa cag     144
Ser Tyr Gly Val Glu Glu Asp Val Phe His Pro Val Arg Ala Lys Gln
            35                  40                  45 gga atg gta gcg tct gtg gac gcc act gcc act cag gtg ggg gtg gat     192
Gly Met Val Ala Ser Val Asp Ala Thr Ala Thr Gln Val Gly Val Asp
        50                  55                  60
```

-continued

```
att ctc aag gag ggc ggg aat gcc gtt gat gcc gcc gtg gcg gtg ggc       240
Ile Leu Lys Glu Gly Gly Asn Ala Val Asp Ala Ala Val Ala Val Gly
 65              70                  75                  80 tac gcg ctg gcg gta acg cat ccg cag gca ggg aat ctg ggc ggt ggt       288
Tyr Ala Leu Ala Val Thr His Pro Gln Ala Gly Asn Leu Gly Gly Gly
                 85                  90                  95 ggt ttt atg tta atc cgc tcg aaa aat ggc aat acc acg gct atc gat       336
Gly Phe Met Leu Ile Arg Ser Lys Asn Gly Asn Thr Thr Ala Ile Asp
            100                 105                 110 ttc cgc gaa atg gca ccc gcc aaa gcg acc cgc gat atg ttc ctc gat       384
Phe Arg Glu Met Ala Pro Ala Lys Ala Thr Arg Asp Met Phe Leu Asp
        115                 120                 125 gat cag ggc aac ccg gac agc aaa aaa tca ctc act tcg cat ctg gct       432
Asp Gln Gly Asn Pro Asp Ser Lys Lys Ser Leu Thr Ser His Leu Ala
    130                 135                 140 tcc ggc aca ccg ggt acg gta gca ggt ttc tcg ctg gcg ctg gat aaa       480
Ser Gly Thr Pro Gly Thr Val Ala Gly Phe Ser Leu Ala Leu Asp Lys
145                 150                 155                 160 tac ggc acc atg ccg ctg aac aaa gtc gtg cag ccc gcg ttt aaa ctg       528
Tyr Gly Thr Met Pro Leu Asn Lys Val Val Gln Pro Ala Phe Lys Leu
                165                 170                 175 gca cgc gat ggt ttt atc gtt aac gac gcg ctg gct gac gat ctc aaa       576
Ala Arg Asp Gly Phe Ile Val Asn Asp Ala Leu Ala Asp Asp Leu Lys
            180                 185                 190 acc tac ggt agc gaa gtg ttg ccg aat cac gaa aac agt aaa gct atc       624
Thr Tyr Gly Ser Glu Val Leu Pro Asn His Glu Asn Ser Lys Ala Ile
        195                 200                 205 ttc tgg aaa gag ggc gag ccg ctg aaa aag ggc gac acg ctg gtg cag       672
Phe Trp Lys Glu Gly Glu Pro Leu Lys Lys Gly Asp Thr Leu Val Gln
    210                 215                 220 gcg aac ctg gca aag agc ctg gag atg att gct gaa aac ggc ccg gac       720
Ala Asn Leu Ala Lys Ser Leu Glu Met Ile Ala Glu Asn Gly Pro Asp
225                 230                 235                 240 gaa ttc tat aaa ggc acg att gcg gaa cag atc gcc cag gag atg cag       768
Glu Phe Tyr Lys Gly Thr Ile Ala Glu Gln Ile Ala Gln Glu Met Gln
                245                 250                 255 aaa aac ggt ggc ttg atc act aaa gaa gat tta gca gcc tat aaa gcg       816
Lys Asn Gly Gly Leu Ile Thr Lys Glu Asp Leu Ala Ala Tyr Lys Ala
            260                 265                 270 gtc gaa cgc act ccg ata agc ggc gat tat cgc ggg tat cag gtt tac       864
Val Glu Arg Thr Pro Ile Ser Gly Asp Tyr Arg Gly Tyr Gln Val Tyr
        275                 280                 285 tcc atg cca ccg cca tcc tcc ggc ggg atc cat atc gta caa atc ctc       912
Ser Met Pro Pro Pro Ser Ser Gly Gly Ile His Ile Val Gln Ile Leu
    290                 295                 300 aat att ctg gaa aac ttc gat atg aag aaa tac ggc ttt ggc agc gcc       960
Asn Ile Leu Glu Asn Phe Asp Met Lys Lys Tyr Gly Phe Gly Ser Ala
305                 310                 315                 320 gat gcg atg caa atc atg gca gaa gcg gag aaa tac gcc tac gcc gac      1008
Asp Ala Met Gln Ile Met Ala Glu Ala Glu Lys Tyr Ala Tyr Ala Asp
                325                 330                 335 cgc tcg gaa tat ctt ggc gac ccg gat ttt gtc aaa gta ccg tgg cag      1056
Arg Ser Glu Tyr Leu Gly Asp Pro Asp Phe Val Lys Val Pro Trp Gln
            340                 345                 350 gcg ctg acc aat aaa gcc tat gcc aaa tct att gcc gat caa att gat      1104
Ala Leu Thr Asn Lys Ala Tyr Ala Lys Ser Ile Ala Asp Gln Ile Asp
        355                 360                 365 atc aat aaa gcg aag cca tcc agc gaa att cgc ccc ggc aag ctt gcg      1152
Ile Asn Lys Ala Lys Pro Ser Ser Glu Ile Arg Pro Gly Lys Leu Ala
    370                 375                 380
```

```
cct tat gag agt aat caa act acc cat tac tca gtg gtg gat aaa gat    1200
Pro Tyr Glu Ser Asn Gln Thr Thr His Tyr Ser Val Val Asp Lys Asp
385                 390                 395                 400 ggt aac gcg gtg gcg gtg acc tat acg ctg aac acc acc ttc ggt acg    1248
Gly Asn Ala Val Ala Val Thr Tyr Thr Leu Asn Thr Thr Phe Gly Thr
            405                 410                 415 ggc att gtc gcg ggc gag agc ggt att ctg ctt aat aac cag atg gat    1296
Gly Ile Val Ala Gly Glu Ser Gly Ile Leu Leu Asn Asn Gln Met Asp
420                 425                 430 gat ttc tcc gcc aaa ccg ggc gta ccg aac gtt tac ggg ctg gtg ggc    1344
Asp Phe Ser Ala Lys Pro Gly Val Pro Asn Val Tyr Gly Leu Val Gly
            435                 440                 445 ggt gat gcc aac gcc gtc ggg ccg aac aaa cgc ccg ctg tcg tcg atg    1392
Gly Asp Ala Asn Ala Val Gly Pro Asn Lys Arg Pro Leu Ser Ser Met
450                 455                 460 tcg ccg acc att gtg gtg aaa gac ggt aaa acc tgg ctg gtt acc ggt    1440
Ser Pro Thr Ile Val Val Lys Asp Gly Lys Thr Trp Leu Val Thr Gly
465                 470                 475                 480 agc cca ggc ggt agc cgg atc atc act aca gtg ctg caa atg gtg gtg    1488
Ser Pro Gly Gly Ser Arg Ile Ile Thr Thr Val Leu Gln Met Val Val
            485                 490                 495 aat agc atc gat tat ggc ttg aac gtc gcc gaa gcg acc aat gcg ccg    1536
Asn Ser Ile Asp Tyr Gly Leu Asn Val Ala Glu Ala Thr Asn Ala Pro
500                 505                 510 cgt ttc cac cat cag tgg ttg ccg gac gag ctg cgt gtc gaa aaa ggg    1584
Arg Phe His His Gln Trp Leu Pro Asp Glu Leu Arg Val Glu Lys Gly
            515                 520                 525 ttt agc ccg gat acg ctc aag ctg ctg gaa gca aaa ggt cag aaa gtg    1632
Phe Ser Pro Asp Thr Leu Lys Leu Leu Glu Ala Lys Gly Gln Lys Val
530                 535                 540 gcg ctg aaa gag gcg atg ggc agt aca caa agc att atg gtt ggg ccg    1680
Ala Leu Lys Glu Ala Met Gly Ser Thr Gln Ser Ile Met Val Gly Pro
545                 550                 555                 560 gac ggt gag ttg tac ggc gca tcc gac ccg cgc tcg gtg gat gat tta    1728
Asp Gly Glu Leu Tyr Gly Ala Ser Asp Pro Arg Ser Val Asp Asp Leu
            565                 570                 575 acg gcg ggg tac taa                                                1743
Thr Ala Gly Tyr
            580

<210> SEQ ID NO 2
<211> LENGTH: 580
<212> TYPE: PRT
<213> ORGANISM: Escherichia coli

<400> SEQUENCE: 2

Met Ile Lys Pro Thr Phe Leu Arg Arg Val Ala Ile Ala Ala Leu Leu
1               5                   10                  15

Ser Gly Ser Cys Phe Ser Ala Ala Ala Pro Pro Ala Pro Pro Val
            20                  25                  30

Ser Tyr Gly Val Glu Glu Asp Val Phe His Pro Val Arg Ala Lys Gln
        35                  40                  45

Gly Met Val Ala Ser Val Asp Ala Thr Ala Thr Gln Val Gly Val Asp
    50                  55                  60

Ile Leu Lys Glu Gly Gly Asn Ala Val Asp Ala Ala Val Ala Val Gly
65                  70                  75                  80

Tyr Ala Leu Ala Val Thr His Pro Gln Ala Gly Asn Leu Gly Gly Gly
                85                  90                  95
```

-continued

```
Gly Phe Met Leu Ile Arg Ser Lys Asn Gly Asn Thr Thr Ala Ile Asp
            100                 105                 110

Phe Arg Glu Met Ala Pro Ala Lys Ala Thr Arg Asp Met Phe Leu Asp
        115                 120                 125

Asp Gln Gly Asn Pro Asp Ser Lys Lys Ser Leu Thr Ser His Leu Ala
    130                 135                 140

Ser Gly Thr Pro Gly Thr Val Ala Gly Phe Ser Leu Ala Leu Asp Lys
145                 150                 155                 160

Tyr Gly Thr Met Pro Leu Asn Lys Val Val Gln Pro Ala Phe Lys Leu
                165                 170                 175

Ala Arg Asp Gly Phe Ile Val Asn Asp Ala Leu Ala Asp Asp Leu Lys
            180                 185                 190

Thr Tyr Gly Ser Glu Val Leu Pro Asn His Glu Asn Ser Lys Ala Ile
        195                 200                 205

Phe Trp Lys Glu Gly Glu Pro Leu Lys Lys Gly Asp Thr Leu Val Gln
    210                 215                 220

Ala Asn Leu Ala Lys Ser Leu Glu Met Ile Ala Glu Asn Gly Pro Asp
225                 230                 235                 240

Glu Phe Tyr Lys Gly Thr Ile Ala Glu Gln Ile Ala Gln Glu Met Gln
                245                 250                 255

Lys Asn Gly Gly Leu Ile Thr Lys Glu Asp Leu Ala Ala Tyr Lys Ala
            260                 265                 270

Val Glu Arg Thr Pro Ile Ser Gly Asp Tyr Arg Gly Tyr Gln Val Tyr
        275                 280                 285

Ser Met Pro Pro Pro Ser Ser Gly Gly Ile His Ile Val Gln Ile Leu
    290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                325                 330                 335

Arg Ser Glu Tyr Leu Gly Asp Pro Asp Phe Val Lys Val Pro Trp Gln
            340                 345                 350

Ala Leu Thr Asn Lys Ala Tyr Ala Lys Ser Ile Ala Asp Gln Ile Asp
        355                 360                 365

Ile Asn Lys Ala Lys Pro Ser Ser Glu Ile Arg Pro Gly Lys Leu Ala
    370                 375                 380

Pro Tyr Glu Ser Asn Gln Thr Thr His Tyr Ser Val Val Asp Lys Asp
385                 390                 395                 400

Gly Asn Ala Val Ala Val Thr Tyr Thr Leu Asn Thr Thr Phe Gly Thr
                405                 410                 415

Gly Ile Val Ala Gly Glu Ser Gly Ile Leu Leu Asn Asn Gln Met Asp
            420                 425                 430

Asp Phe Ser Ala Lys Pro Gly Val Pro Asn Val Tyr Gly Leu Val Gly
        435                 440                 445

Gly Asp Ala Asn Ala Val Gly Pro Asn Lys Arg Pro Leu Ser Ser Met
    450                 455                 460

Ser Pro Thr Ile Val Val Lys Asp Gly Lys Thr Trp Leu Val Thr Gly
465                 470                 475                 480

Ser Pro Gly Gly Ser Arg Ile Ile Thr Thr Val Leu Gln Met Val Val
                485                 490                 495

Asn Ser Ile Asp Tyr Gly Leu Asn Val Ala Glu Ala Thr Asn Ala Pro
            500                 505                 510

Arg Phe His His Gln Trp Leu Pro Asp Glu Leu Arg Val Glu Lys Gly
```

```
            515                 520                 525
Phe Ser Pro Asp Thr Leu Lys Leu Leu Glu Ala Lys Gly Gln Lys Val
        530                 535                 540
Ala Leu Lys Glu Ala Met Gly Ser Thr Gln Ser Ile Met Val Gly Pro
545                 550                 555                 560
Asp Gly Glu Leu Tyr Gly Ala Ser Asp Pro Arg Ser Val Asp Asp Leu
                565                 570                 575
Thr Ala Gly Tyr
            580

<210> SEQ ID NO 3
<211> LENGTH: 580
<212> TYPE: PRT
<213> ORGANISM: Shigella flexneri

<400> SEQUENCE: 3

Met Ile Lys Pro Thr Phe Leu Arg Arg Val Ala Ile Ala Ala Leu Leu
1               5                   10                  15
Ser Gly Ser Cys Phe Ser Ala Ala Ala Pro Ala Pro Pro Val
            20                  25                  30
Ser Tyr Gly Val Glu Glu Asp Val Phe His Pro Val Arg Ala Lys Gln
        35                  40                  45
Gly Met Val Ala Ser Val Asp Ala Thr Ala Thr Gln Val Gly Val Asp
    50                  55                  60
Ile Leu Lys Glu Gly Gly Asn Ala Val Asp Ala Val Ala Val Gly
65                  70                  75                  80
Tyr Ala Leu Ala Val Thr His Pro Gln Ala Gly Asn Leu Gly Gly Gly
                85                  90                  95
Gly Phe Met Leu Ile Arg Ser Lys Asn Gly Asn Thr Thr Ala Ile Asp
            100                 105                 110
Phe Arg Glu Met Ala Pro Ala Lys Ala Thr Arg Asp Met Phe Leu Asp
        115                 120                 125
Asp Gln Gly Asn Pro Asp Ser Lys Lys Ser Leu Thr Ser His Leu Ala
    130                 135                 140
Ser Gly Thr Pro Gly Thr Val Ala Gly Phe Ser Leu Ala Leu Asp Lys
145                 150                 155                 160
Tyr Gly Thr Met Pro Leu Asn Lys Val Val Gln Pro Ala Phe Lys Leu
                165                 170                 175
Ala Arg Asp Gly Phe Ile Val Asn Asp Ala Leu Ala Asp Asp Leu Lys
            180                 185                 190
Thr Tyr Gly Ser Glu Val Leu Pro Asn His Glu Asn Ser Lys Ala Ile
        195                 200                 205
Phe Trp Lys Glu Gly Glu Pro Leu Lys Lys Gly Asp Thr Leu Val Gln
    210                 215                 220
Ala Asn Leu Ala Lys Ser Leu Glu Met Ile Ala Glu Asn Gly Pro Asp
225                 230                 235                 240
Glu Phe Tyr Lys Gly Thr Ile Ala Glu Gln Ile Ala Gln Glu Met Gln
                245                 250                 255
Lys Asn Gly Gly Leu Ile Thr Lys Glu Asp Leu Ala Ala Tyr Lys Ala
            260                 265                 270
Val Glu Arg Thr Pro Ile Ser Gly Asp Tyr Arg Gly Tyr Gln Val Tyr
        275                 280                 285
Ser Met Pro Pro Pro Ser Ser Gly Gly Ile His Ile Val Gln Ile Leu
    290                 295                 300
```

```
Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
            325                 330                 335

Arg Ser Glu Tyr Leu Gly Asp Pro Asp Phe Val Lys Val Pro Trp Gln
            340                 345                 350

Ala Leu Thr Asn Lys Ala Tyr Ala Lys Ser Ile Ala Asp Gln Ile Asp
            355                 360                 365

Ile Lys Lys Ala Lys Pro Ser Ser Glu Ile Arg Pro Gly Lys Leu Ala
370                 375                 380

Pro Tyr Glu Ser Asn Gln Thr Thr His Tyr Ser Val Val Asp Lys Asp
385                 390                 395                 400

Gly Asn Ala Val Ala Val Thr Tyr Thr Leu Asn Thr Thr Phe Gly Thr
            405                 410                 415

Gly Ile Val Ala Gly Glu Ser Gly Ile Leu Leu Asn Asn Gln Met Asp
            420                 425                 430

Asp Phe Ser Ala Lys Pro Gly Val Pro Asn Val Tyr Gly Leu Val Gly
            435                 440                 445

Gly Asp Ala Asn Ala Val Gly Pro Asn Lys Arg Pro Leu Ser Ser Met
450                 455                 460

Ser Pro Thr Ile Val Lys Asp Gly Lys Thr Trp Leu Val Thr Gly
465                 470                 475                 480

Ser Pro Gly Gly Ser Arg Ile Ile Thr Thr Val Leu Gln Met Val Val
            485                 490                 495

Asn Ser Ile Asp Tyr Gly Met Asn Val Ala Glu Ala Thr Asn Ala Pro
            500                 505                 510

Arg Phe His His Gln Trp Leu Pro Asp Glu Leu Arg Val Glu Lys Gly
            515                 520                 525

Phe Ser Pro Asp Thr Leu Lys Leu Leu Glu Ala Lys Gly Gln Lys Val
            530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
            565                 570                 575

Thr Ala Gly Tyr
            580

<210> SEQ ID NO 4
<211> LENGTH: 581
<212> TYPE: PRT
<213> ORGANISM: Shigella dysenteriae

<400> SEQUENCE: 4

Met Ile Lys Pro Thr Tyr Leu Arg Arg Val Ala Ile Ala Ala Leu Phe
1               5                   10                  15

Thr Gly Ser Cys Phe Ser Thr Val Ala Ala Pro Pro Ala Pro Ser Pro
            20                  25                  30

Val

-continued

```
Ala Gly Phe Met Leu Ile Arg Ser Lys Asn Gly Asn Thr Thr Ala Ile
            100                 105                 110
Asp Phe Arg Glu Met Ala Pro Ala Lys Ala Thr Arg Asp Met Phe Leu
            115                 120                 125
Asp Asp Gln Gly Asn Pro Asp Ser Lys Lys Ser Leu Thr Ser His Leu
130                 135                 140
Ala Ser Gly Thr Pro Gly Thr Val Ala Gly Phe Ser Leu Ala Arg Asp
145                 150                 155                 160
Lys Tyr Gly Thr Met Pro Leu Asn Lys Val Val Gln Pro Ala Phe Lys
                    165                 170                 175
Leu Ala Arg Asp Gly Phe Ile Val Asn Asp Ala Leu Ala Asp Asp Leu
            180                 185                 190
Lys Thr Tyr Gly Ser Glu Val Leu Pro Asn His Glu Asn Ser Lys Ala
            195                 200                 205
Ile Phe Trp Lys Glu Gly Glu Pro Leu Lys Lys Gly Asp Lys Leu Val
            210                 215                 220
Gln Ala Asn Leu Ala Lys Ser Leu Glu Met Ile Ala Glu Asn Gly Leu
225                 230                 235                 240
Asp Glu Phe Tyr Lys Gly Thr Ile Ala Glu Gln Ile Ala Gln Glu Met
                    245                 250                 255
Gln Lys Asn Gly Gly Leu Ile Thr Lys Glu Asp Leu Ala Ala Tyr Lys
            260                 265                 270
Ala Val Glu Arg Thr Pro Ile Ser Gly Asp Tyr Arg Gly Tyr Gln Val
            275                 280                 285
Tyr Ser Met Pro Pro Ser Gly Gly Ile His Ile Val Gln Ile
            290                 295                 300
Leu Asn Ile Leu Glu Asn Phe Asp Met Lys Lys Tyr Gly Phe Gly Ser
305                 310                 315                 320
Ala Asp Ala Met Gln Ile Met Ala Glu Ala Lys Tyr Ala Tyr Ala
                    325                 330                 335
Asp Arg Ser Glu Tyr Leu Gly Asp Pro Asp Phe Val Lys Val Pro Trp
            340                 345                 350
Gln Ala Leu Thr Asn Lys Ala Tyr Ala Lys Ser Ile Ala Glu Gln Ile
            355                 360                 365
Asp Ile Asn Lys Ala Lys Pro Ser Ser Glu Ile Arg Pro Gly Lys Leu
            370                 375                 380
Ala Pro Tyr Glu Ser Asn Gln Thr Thr His Tyr Ser Val Val Asp Lys
385                 390                 395                 400
Asp Gly Asn Ala Val Ala Val Thr Tyr Thr Leu Asn Thr Thr Phe Gly
                    405                 410                 415
Thr Gly Ile Val Ala Gly Glu Ser Gly Ile Leu Leu Asn Asn Gln Met
            420                 425                 430
Asp Asp Phe Ser Ala Lys Pro Gly Val Pro Asn Val Tyr Gly Leu Val
            435                 440                 445
Gly Gly Asp Ala Asn Ala Val Gly Pro Asn Lys Arg Pro Leu Ser Ser
            450                 455                 460
Met Ser Pro Thr Ile Val Val Lys Asp Gly Lys Thr Trp Leu Val Thr
465                 470                 475                 480
Gly Ser Pro Gly Gly Ser Arg Ile Ile Thr Thr Val Leu Gln Met Val
                    485                 490                 495
Val Asn Ser Ile Asp Tyr Gly Met Asn Val Ala Glu Ala Thr Asn Ala
            500                 505                 510
```

```
Pro Arg Phe His His Gln Trp Leu Pro Asp Glu Leu Arg Val Glu Lys
            515                 520                 525

Gly Phe Ser Pro Asp Thr Leu Lys Leu Leu Glu Ala Lys Gly Gln Lys
530                 535                 540

Val Ala Leu Lys Glu Ala Met Gly Ser Thr Gln Ser Ile Met Val Gly
545                 550                 555                 560

Pro Asp Gly Glu Leu Tyr Gly Ala Ser Asp Pro Arg Ser Val Asp Asp
                565                 570                 575

Leu Thr Ala Gly Tyr
            580

<210> SEQ ID NO 5
<211> LENGTH: 577
<212> TYPE: PRT
<213> ORGANISM: Shigella boydii

<400> SEQUENCE: 5

Met Ile Lys Pro Thr Phe Leu Arg Arg Val Ala Ile Ala Ala Leu Leu
1               5                   10                  15

Ser Gly Ser Cys Phe Ser Ala Val Ala Ala Pro Val Ser Tyr Gly
            20                  25                  30

Val Glu Glu Asp Ile Phe His Pro Val Arg Ala Lys Gln Gly Met Val
            35                  40                  45

Ala Ser Val Asp Ala Thr Ala Thr Gln Val Gly Val Asp Ile Leu Lys
50                  55                  60

Glu Gly Gly Asn Ala Val Asp Ala Ala Val Ala Val Gly Tyr Ala Leu
65                  70                  75                  80

Ala Val Thr His Pro Gln Ala Gly Asn Leu Gly Gly Gly Gly Phe Met
            85                  90                  95

Leu Ile Arg Ser Lys Asn Gly Asn Thr Thr Ala Ile Asp Phe Arg Glu
            100                 105                 110

Met Ala Pro Ala Lys Ala Thr Arg Asp Met Phe Leu Asp Asp Gln Gly
            115                 120                 125

Asn Pro Asp Ser Lys Lys Ser Leu Thr Ser His Leu Ala Ser Gly Thr
130                 135                 140

Pro Gly Thr Val Ala Gly Phe Ser Leu Ala Leu Asp Lys Tyr Gly Thr
145                 150                 155                 160

Met Pro Leu Asn Lys Val Val Gln Pro Ala Phe Lys Leu Ala Arg Asp
                165                 170                 175

Gly Phe Ile Val Asn Asp Ala Leu Ala Asp Asp Leu Lys Thr Tyr Gly
            180                 185                 190

Ser Glu Val Leu Pro Asn His Glu Asn Ser Lys Ala Ile Phe Trp Lys
            195                 200                 205

Glu Gly Glu Pro Leu Lys Lys Gly Asp Lys Leu Val Gln Ala Asn Leu
210                 215                 220

Ala Lys Ser Leu Glu Met Ile Ala Glu Asn Gly Pro Asp Glu Phe Tyr
225                 230                 235                 240

Lys Gly Thr Ile Ala Glu Gln Ile Ala Gln Glu Met Gln Lys Asn Gly
            245                 250                 255

Gly Leu Ile Thr Lys Glu Asp Leu Ala Ala Tyr Lys Ala Val Glu Arg
            260                 265                 270

Thr Pro Ile Ser Gly Asp Tyr Arg Gly Tyr Gln Val Tyr Ser Met Pro
            275                 280                 285

Pro Pro Ser Ser Gly Gly Ile His Ile Val Gln Ile Leu Asn Ile Leu
290                 295                 300
```

Glu Asn Phe Asp Met Lys Lys Tyr Gly Phe Gly Ser Ala Asp Ala Met
305                 310                 315                 320

Gln Ile Met Ala Glu Ala Lys Tyr Ala Tyr Ala Asp Arg Ser Glu
            325                 330                 335

Tyr Leu Gly Asp Pro Asp Phe Val Lys Val Pro Trp Gln Ala Leu Thr
            340                 345                 350

Asn Lys Ala Tyr Ala Lys Ser Ile Ala Asp Gln Ile Asp Ile Asn Lys
            355                 360                 365

Ala Gln Pro Ser Ser Glu Ile Arg Pro Gly Lys Leu Ala Pro Tyr Glu
370                 375                 380

Ser Asn Gln Thr Thr His Tyr Ser Val Val Asp Lys Asp Gly Asn Ala
385                 390                 395                 400

Val Ala Val Thr Tyr Thr Leu Asn Thr Thr Phe Gly Thr Gly Ile Val
                405                 410                 415

Ala Gly Glu Ser Gly Ile Leu Leu Asn Asn Gln Met Asp Asp Phe Ser
            420                 425                 430

Ala Lys Pro Gly Val Pro Asn Val Tyr Gly Leu Val Gly Gly Asp Ala
            435                 440                 445

Asn Ala Val Gly Pro Asn Lys Arg Pro Leu Ser Ser Met Ser Pro Thr
450                 455                 460

Ile Val Val Lys Asp Gly Lys Thr Trp Leu Val Thr Gly Ser Pro Gly
465                 470                 475                 480

Gly Ser Arg Ile Ile Thr Thr Val Leu Gln Met Val Val Asn Ser Ile
                485                 490                 495

Asp Tyr Gly Met Asn Val Ala Glu Ala Thr Asn Ala Pro Arg Phe His
            500                 505                 510

His Gln Trp Leu Pro Asp Glu Leu Arg Val Glu Lys Gly Phe Ser Pro
            515                 520                 525

Asp Thr Leu Lys Leu Leu Glu Ala Lys Gly Gln Lys Val Ala Leu Lys
            530                 535                 540

Glu Ala Met Gly Ser Thr Gln Ser Ile Met Val Gly Pro Asp Gly Glu
545                 550                 555                 560

Leu Tyr Gly Ala Ser Asp Pro Arg Ser Val Asp Asp Leu Thr Ala Gly
                565                 570                 575

Tyr

<210> SEQ ID NO 6
<211> LENGTH: 580
<212> TYPE: PRT
<213> ORGANISM: Salmonella typhimurium

<400> SEQUENCE: 6

Met Lys Pro Thr Phe Met Arg Trp Val Ala Ile Ala Ala Leu Leu Ala
1               5                   10                  15

Gly Gly Thr Phe Ser Ala Val Ala Asn Pro Val Ala Pro Pro Val
            20                  25                  30

Ser Tyr Gly Val Glu Glu Asp Val Phe His Pro Val Arg Ala Thr Gln
            35                  40                  45

Gly Met Val Ala Ser Val Asp Ala Met Ala Thr Gln Val Gly Val Asp
        50                  55                  60

Ile Leu Lys Gln Gly Gly Asn Ala Val Asp Ala Ala Val Ala Val Gly
65                  70                  75                  80

Tyr Ala Leu Ala Val Thr His Pro Gln Ala Gly Asn Leu Gly Gly Gly
                85                  90                  95

```
Gly Phe Met Leu Leu Arg Thr Lys Asp Gly Thr Ala Ile Asp
            100                 105                 110

Phe Arg Glu Met Ala Pro Ala Gly Ala Thr Arg Asp Met Phe Leu Asp
            115                 120                 125

Asp Gln Gly Asn Ala Asp Ala Lys Lys Ser Leu Thr Ser His Leu Ala
            130                 135                 140

Ser Gly Thr Pro Gly Thr Val Ala Gly Phe Ser Leu Ala Leu Glu Lys
145                 150                 155                 160

Tyr Gly Thr Met Pro Leu Asn Lys Val Val Arg Pro Ala Met Lys Leu
                    165                 170                 175

Ala Glu Glu Gly Phe Val Val Asn Asp Ala Leu Ala Asn Asp Leu Lys
            180                 185                 190

Thr Tyr Gly Ser Glu Val Ile Leu Asn His Glu Asn Ser Lys Ala Ile
            195                 200                 205

Phe Trp Lys Asp Gly Glu Pro Leu Lys Lys Gly Asp Lys Leu Val Gln
            210                 215                 220

Lys Asn Leu Ala Lys Ser Leu Glu Met Ile Ala Glu Asn Gly Pro Asp
225                 230                 235                 240

Ala Phe Tyr Lys Gly Ala Ile Ala Asp Gln Ile Ala Gly Glu Met Gln
                    245                 250                 255

Lys Asn Gly Gly Leu Met Thr Lys Glu Asp Leu Ala Asn Tyr Lys Ala
            260                 265                 270

Val Glu Arg Thr Pro Ile Ser Gly Asp Tyr Arg Gly Tyr Gln Val Phe
            275                 280                 285

Ser Met Pro Pro Pro Ser Ser Gly Gly Ile His Ile Val Gln Ile Leu
            290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                    325                 330                 335

Arg Ser Glu Tyr Leu Gly Asp Pro Asp Phe Val Lys Val Pro Trp Gln
            340                 345                 350

Ala Leu Thr His Lys Ala Tyr Ala Lys Thr Leu Ala Asp Gln Ile Asp
            355                 360                 365

Ile Asn Lys Ala Lys Pro Ser Ser Gln Ile Lys Pro Gly Lys Leu Ala
            370                 375                 380

Pro Tyr Glu Ser Asn Gln Thr His Phe Ser Val Val Asp Lys Asp
385                 390                 395                 400

Gly Asn Ala Val Ala Val Thr Tyr Thr Leu Asn Thr Thr Phe Gly Thr
                    405                 410                 415

Gly Ile Val Ala Gly Asn Thr Gly Ile Leu Leu Asn Asn Gln Met Asp
            420                 425                 430

Asp Phe Ser Ala Lys Pro Gly Val Pro Asn Val Tyr Gly Leu Val Gly
            435                 440                 445

Gly Asp Ala Asn Ala Val Gly Pro Lys Lys Arg Pro Leu Ser Ser Met
            450                 455                 460

Ser Pro Thr Ile Val Val Lys Glu Gly Lys Thr Trp Leu Val Thr Gly
465                 470                 475                 480

Ser Pro Gly Gly Ser Arg Ile Ile Thr Thr Val Leu Gln Met Val Val
                    485                 490                 495

Asn Ser Ile Asp Phe Gly Met Asn Val Ala Glu Ala Thr Asn Ala Pro
            500                 505                 510
```

```
Arg Phe His His Gln Trp Leu Pro Asp Glu Leu Arg Val Glu Lys Gly
            515                 520                 525

Phe Ser Pro Asp Thr Leu Lys Leu Leu Glu Gln Lys Gly Gln Lys Val
        530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
                565                 570                 575

Thr Ala Gly Tyr
            580

<210> SEQ ID NO 7
<211> LENGTH: 580
<212> TYPE: PRT
<213> ORGANISM: Salmonella choleraesuis

<400> SEQUENCE: 7

Met Lys Pro Thr Phe Met Arg Trp Val Ala Ile Ala Ala Leu Leu Ala
1               5                   10                  15

Gly Gly Thr Phe Ser Ala Val Ala Asn Pro Val Ala Pro Pro Val
            20                  25                  30

Ser Tyr Gly Val Glu Glu Asp Val Phe His Pro Val Arg Ala Thr Gln
        35                  40                  45

Gly Met Val Ala Ser Val Asp Ala Met Ala Thr Gln Val Gly Val Asp
    50                  55                  60

Ile Leu Lys Gln Gly Gly Asn Ala Val Asp Ala Ala Val Ala Val Gly
65                  70                  75                  80

Tyr Ala Leu Ala Val Thr His Pro Gln Ala Gly Asn Leu Gly Gly Gly
                85                  90                  95

Gly Phe Met Leu Leu Arg Thr Lys Asp Gly Asn Thr Thr Ala Ile Asp
            100                 105                 110

Phe Arg Glu Met Ala Pro Ala Ala Ala Thr Arg Asp Met Phe Leu Asp
        115                 120                 125

Asp Gln Gly Asn Ala Asp Ala Lys Lys Ser Leu Thr Ser His Leu Ala
    130                 135                 140

Pro Gly Thr Pro Gly Thr Val Ala Gly Phe Ser Leu Ala Leu Glu Lys
145                 150                 155                 160

Tyr Gly Thr Met Pro Leu Asn Lys Val Val Arg Pro Ala Met Lys Leu
                165                 170                 175

Ala Glu Glu Gly Phe Val Val Asn Asp Ala Leu Ala Asp Asp Leu Lys
            180                 185                 190

Thr Tyr Gly Ser Glu Val Ile Pro Asn His Glu Asn Ser Lys Ala Ile
        195                 200                 205

Phe Trp Lys Asp Gly Glu Pro Leu Lys Lys Gly Asp Lys Leu Val Gln
    210                 215                 220

Lys Asn Leu Ala Lys Ser Leu Glu Met Ile Ala Glu Asn Gly Pro Asp
225                 230                 235                 240

Ala Phe Tyr Lys Gly Ala Ile Ala Asp Gln Ile Ala Gly Glu Met Gln
                245                 250                 255

Lys Asn Gly Gly Leu Met Thr Lys Glu Asp Leu Ala Ser Tyr Lys Ala
            260                 265                 270

Val Glu Arg Thr Pro Ile Ser Gly Asp Tyr Arg Gly Tyr Gln Val Phe
        275                 280                 285

Ser Met Pro Pro Pro Ser Ser Gly Gly Ile His Ile Val Gln Ile Leu
    290                 295                 300
```

-continued

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
            325                 330                 335

Arg Ser Glu Tyr Leu Gly Asp Ser Asp Phe Val Lys Val Pro Trp Gln
        340                 345                 350

Ala Leu Thr Asn Lys Asp Tyr Ala Lys Thr Leu Ala Asp Gln Ile Asp
    355                 360                 365

Ile Asn Lys Ala Lys Pro Ser Ser Gln Ile Lys Pro Gly Lys Leu Ala
370                 375                 380

Pro Tyr Glu Ser Asn Gln Thr Thr His Phe Ser Val Val Asp Lys Asp
385                 390                 395                 400

Gly Asn Ala Val Ala Val Thr Tyr Thr Leu Asn Thr Thr Phe Gly Thr
            405                 410                 415

Gly Ile Val Ala Gly Asn Thr Gly Ile Leu Leu Asn Asn Glu Met Asp
        420                 425                 430

Asp Phe Ser Ala Lys Pro Gly Val Pro Asn Val Tyr Gly Leu Val Gly
    435                 440                 445

Gly Asp Ala Asn Ala Val Gly Pro Lys Lys Arg Pro Leu Ser Ser Met
450                 455                 460

Ser Pro Thr Ile Val Lys Glu Gly Lys Thr Trp Leu Val Thr Gly
465                 470                 475                 480

Ser Pro Gly Gly Ser Arg Ile Ile Thr Thr Val Leu Gln Met Val Val
            485                 490                 495

Asn Ser Ile Asp Phe Gly Met Asn Val Ala Glu Ala Thr Asn Ala Pro
        500                 505                 510

Arg Phe His His Gln Trp Leu Pro Asp Glu Leu Arg Val Glu Lys Gly
    515                 520                 525

Phe Ser Pro Asp Thr Leu Lys Leu Leu Glu Gln Lys Gly Gln Lys Val
    530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
            565                 570                 575

Thr Ala Gly Tyr
            580

<210> SEQ ID NO 8
<211> LENGTH: 580
<212> TYPE: PRT
<213> ORGANISM: Salmonella enterica

<400> SEQUENCE: 8

Met Lys Pro Thr Phe Met Arg Trp Val Ala Ile Ala Ala Leu Leu Ala
1               5                   10                  15

Gly Gly Thr Phe Ser Ala Val Ala Asn Pro Val Ala Pro Val
            20                  25                  30

Ser Tyr Gly Val Glu Glu Asp Val Phe His Pro Val Arg Ala Thr Gln
        35                  40                  45

Gly Met Val Ala Ser Val Asp Ala Met Ala Thr Gln Val Gly Val Asp
    50                  55                  60

Ile Leu Lys Gln Gly Gly Asn Ala Val Asp Ala Ala Val Ala Val Gly
65                  70                  75                  80

Tyr Ala Leu Ala Val Thr His Pro Gln Ala Gly Asn Leu Gly Gly Gly

```
                     85                  90                  95
Gly Phe Met Leu Leu Arg Thr Lys Asp Gly Thr Thr Ala Ile Asp
                100                 105                 110

Phe Arg Glu Met Ala Pro Ala Ala Thr Arg Asp Met Phe Leu Asp
            115                 120                 125

Asp Gln Gly Asn Ala Asp Ala Lys Lys Ser Leu Thr Ser His Leu Ala
130                 135                 140

Ser Gly Thr Pro Gly Thr Val Ala Gly Phe Ser Leu Ala Leu Glu Lys
145                 150                 155                 160

Tyr Gly Thr Met Pro Leu Asn Lys Val Val Arg Pro Ala Met Lys Leu
                165                 170                 175

Ala Glu Glu Gly Phe Val Val Asn Asp Ala Leu Ala Asp Asp Leu Lys
            180                 185                 190

Thr Tyr Gly Ser Glu Val Ile Pro Asn His Glu Asn Ser Lys Ala Ile
        195                 200                 205

Phe Trp Lys Asp Gly Glu Pro Leu Lys Gly Asp Lys Leu Ile Gln
    210                 215                 220

Lys Asn Leu Ala Lys Ser Leu Glu Met Ile Ala Glu Asn Gly Pro Ala
225                 230                 235                 240

Ala Phe Tyr Lys Gly Ala Ile Ala Asp Gln Ile Ala Gly Glu Met Gln
                245                 250                 255

Lys Asn Gly Gly Leu Met Thr Lys Glu Asp Leu Ala Ser Tyr Lys Ala
            260                 265                 270

Val Glu Arg Thr Pro Ile Ser Gly Asp Tyr Arg Gly Tyr Gln Val Phe
        275                 280                 285

Ser Met Pro Pro Pro Ser Ser Gly Gly Ile His Ile Val Gln Ile Leu
    290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                325                 330                 335

Arg Ser Glu Tyr Leu Gly Asp Pro Asp Phe Val Lys Val Pro Trp Gln
            340                 345                 350

Ala Leu Thr Asn Lys Ala Tyr Ala Lys Thr Leu Ala Asp Gln Ile Asp
        355                 360                 365

Ile Asn Lys Ala Lys Pro Ser Ser Gln Ile Lys Pro Gly Lys Leu Ala
    370                 375                 380

Pro Tyr Glu Ser Asn Gln Thr Thr His Phe Ser Val Val Asp Lys Asp
385                 390                 395                 400

Gly Asn Ala Val Ala Val Thr Tyr Thr Leu Asn Thr Thr Phe Gly Thr
                405                 410                 415

Gly Ile Val Ala Gly Asn Thr Gly Ile Leu Leu Asn Asn Gln Met Asp
            420                 425                 430

Asp Phe Ser Ala Lys Pro Gly Val Pro Asn Val Tyr Gly Leu Val Gly
        435                 440                 445

Gly Asp Ala Asn Ala Val Glu Pro Lys Lys Arg Pro Leu Ser Ser Met
    450                 455                 460

Ser Pro Thr Ile Val Val Lys Asp Gly Lys Thr Trp Leu Val Thr Gly
465                 470                 475                 480

Ser Pro Gly Gly Ser Arg Ile Ile Thr Thr Val Leu Gln Met Val Val
                485                 490                 495

Asn Ser Ile Asp Phe Gly Met Asn Val Ala Glu Ala Thr Asn Ala Pro
            500                 505                 510
```

```
Arg Phe His His Gln Trp Leu Pro Asp Glu Leu Arg Val Glu Lys Gly
            515                 520                 525

Phe Ser Pro Asp Thr Leu Lys Leu Leu Glu Gln Lys Gly Gln Lys Val
            530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
            565                 570                 575

Thr Ala Gly Tyr
            580

<210> SEQ ID NO 9
<211> LENGTH: 589
<212> TYPE: PRT
<213> ORGANISM: Klebsiella pneumoniae

<400> SEQUENCE: 9

Asn Leu Pro Phe Arg Ser Lys Thr Met Ile Lys Thr Thr Ile Trp Arg
1               5                   10                  15

Gln Val Val Ile Ala Ala Leu Leu Ala Gly Gly Ser Phe Thr Val Ala
            20                  25                  30

Ala Asn Pro Pro Pro Pro Pro Val Ser Tyr Gly Val Glu Glu Asp
            35                  40                  45

Val Phe His Pro Val Arg Ala Arg Gln Gly Met Val Ala Ser Val Asp
            50                  55                  60

Ala Leu Ala Thr Arg Val Gly Val Asp Ile Leu Arg Gln Gly Gly Asn
65                  70                  75                  80

Ala Val Asp Ala Ala Val Ala Val Gly Tyr Ala Leu Ala Val Thr His
            85                  90                  95

Pro Gln Ala Gly Asn Ile Gly Gly Gly Gly Phe Met Met Leu Arg Thr
            100                 105                 110

Lys Asp Gly Lys Thr Thr Ala Ile Asp Phe Arg Glu Met Ala Pro Glu
            115                 120                 125

Gln Ala Thr Arg Asp Met Phe Leu Asp Asp Gln Gly Asn Pro Asp Ser
            130                 135                 140

Lys Lys Ser Leu Thr Ser His Leu Ala Ser Gly Thr Pro Gly Ser Val
145                 150                 155                 160

Ala Gly Phe Ser Leu Ala Leu Glu Lys Tyr Gly Thr Met Pro Leu Asn
            165                 170                 175

Lys Val Ile Arg Pro Ala Ile Lys Leu Ala Glu Glu Gly Phe Ile Val
            180                 185                 190

Asn Asp Ala Leu Ala Asp Asp Leu Lys Thr Tyr Gly Ser Glu Val Ile
            195                 200                 205

Pro Gln His Glu Asn Ser Lys Ala Ile Phe Trp Lys Asn Gly Glu Pro
            210                 215                 220

Leu Lys Lys Gly Asp Arg Leu Val Gln Lys Asn Leu Gly Lys Ser Leu
225                 230                 235                 240

Glu Leu Ile Ala Glu His Gly Pro Asp Ala Phe Tyr Lys Gly Ala Ile
            245                 250                 255

Ala Asp Gln Ile Ala Asn Glu Met Lys Lys His Gly Gly Leu Ile Thr
            260                 265                 270

Lys Ala Asp Leu Ala Gly Tyr Lys Ala Val Glu Arg Thr Pro Val Ser
            275                 280                 285

Gly Glu Tyr Arg Gly Tyr Glu Val Tyr Ser Met Pro Pro Pro Ser Ser
```

```
            290                 295                 300
Gly Gly Ile His Ile Val Gln Ile Leu Asn Ile Leu Glu Asn Phe Asp
305                 310                 315                 320

Met Gln Lys Tyr Gly Phe Gly Ser Ala Asp Ala Met Gln Val Met Ala
                325                 330                 335

Glu Ala Glu Lys His Ala Tyr Ala Asp Arg Ser Glu Tyr Leu Gly Asp
            340                 345                 350

Pro Asp Phe Val Asn Val Pro Trp Gln Ala Leu Thr Ser Lys Ala Tyr
        355                 360                 365

Ala Lys Ala Ile Ala Ala Glu Ile Asp Val Asn Lys Ala Lys Pro Ser
    370                 375                 380

Ser Gln Ile Arg Pro Gly Lys Leu Ala Pro Tyr Glu Ser Asn Gln Thr
385                 390                 395                 400

Thr His Phe Ser Val Val Asp Lys Asp Gly Asn Ala Val Ala Val Thr
                405                 410                 415

Tyr Thr Leu Asn Thr Thr Phe Gly Thr Gly Ile Val Ala Gly Asp Ser
            420                 425                 430

Gly Ile Leu Leu Asn Asn Gln Met Asp Asp Phe Ser Ala Lys Pro Gly
        435                 440                 445

Val Pro Asn Val Tyr Gly Leu Val Gly Gly Asp Ala Asn Ala Val Glu
    450                 455                 460

Pro Lys Lys Arg Pro Leu Ser Ser Met Ser Pro Thr Ile Val Val Lys
465                 470                 475                 480

Asp Gly Lys Thr Trp Leu Val Thr Gly Ser Pro Gly Gly Ser Arg Ile
                485                 490                 495

Ile Thr Thr Val Leu Gln Met Val Val Asn Thr Ile Asp Phe Gly Met
            500                 505                 510

Asn Val Ala Glu Ala Thr Asn Ala Pro Arg Phe His His Gln Trp Leu
        515                 520                 525

Pro Asp Glu Leu Arg Val Glu Lys Gly Phe Ser Pro Asp Thr Leu Lys
    530                 535                 540

Leu Leu Glu Ala Lys Gly Gln Lys Val Ala Leu Lys Glu Ala Met Gly
545                 550                 555                 560

Ser Thr Gln Ser Ile Met Val Gly Pro Asp Gly Met Leu Tyr Gly Ala
                565                 570                 575

Ser Asp Pro Arg Ser Pro Asp Asp Leu Thr Ala Gly Tyr
            580                 585

<210> SEQ ID NO 10
<211> LENGTH: 580
<212> TYPE: PRT
<213> ORGANISM: Salmonella enterica

<400> SEQUENCE: 10

Met Lys Pro Thr Phe Met Arg Trp Val Ala Ile Ala Ala Leu Leu Ala
1               5                   10                  15

Gly Gly Thr Phe Ser Ala Val Ala Asn Pro Val Ala Pro Pro Val
                20                  25                  30

Ser Tyr Gly Val Glu Glu Asp Val Phe His Pro Val Arg Ala Thr Gln
            35                  40                  45

Gly Met Val Ala Ser Val Asp Ala Met Ala Thr Gln Val Gly Val Asp
        50                  55                  60

Ile Leu Lys Gln Gly Gly Asn Ala Val Asp Ala Ala Val Ala Val Gly
65                  70                  75                  80
```

-continued

Tyr Ala Leu Ala Val Thr His Pro Gln Ala Gly Asn Leu Gly Gly Gly
                    85                  90                  95

Gly Phe Met Leu Leu Arg Thr Lys Asp Gly Ala Thr Thr Ala Ile Asp
            100                 105                 110

Phe Arg Glu Met Ala Pro Ala Gly Ala Thr Arg Asp Met Phe Leu Asp
        115                 120                 125

Asp Gln Gly Asn Ala Asp Ala Lys Lys Ser Leu Thr Ser His Leu Ala
    130                 135                 140

Ser Gly Thr Pro Gly Thr Val Ala Gly Phe Leu Ala Leu Glu Lys
145                 150                 155                 160

Tyr Gly Thr Met Pro Leu Asn Lys Val Val Arg Pro Ala Ile Lys Leu
                165                 170                 175

Ala Glu Glu Gly Phe Val Val Asn Asp Ala Leu Ala Asp Asp Leu Lys
            180                 185                 190

Thr Tyr Gly Ser Glu Val Ile Pro Asn His Glu Asn Ser Lys Ala Ile
        195                 200                 205

Phe Trp Lys Asp Gly Glu Pro Leu Lys Lys Gly Asp Lys Leu Val Gln
    210                 215                 220

Lys Asn Leu Ala Lys Ser Leu Glu Met Ile Ala Glu Asn Gly Pro Ala
225                 230                 235                 240

Ala Phe Tyr Lys Gly Ala Ile Ala Asp Gln Ile Ala Gly Glu Met Gln
                245                 250                 255

Lys Asn Gly Gly Leu Met Thr Lys Glu Asp Leu Ala Ser Tyr Lys Ala
            260                 265                 270

Val Glu Arg Thr Pro Ile Ser Gly Asp Tyr Arg Gly Tyr Gln Val Phe
        275                 280                 285

Ser Met Pro Pro Pro Ser Ser Gly Gly Ile His Ile Val Gln Ile Leu
    290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                325                 330                 335

Arg Ser Glu Tyr Leu Gly Asp Pro Asp Phe Val Lys Val Pro Trp Gln
            340                 345                 350

Ala Leu Thr Asn Lys Ala Tyr Ala Lys Thr Leu Ala Asp Gln Ile Asp
        355                 360                 365

Ile Asn Lys Ala Lys Pro Ser Ser Gln Ile Lys Pro Gly Lys Leu Ala
    370                 375                 380

Pro Tyr Glu Ser Asn Gln Thr Thr His Phe Ser Val Val Asp Lys Asp
385                 390                 395                 400

Gly Asn Ala Val Ala Val Thr Tyr Thr Leu Asn Thr Thr Phe Gly Thr
                405                 410                 415

Gly Ile Val Ala Gly Asn Thr Gly Ile Leu Leu Asn Asn Gln Met Asp
            420                 425                 430

Asp Phe Ser Ala Lys Pro Gly Val Pro Asn Val Tyr Gly Leu Val Gly
        435                 440                 445

Gly Asp Ala Asn Ala Val Glu Pro Lys Lys Arg Pro Leu Ser Ser Met
    450                 455                 460

Ser Pro Thr Ile Val Val Lys Asp Gly Lys Thr Trp Leu Val Thr Gly
465                 470                 475                 480

Ser Pro Gly Gly Ser Arg Ile Ile Thr Thr Val Leu Gln Met Val Val
                485                 490                 495

Asn Ser Ile Asp Phe Gly Met Asn Val Ala Glu Ala Thr Asn Ala Pro

```
                  500                 505                 510
Arg Phe His His Gln Trp Leu Pro Asp Glu Leu Arg Val Glu Lys Gly
            515                 520                 525

Phe Ser Pro Asp Thr Ile Lys Leu Leu Glu Gln Lys Gly Gln Lys Val
            530                 535                 540

Ala Leu Lys Glu Ala Met Gly Ser Thr Gln Ser Ile Met Val Gly Pro
545                 550                 555                 560

Asp Gly Ala Leu Tyr Gly Ala Ser Asp Pro Arg Ser Val Asp Asp Leu
            565                 570                 575

Thr Ala Gly Tyr
            580

<210> SEQ ID NO 11
<211> LENGTH: 581
<212> TYPE: PRT
<213> ORGANISM: Klebsiella pneumoniae

<400> SEQUENCE: 11

Met Ile Lys Thr Thr Ile Trp Arg Gln Val Val Ile Ala Ala Leu Leu
1               5                   10                  15

Ala Gly Gly Ser Phe Thr Val Ala Ala Asn Pro Pro Pro Pro Pro Pro
            20                  25                  30

Val Ser Tyr Gly Val Glu Glu Asp Val Phe His Pro Val Arg Ala Arg
        35                  40                  45

Gln Gly Met Val Ala Ser Val Asp Ala Leu Ala Thr Arg Val Gly Val
    50                  55                  60

Asp Ile Leu Arg Gln Gly Gly Asn Ala Val Asp Ala Ala Val Ala Val
65                  70                  75                  80

Gly Tyr Ala Leu Ala Val Thr His Pro Gln Ala Gly Asn Ile Gly Gly
            85                  90                  95

Gly Gly Phe Met Met Leu Arg Thr Lys Asp Gly Lys Thr Thr Ala Ile
            100                 105                 110

Asp Phe Arg Glu Met Ala Pro Glu Gln Ala Thr Arg Asp Met Phe Leu
        115                 120                 125

Asp Asp Gln Gly Asn Pro Asp Ser Lys Lys Ser Leu Thr Ser His Leu
    130                 135                 140

Ala Ser Gly Thr Pro Gly Ser Val Ala Gly Phe Ser Leu Ala Leu Glu
145                 150                 155                 160

Lys Tyr Gly Thr Met Pro Leu Asn Lys Val Ile Arg Pro Ala Ile Lys
            165                 170                 175

Leu Ala Glu Glu Gly Phe Ile Val Asn Asp Ala Leu Ala Asp Asp Leu
            180                 185                 190

Lys Thr Tyr Gly Ser Glu Val Ile Pro Gln His Glu Asn Ser Lys Ala
        195                 200                 205

Ile Phe Trp Lys Asn Gly Glu Pro Leu Lys Lys Gly Asp Arg Leu Val
    210                 215                 220

Gln Lys Asn Leu Gly Lys Ser Leu Glu Leu Ile Ala Glu His Gly Pro
225                 230                 235                 240

Asp Ala Phe Tyr Lys Gly Ala Ile Ala Asp Gln Ile Ala Asp Glu Met
            245                 250                 255

Lys Lys His Gly Gly Leu Ile Thr Lys Ala Asp Leu Ala Gly Tyr Lys
            260                 265                 270

Ala Val Glu Arg Thr Pro Val Ser Gly Glu Tyr Arg Gly Tyr Glu Val
        275                 280                 285
```

```
Tyr Ser Met Pro Pro Ser Ser Gly Gly Ile His Ile Val Gln Ile
        290                 295                 300

Leu Asn Ile Leu Glu Asn Phe Asp Met Gln Lys Tyr Gly Phe Gly Ser
305                 310                 315                 320

Ala Asp Ala Met Gln Val Met Ala Glu Ala Lys His Ala Tyr Ala
                325                 330                 335

Asp Arg Ser Glu Tyr Leu Gly Asp Pro Asp Phe Val Asn Val Pro Trp
                340                 345                 350

Gln Ala Leu Thr Ser Lys Ala Tyr Ala Lys Ala Ile Ala Glu Ile
                355                 360                 365

Asp Val Asn Lys Ala Lys Pro Ser Ser Gln Ile Arg Pro Gly Lys Leu
370                 375                 380

Ala Pro Tyr Glu Ser Asn Gln Thr Thr His Phe Ser Val Val Asp Lys
385                 390                 395                 400

Asp Gly Asn Ala Val Ala Val Thr Tyr Thr Leu Asn Thr Thr Phe Gly
                405                 410                 415

Thr Gly Ile Val Ala Gly Asn Ser Gly Ile Leu Leu Asn Asn Gln Met
                420                 425                 430

Asp Asp Phe Ser Ala Lys Pro Gly Val Pro Asn Val Tyr Gly Leu Val
                435                 440                 445

Gly Gly Asp Ala Asn Ala Val Glu Pro Lys Lys Arg Pro Leu Ser Ser
450                 455                 460

Met Ser Pro Thr Ile Val Lys Asp Gly Lys Thr Trp Leu Val Thr
465                 470                 475                 480

Gly Ser Pro Gly Gly Ser Arg Ile Ile Thr Thr Val Leu Gln Met Val
                485                 490                 495

Val Asn Thr Ile Asp Phe Gly Met Asn Val Ala Glu Ala Thr Asn Ala
                500                 505                 510

Pro Arg Phe His His Gln Trp Leu Pro Asp Glu Leu Arg Val Glu Lys
                515                 520                 525

Gly Phe Ser Pro Asp Thr Leu Lys Leu Leu Glu Ala Lys Gly Gln Lys
                530                 535                 540

Val Ala Leu Lys Glu Ala Met Gly Ser Thr Gln Ser Ile Met Val Gly
545                 550                 555                 560

Pro Asp Gly Met Leu Tyr Gly Ala Ser Asp Pro Arg Ser Pro Asp Asp
                565                 570                 575

Leu Thr Ala Gly Tyr
                580

<210> SEQ ID NO 12
<211> LENGTH: 581
<212> TYPE: PRT
<213> ORGANISM: Enterobacter cloacae

<400> SEQUENCE: 12

Met Met Lys Pro Thr Phe Leu Arg Trp Val Ala Ile Ala Ala Leu Met
1               5                   10                  15

Ala Gly Gly Thr Phe Ser Val Ala Ala Asn Pro Ala Ala Pro Pro
                20                  25                  30

Val Ser Tyr Gly Val Glu Glu Asp Val Phe His Pro Val Arg Ala Thr
                35                  40                  45

His Gly Met Val Ala Ser Val Asp Ala Leu Ala Thr Arg Val Gly Val
            50                  55                  60

Asp Ile Leu Arg Gln Gly Gly Asn Ala Val Asp Ala Ala Val Ala Val
65                  70                  75                  80
```

```
Gly Tyr Ala Leu Ala Val Thr His Pro Gln Ala Gly Asn Leu Gly Gly
                85                  90                  95
Gly Gly Phe Met Met Leu Arg Thr Lys Asp Gly Lys Thr Thr Ala Ile
            100                 105                 110
Asp Phe Arg Glu Ile Ala Pro Ser Gln Ala Ser Arg Asp Met Phe Leu
        115                 120                 125
Asp Asp Gln Gly Asn Pro Asp Ser Lys Lys Ser Leu Thr Ser His Leu
130                 135                 140
Ala Ser Gly Thr Pro Gly Thr Val Ala Gly Phe Ser Leu Ala Leu Glu
145                 150                 155                 160
Lys Tyr Gly Thr Met Pro Leu Asn Lys Val Val Gln Pro Ala Ile Lys
            165                 170                 175
Leu Ala Arg Asp Gly Phe Val Val Asn Asp Ala Leu Ala Asp Asp Leu
        180                 185                 190
Lys Thr Tyr Gly Ser Glu Val Ile Pro Asn His Glu Asn Ser Lys Ala
    195                 200                 205
Ile Phe Trp Lys Asp Gly Glu Pro Leu Lys Lys Gly Asp Arg Leu Val
210                 215                 220
Gln Lys Asn Leu Thr Lys Ser Leu Glu Leu Ile Ala Glu His Gly Pro
225                 230                 235                 240
Asp Ala Phe Tyr Lys Gly Ala Ile Ala Asp Gln Ile Ala Glu Glu Met
            245                 250                 255
Gln Lys Asn Gly Gly Leu Ile Thr Lys Ala Asp Leu Ala Glu Tyr Lys
        260                 265                 270
Ala Val Glu Arg Glu Pro Ile Ser Gly Thr Tyr Arg Gly Tyr Glu Val
    275                 280                 285
Phe Ser Met Pro Pro Pro Ser Ser Gly Gly Ile His Ile Val Gln Ile
290                 295                 300
Leu Asn Ile Leu Glu Asn Phe Asp Met His Lys Phe Gly Phe Gly Ser
305                 310                 315                 320
Ala Asp Ala Met Gln Val Met Ala Glu Ala Lys Arg Ala Tyr Ala
            325                 330                 335
Asp Arg Ser Glu Tyr Leu Gly Asp Pro Asp Phe Val Lys Val Pro Trp
        340                 345                 350
Gln Ala Leu Thr Asn Lys Ala Tyr Ala Lys Ser Ile Ala Asp Gln Ile
    355                 360                 365
Asp Ile Asn Lys Ala Lys Pro Ser Ser Glu Ile Arg Pro Gly Lys Leu
370                 375                 380
Ala Pro Tyr Glu Ser Asn Gln Thr Thr His Phe Ser Val Val Asp Lys
385                 390                 395                 400
Asp Gly Asn Ala Val Ala Val Thr Tyr Thr Leu Asn Thr Thr Phe Gly
            405                 410                 415
Thr Gly Ile Val Ala Gly Asn Ser Gly Ile Leu Leu Asn Asn Glu Met
        420                 425                 430
Asp Asp Phe Ser Ala Lys Pro Gly Val Pro Asn Val Tyr Gly Leu Val
    435                 440                 445
Gly Gly Asp Ala Asn Ala Val Gly Pro Lys Lys Arg Pro Leu Ser Ser
450                 455                 460
Met Ser Pro Thr Ile Val Val Lys Asp Gly Lys Thr Trp Leu Val Thr
465                 470                 475                 480
Gly Ser Pro Gly Gly Ser Arg Ile Ile Thr Thr Val Leu Gln Met Val
            485                 490                 495
```

```
Val Asn Ser Ile Asp Phe Gly Met Asn Val Ala Glu Ala Thr Asn Ala
            500                 505                 510

Pro Arg Phe His His Gln Trp Leu Pro Asp Glu Leu Arg Val Glu Lys
        515                 520                 525

Gly Phe Ser Pro Asp Thr Ile Lys Leu Leu Gln Arg Gly Gln Lys
    530                 535                 540

Val Ala Val Lys Glu Ala Met Gly Ser Thr Gln Ser Ile Met Val Gly
545                 550                 555                 560

Pro Asp Gly Ala Leu Phe Gly Ala Ser Asp Pro Arg Ser Val Asp Asp
                565                 570                 575

Leu Ser Ala Gly Tyr
            580

<210> SEQ ID NO 13
<211> LENGTH: 190
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
```

-continued

```
<222> LOCATION: (175)..(175)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid

<400> SEQUENCE: 13
```

Thr Thr His Xaa Ser Val Val Asp Lys Asp Gly Asn Ala Val Ala Val
1               5                   10                  15

Thr Tyr Thr Leu Asn Thr Thr Phe Gly Thr Gly Ile Val Ala Gly Xaa
                20                  25                  30

Xaa Gly Ile Leu Leu Asn Asn Xaa Met Asp Asp Phe Ser Ala Lys Pro
            35                  40                  45

Gly Val Pro Asn Val Tyr Gly Leu Val Gly Gly Asp Ala Asn Ala Val
        50                  55                  60

Xaa Pro Xaa Lys Arg Pro Leu Ser Ser Met Ser Pro Thr Ile Val Val
65                  70                  75                  80

Lys Xaa Gly Lys Thr Trp Leu Val Thr Gly Ser Pro Gly Gly Ser Arg
                85                  90                  95

Ile Ile Thr Thr Val Leu Gln Met Val Val Asn Xaa Ile Asp Xaa Gly
                100                 105                 110

Xaa Asn Val Ala Glu Ala Thr Asn Ala Pro Arg Phe His His Gln Trp
            115                 120                 125

Leu Pro Asp Glu Leu Arg Val Glu Lys Gly Phe Ser Pro Asp Thr Xaa
        130                 135                 140

Lys Leu Leu Glu Xaa Xaa Gly Gln Lys Val Ala Xaa Lys Glu Ala Met
145                 150                 155                 160

Gly Ser Thr Gln Ser Ile Met Val Gly Pro Asp Gly Xaa Leu Xaa Gly
                165                 170                 175

Ala Ser Asp Pro Arg Ser Xaa Asp Asp Leu Xaa Ala Gly Tyr
            180                 185                 190

```
<210> SEQ ID NO 14
<211> LENGTH: 1458
<212> TYPE: DNA
<213> ORGANISM: Escherichia coli
<220> FEATURE:
<221> NAME/KEY: CDS
<222> LOCATION: (1)..(1458)

<400> SEQUENCE: 14
```

| | | | | | | | | | | | | | | | | |
|---|---|---|---|---|---|---|---|---|---|---|---|---|---|---|---|---|
| gtg | tct | gaa | ctg | tct | caa | tta | tct | cca | cag | ccg | ctg | tgg | gat | att | ttt | 48 |
| Val | Ser | Glu | Leu | Ser | Gln | Leu | Ser | Pro | Gln | Pro | Leu | Trp | Asp | Ile | Phe | |
| 1 | | | | 5 | | | | | 10 | | | | | 15 | | |

| gcc | aaa | atc | tgt | tct | att | cct | cac | ccg | tcc | tat | cat | gaa | gag | caa | ctc | 96 |
|---|---|---|---|---|---|---|---|---|---|---|---|---|---|---|---|---|
| Ala | Lys | Ile | Cys | Ser | Ile | Pro | His | Pro | Ser | Tyr | His | Glu | Glu | Gln | Leu | |
| | | 20 | | | | | 25 | | | | | 30 | | | | |

| gct | gaa | tac | att | gtt | ggt | tgg | gca | aaa | gag | aaa | ggt | ttc | cat | gtc | gaa | 144 |
|---|---|---|---|---|---|---|---|---|---|---|---|---|---|---|---|---|
| Ala | Glu | Tyr | Ile | Val | Gly | Trp | Ala | Lys | Glu | Lys | Gly | Phe | His | Val | Glu | |
| | 35 | | | | | 40 | | | | | 45 | | | | | |

| cgc | gat | cag | gta | ggt | aat | atc | ctg | att | cgt | aaa | cct | gct | acc | gca | ggt | 192 |
|---|---|---|---|---|---|---|---|---|---|---|---|---|---|---|---|---|
| Arg | Asp | Gln | Val | Gly | Asn | Ile | Leu | Ile | Arg | Lys | Pro | Ala | Thr | Ala | Gly | |
| 50 | | | | | 55 | | | | | 60 | | | | | | |

| atg | gaa | aat | cgt | aaa | ccg | gtc | gtc | tta | cag | gcc | cac | ctc | gat | atg | gtg | 240 |
|---|---|---|---|---|---|---|---|---|---|---|---|---|---|---|---|---|
| Met | Glu | Asn | Arg | Lys | Pro | Val | Val | Leu | Gln | Ala | His | Leu | Asp | Met | Val | |
| 65 | | | | 70 | | | | | 75 | | | | | 80 | | |

| | | |
|---|---|---|
| ccg cag aaa aat aac gac acc gtg cat gac ttc acg aaa gat cct atc<br>Pro Gln Lys Asn Asn Asp Thr Val His Asp Phe Thr Lys Asp Pro Ile<br>                85                          90                    95 | | 288 |
| cag cct tat att gat ggc gaa tgg gtt aaa gcg cgc ggc acc acg ctg<br>Gln Pro Tyr Ile Asp Gly Glu Trp Val Lys Ala Arg Gly Thr Thr Leu<br>                100                     105                   110 | | 336 |
| ggt gcg gat aac ggc att ggt atg gcc tct gcg ctg gcg gtt ctg gct<br>Gly Ala Asp Asn Gly Ile Gly Met Ala Ser Ala Leu Ala Val Leu Ala<br>                115                     120                   125 | | 384 |
| gac gaa aac gtg gtt cac ggc ccg ctg gaa gtg ctg ctg acc atg acc<br>Asp Glu Asn Val Val His Gly Pro Leu Glu Val Leu Leu Thr Met Thr<br>      130                   135                   140 | | 432 |
| gaa gaa gcc ggt atg gac ggt gcg ttc ggc tta cag ggc aac tgg ttg<br>Glu Glu Ala Gly Met Asp Gly Ala Phe Gly Leu Gln Gly Asn Trp Leu<br>145                 150                   155                   160 | | 480 |
| cag gct gat att ctg att aac acc gac tcc gaa gaa gaa ggt gaa atc<br>Gln Ala Asp Ile Leu Ile Asn Thr Asp Ser Glu Glu Glu Gly Glu Ile<br>                  165                     170                   175 | | 528 |
| tac atg ggt tgt gcg ggg ggt atc gac ttc acc tcc aac ctg cat tta<br>Tyr Met Gly Cys Ala Gly Gly Ile Asp Phe Thr Ser Asn Leu His Leu<br>                   180                     185                   190 | | 576 |
| gat cgt gaa gcg gtt cca gct ggt ttt gaa acc ttc aag tta acc tta<br>Asp Arg Glu Ala Val Pro Ala Gly Phe Glu Thr Phe Lys Leu Thr Leu<br>             195                     200                   205 | | 624 |
| aaa ggt ctg aaa ggc ggt cac tcc ggc ggg gaa atc cac gtt ggg ctg<br>Lys Gly Leu Lys Gly Gly His Ser Gly Gly Glu Ile His Val Gly Leu<br>      210                   215                   220 | | 672 |
| ggt aat gcc aac aaa ctg ctg gtg cgc ttc ctg gcg ggt cat gcg gaa<br>Gly Asn Ala Asn Lys Leu Leu Val Arg Phe Leu Ala Gly His Ala Glu<br>225                 230                   235                   240 | | 720 |
| gaa ctg gat ctg cgc ctt atc gat ttc aac ggc ggc aca ctg cgt aac<br>Glu Leu Asp Leu Arg Leu Ile Asp Phe Asn Gly Gly Thr Leu Arg Asn<br>                  245                     250                   255 | | 768 |
| gcc atc ccg cgt gaa gcc ttt gcg acc att gct gtc gca gct gat aaa<br>Ala Ile Pro Arg Glu Ala Phe Ala Thr Ile Ala Val Ala Ala Asp Lys<br>             260                     265                   270 | | 816 |
| gtc gac gtc ctg aaa tct ctg gtg aat acc tat cag gag atc ctg aaa<br>Val Asp Val Leu Lys Ser Leu Val Asn Thr Tyr Gln Glu Ile Leu Lys<br>             275                     280                   285 | | 864 |
| aac gag ctg gca gaa aaa gag aaa aat ctg gcc ttg ttg ctg gac tct<br>Asn Glu Leu Ala Glu Lys Glu Lys Asn Leu Ala Leu Leu Leu Asp Ser<br>      290                   295                   300 | | 912 |
| gta gcg aac gat aaa gct gcc ctg att gcg aaa tct cgc gat acc ttt<br>Val Ala Asn Asp Lys Ala Ala Leu Ile Ala Lys Ser Arg Asp Thr Phe<br>305                 310                   315                   320 | | 960 |
| att cgt ctg ctg aac gcc acc ccg aac ggt gtg att cgt aac tcc gat<br>Ile Arg Leu Leu Asn Ala Thr Pro Asn Gly Val Ile Arg Asn Ser Asp<br>                  325                     330                   335 | | 1008 |
| gta gcc aaa ggt gtg gtt gaa acc tcc ctg aac gtc ggt gtg gtg acc<br>Val Ala Lys Gly Val Val Glu Thr Ser Leu Asn Val Gly Val Val Thr<br>             340                     345                   350 | | 1056 |
| atg act gac aat aac gta gaa att cac tgc ctg atc cgt tca ctg atc<br>Met Thr Asp Asn Asn Val Glu Ile His Cys Leu Ile Arg Ser Leu Ile<br>                  355                     360                   365 | | 1104 |
| gac agc ggt aaa gac tac gtg gtg agc atg ctg gat tcg ctg ggt aaa<br>Asp Ser Gly Lys Asp Tyr Val Val Ser Met Leu Asp Ser Leu Gly Lys<br>             370                     375                   380 | | 1152 |
| ctg gct ggc gcg aaa acc gaa gcg aaa ggc gca tat cct ggc tgg cag<br>Leu Ala Gly Ala Lys Thr Glu Ala Lys Gly Ala Tyr Pro Gly Trp Gln | | 1200 |

```
                385                 390                 395                 400
ccg gac gct aat tct ccg gtg atg cat ctg gta cgt gaa acc tat cag        1248
Pro Asp Ala Asn Ser Pro Val Met His Leu Val Arg Glu Thr Tyr Gln
                405                 410                 415 cgc ctg ttc aac aag acg ccg aac atc cag att atc cac gcg ggc ctg        1296
Arg Leu Phe Asn Lys Thr Pro Asn Ile Gln Ile Ile His Ala Gly Leu
                420                 425                 430 gaa tgt ggt ctg ttc aaa aaa ccg tat ccg gaa atg gac atg gtt tct        1344
Glu Cys Gly Leu Phe Lys Lys Pro Tyr Pro Glu Met Asp Met Val Ser
            435                 440                 445 atc ggg cca act atc acc ggt cca cac tct ccg gat gag caa gtt cac        1392
Ile Gly Pro Thr Ile Thr Gly Pro His Ser Pro Asp Glu Gln Val His
        450                 455                 460 atc gaa agc gta ggt cat tac tgg aca ctg ctg act gaa ctg ctg aaa        1440
Ile Glu Ser Val Gly His Tyr Trp Thr Leu Leu Thr Glu Leu Leu Lys
465                 470                 475                 480 gaa att ccg gcg aag taa                                                1458
Glu Ile Pro Ala Lys
                485

<210> SEQ ID NO 15
<211> LENGTH: 485
<212> TYPE: PRT
<213> ORGANISM: Escherichia coli

<400> SEQUENCE: 15

Val Ser Glu Leu Ser Gln Leu Ser Pro Gln Pro Leu Trp Asp Ile Phe
1               5                   10                  15

Ala Lys Ile Cys Ser Ile Pro His Pro Ser Tyr His Glu Glu Gln Leu
            20                  25                  30

Ala Glu Tyr Ile Val Gly Trp Ala Lys Glu Lys Gly Phe His Val Glu
        35                  40                  45

Arg Asp Gln Val Gly Asn Ile Leu Ile Arg Lys Pro Ala Thr Ala Gly
    50                  55                  60

Met Glu Asn Arg Lys Pro Val Val Leu Gln Ala His Leu Asp Met Val
65                  70                  75                  80

Pro Gln Lys Asn Asn Asp Thr Val His Asp Phe Thr Lys Asp Pro Ile
                85                  90                  95

Gln Pro Tyr Ile Asp Gly Glu Trp Val Lys Ala Arg Gly Thr Thr Leu
            100                 105                 110

Gly Ala Asp Asn Gly Ile Gly Met Ala Ser Ala Leu Ala Val Leu Ala
        115                 120                 125

Asp Glu Asn Val Val His Gly Pro Leu Glu Val Leu Leu Thr Met Thr
    130                 135                 140

Glu Glu Ala Gly Met Asp Gly Ala Phe Gly Leu Gln Gly Asn Trp Leu
145                 150                 155                 160

Gln Ala Asp Ile Leu Ile Asn Thr Asp Ser Glu Glu Glu Gly Glu Ile
                165                 170                 175

Tyr Met Gly Cys Ala Gly Gly Ile Asp Phe Thr Ser Asn Leu His Leu
            180                 185                 190

Asp Arg Glu Ala Val Pro Ala Gly Phe Glu Thr Phe Lys Leu Thr Leu
        195                 200                 205

Lys Gly Leu Lys Gly Gly His Ser Gly Gly Glu Ile His Val Gly Leu
    210                 215                 220

Gly Asn Ala Asn Lys Leu Leu Val Arg Phe Leu Ala Gly His Ala Glu
225                 230                 235                 240
```

```
Glu Leu Asp Leu Arg Leu Ile Asp Phe Asn Gly Gly Thr Leu Arg Asn
                245                 250                 255

Ala Ile Pro Arg Glu Ala Phe Ala Thr Ile Ala Val Ala Ala Asp Lys
            260                 265                 270

Val Asp Val Leu Lys Ser Leu Val Asn Thr Tyr Gln Glu Ile Leu Lys
        275                 280                 285

Asn Glu Leu Ala Glu Lys Glu Lys Asn Leu Ala Leu Leu Leu Asp Ser
    290                 295                 300

Val Ala Asn Asp Lys Ala Ala Leu Ile Ala Lys Ser Arg Asp Thr Phe
305                 310                 315                 320

Ile Arg Leu Leu Asn Ala Thr Pro Asn Gly Val Ile Arg Asn Ser Asp
                325                 330                 335

Val Ala Lys Gly Val Val Glu Thr Ser Leu Asn Val Gly Val Val Thr
            340                 345                 350

Met Thr Asp Asn Asn Val Glu Ile His Cys Leu Ile Arg Ser Leu Ile
        355                 360                 365

Asp Ser Gly Lys Asp Tyr Val Val Ser Met Leu Asp Ser Leu Gly Lys
    370                 375                 380

Leu Ala Gly Ala Lys Thr Glu Ala Lys Gly Ala Tyr Pro Gly Trp Gln
385                 390                 395                 400

Pro Asp Ala Asn Ser Pro Val Met His Leu Val Arg Glu Thr Tyr Gln
                405                 410                 415

Arg Leu Phe Asn Lys Thr Pro Asn Ile Gln Ile Ile His Ala Gly Leu
            420                 425                 430

Glu Cys Gly Leu Phe Lys Lys Pro Tyr Pro Glu Met Asp Met Val Ser
        435                 440                 445

Ile Gly Pro Thr Ile Thr Gly Pro His Ser Pro Asp Glu Gln Val His
    450                 455                 460

Ile Glu Ser Val Gly His Tyr Trp Thr Leu Leu Thr Glu Leu Leu Lys
465                 470                 475                 480

Glu Ile Pro Ala Lys
            485

<210> SEQ ID NO 16
<211> LENGTH: 1512
<212> TYPE: DNA
<213> ORGANISM: Escherichia coli
<220> FEATURE:
<221> NAME/KEY: CDS
<222> LOCATION: (1)..(1512)

<400> SEQUENCE: 16 atg gag ttt agt gta aaa agc ggt agc ccg gag aaa cag cgg agt gcc      48
Met Glu Phe Ser Val Lys Ser Gly Ser Pro Glu Lys Gln Arg Ser Ala
1               5                   10                  15 tgc atc gtc gtg ggc gtc ttc gaa cca cgt cgc ctt tct ccg att gca      96
Cys Ile Val Val Gly Val Phe Glu Pro Arg Arg Leu Ser Pro Ile Ala
            20                  25                  30 gaa cag ctc gat aaa atc agc gat ggg tac atc agc gcc ctg cta cgt     144
Glu Gln Leu Asp Lys Ile Ser Asp Gly Tyr Ile Ser Ala Leu Leu Arg
        35                  40                  45 cgg ggc gaa ctg gaa gga aaa ccg ggg cag aca ttg ttg ctg cac cat     192
Arg Gly Glu Leu Glu Gly Lys Pro Gly Gln Thr Leu Leu Leu His His
    50                  55                  60 gtt ccg aat gta ctt tcc gag cga att ctc ctt att ggt tgc ggc aaa     240
Val Pro Asn Val Leu Ser Glu Arg Ile Leu Leu Ile Gly Cys Gly Lys
65                  70                  75                  80
```

```
gaa cgt gag ctg gat gag cgt cag tac aag cag gtt att cag aaa acc         288
Glu Arg Glu Leu Asp Glu Arg Gln Tyr Lys Gln Val Ile Gln Lys Thr
                85                  90                  95 att aat acg ctg aat gat act ggc tca atg gaa gcg gtc tgc ttt ctg         336
Ile Asn Thr Leu Asn Asp Thr Gly Ser Met Glu Ala Val Cys Phe Leu
    100                 105                 110 act gag ctg cac gtt aaa ggc cgt aac aac tac tgg aaa gtg cgt cag         384
Thr Glu Leu His Val Lys Gly Arg Asn Asn Tyr Trp Lys Val Arg Gln
        115                 120                 125 gct gtc gag acg gca aaa gag acg ctc tac agt ttc gat cag ctg aaa         432
Ala Val Glu Thr Ala Lys Glu Thr Leu Tyr Ser Phe Asp Gln Leu Lys
130                 135                 140 acg aac aag agc gaa ccg cgt cgt ccg ctg cgt aag atg gtg ttc aac         480
Thr Asn Lys Ser Glu Pro Arg Arg Pro Leu Arg Lys Met Val Phe Asn
145                 150                 155                 160 gtg ccg acc cgc cgt gaa ctg acc agc ggt gag cgc gcg atc cag cac         528
Val Pro Thr Arg Arg Glu Leu Thr Ser Gly Glu Arg Ala Ile Gln His
            165                 170                 175 ggt ctg gcg att gcc gcc ggg att aaa gca gca aaa gat ctc ggc aat         576
Gly Leu Ala Ile Ala Ala Gly Ile Lys Ala Ala Lys Asp Leu Gly Asn
                180                 185                 190 atg ccg ccg aat atc tgt aac gcc gct tac ctc gct tca caa gcg cgc         624
Met Pro Pro Asn Ile Cys Asn Ala Ala Tyr Leu Ala Ser Gln Ala Arg
                    195                 200                 205 cag ctg gct gac agc tac agc aag aat gtc atc acc cgc gtt atc ggc         672
Gln Leu Ala Asp Ser Tyr Ser Lys Asn Val Ile Thr Arg Val Ile Gly
        210                 215                 220 gaa cag cag atg aaa gag ctg ggg atg cat tcc tat ctg gcg gtc ggt         720
Glu Gln Gln Met Lys Glu Leu Gly Met His Ser Tyr Leu Ala Val Gly
225                 230                 235                 240 cag ggt tcg caa aac gaa tcg ctg atg tcg gtg att gag tac aaa ggc         768
Gln Gly Ser Gln Asn Glu Ser Leu Met Ser Val Ile Glu Tyr Lys Gly
                245                 250                 255 aac gcg tcg gaa gat gca cgc cca atc gtg ctg gtg ggt aaa ggt tta         816
Asn Ala Ser Glu Asp Ala Arg Pro Ile Val Leu Val Gly Lys Gly Leu
                    260                 265                 270 acc ttc gac tcc ggc ggt atc tcg atc aag cct tca gaa ggc atg gat         864
Thr Phe Asp Ser Gly Gly Ile Ser Ile Lys Pro Ser Glu Gly Met Asp
        275                 280                 285 gag atg aag tac gat atg tgc ggt gcg gca gcg gtt tac ggc gtg atg         912
Glu Met Lys Tyr Asp Met Cys Gly Ala Ala Ala Val Tyr Gly Val Met
    290                 295                 300 cgg atg gtc gcg gag cta caa ctg ccg att aac gtt atc ggc gtg ttg         960
Arg Met Val Ala Glu Leu Gln Leu Pro Ile Asn Val Ile Gly Val Leu
305                 310                 315                 320 gca ggc tgc gaa aac atg cct ggc gga cga gcc tat cgt ccg ggc gat        1008
Ala Gly Cys Glu Asn Met Pro Gly Gly Arg Ala Tyr Arg Pro Gly Asp
                325                 330                 335 gtg tta acc acc atg tcc ggt caa acc gtt gaa gtg ctg aac acc gac        1056
Val Leu Thr Thr Met Ser Gly Gln Thr Val Glu Val Leu Asn Thr Asp
                    340                 345                 350 gct gaa ggc cgc ctg gta ctg tgc gac gtg tta act tac gtt gag cgt        1104
Ala Glu Gly Arg Leu Val Leu Cys Asp Val Leu Thr Tyr Val Glu Arg
        355                 360                 365 ttt gag ccg gaa gcg gtg att gac gtg gcg acg ctg acc ggt gcc tgc        1152
Phe Glu Pro Glu Ala Val Ile Asp Val Ala Thr Leu Thr Gly Ala Cys
    370                 375                 380 gtg atc gcg ctg ggt cat cat att act ggt ctg atg gcg aac cat aat        1200
Val Ile Ala Leu Gly His His Ile Thr Gly Leu Met Ala Asn His Asn
385                 390                 395                 400
```

```
ccg ctg gcc cat gaa ctg att gcc gcg tct gaa caa tcc ggt gac cgc      1248
Pro Leu Ala His Glu Leu Ile Ala Ala Ser Glu Gln Ser Gly Asp Arg
            405                 410                 415 gca tgg cgc tta ccg ctg ggt gac gag tat cag gaa caa ctg gag tcc      1296
Ala Trp Arg Leu Pro Leu Gly Asp Glu Tyr Gln Glu Gln Leu Glu Ser
        420                 425                 430 aat ttt gcc gat atg gcg aac att ggc ggt cgt cct ggt ggg gcg att      1344
Asn Phe Ala Asp Met Ala Asn Ile Gly Gly Arg Pro Gly Gly Ala Ile
            435                 440                 445 acc gca ggt tgc ttc ctg tca cgc ttt acc cgt aag tac aac tgg gcg      1392
Thr Ala Gly Cys Phe Leu Ser Arg Phe Thr Arg Lys Tyr Asn Trp Ala
        450                 455                 460 cac ctg gat atc gcc ggt acc gcc tgg cgt tct ggt aaa gca aaa ggc      1440
His Leu Asp Ile Ala Gly Thr Ala Trp Arg Ser Gly Lys Ala Lys Gly
465                 470                 475                 480 gcc acc ggt cgt ccg gta gcg ttg ctg gca cag ttc ctg tta aac cgc      1488
Ala Thr Gly Arg Pro Val Ala Leu Leu Ala Gln Phe Leu Leu Asn Arg
                485                 490                 495 gct ggg ttt aac ggc gaa gag taa                                      1512
Ala Gly Phe Asn Gly Glu Glu
                500

<210> SEQ ID NO 17
<211> LENGTH: 503
<212> TYPE: PRT
<213> ORGANISM: Escherichia coli

<400> SEQUENCE: 17

Met Glu Phe Ser Val Lys Ser Gly Ser Pro Glu Lys Gln Arg Ser Ala
1               5                   10                  15

Cys Ile Val Val Gly Val Phe Glu Pro Arg Arg Leu Ser Pro Ile Ala
            20                  25                  30

Glu Gln Leu Asp Lys Ile Ser Asp Gly Tyr Ile Ser Ala Leu Leu Arg
        35                  40                  45

Arg Gly Glu Leu Glu Gly Lys Pro Gly Gln Thr Leu Leu Leu His His
    50                  55                  60

Val Pro Asn Val Leu Ser Glu Arg Ile Leu Ile Gly Cys Gly Lys
65                  70                  75                  80

Glu Arg Glu Leu Asp Glu Arg Gln Tyr Lys Gln Val Ile Gln Lys Thr
                85                  90                  95

Ile Asn Thr Leu Asn Asp Thr Gly Ser Met Glu Ala Val Cys Phe Leu
            100                 105                 110

Thr Glu Leu His Val Lys Gly Arg Asn Asn Tyr Trp Lys Val Arg Gln
        115                 120                 125

Ala Val Glu Thr Ala Lys Glu Thr Leu Tyr Ser Phe Asp Gln Leu Lys
    130                 135                 140

Thr Asn Lys Ser Glu Pro Arg Arg Pro Leu Arg Lys Met Val Phe Asn
145                 150                 155                 160

Val Pro Thr Arg Arg Glu Leu Thr Ser Gly Glu Arg Ala Ile Gln His
                165                 170                 175

Gly Leu Ala Ile Ala Ala Gly Ile Lys Ala Lys Asp Leu Gly Asn
            180                 185                 190

Met Pro Pro Asn Ile Cys Asn Ala Ala Tyr Leu Ala Ser Gln Ala Arg
        195                 200                 205

Gln Leu Ala Asp Ser Tyr Ser Lys Asn Val Ile Thr Arg Val Ile Gly
    210                 215                 220
```

```
Glu Gln Gln Met Lys Glu Leu Gly Met His Ser Tyr Leu Ala Val Gly
225                 230                 235                 240

Gln Gly Ser Gln Asn Glu Ser Leu Met Ser Val Ile Glu Tyr Lys Gly
            245                 250                 255

Asn Ala Ser Glu Asp Ala Arg Pro Ile Val Leu Val Gly Lys Gly Leu
        260                 265                 270

Thr Phe Asp Ser Gly Gly Ile Ser Ile Lys Pro Ser Glu Gly Met Asp
    275                 280                 285

Glu Met Lys Tyr Asp Met Cys Gly Ala Ala Val Tyr Gly Val Met
290                 295                 300

Arg Met Val Ala Glu Leu Gln Leu Pro Ile Asn Val Ile Gly Val Leu
305                 310                 315                 320

Ala Gly Cys Glu Asn Met Pro Gly Gly Arg Ala Tyr Arg Pro Gly Asp
            325                 330                 335

Val Leu Thr Thr Met Ser Gly Gln Thr Val Glu Val Leu Asn Thr Asp
        340                 345                 350

Ala Glu Gly Arg Leu Val Leu Cys Asp Val Leu Thr Tyr Val Glu Arg
    355                 360                 365

Phe Glu Pro Glu Ala Val Ile Asp Val Ala Thr Leu Thr Gly Ala Cys
370                 375                 380

Val Ile Ala Leu Gly His His Ile Thr Gly Leu Met Ala Asn His Asn
385                 390                 395                 400

Pro Leu Ala His Glu Leu Ile Ala Ala Ser Glu Gln Ser Gly Asp Arg
            405                 410                 415

Ala Trp Arg Leu Pro Leu Gly Asp Glu Tyr Gln Glu Gln Leu Glu Ser
        420                 425                 430

Asn Phe Ala Asp Met Ala Asn Ile Gly Gly Arg Pro Gly Gly Ala Ile
    435                 440                 445

Thr Ala Gly Cys Phe Leu Ser Arg Phe Thr Arg Lys Tyr Asn Trp Ala
450                 455                 460

His Leu Asp Ile Ala Gly Thr Ala Trp Arg Ser Gly Lys Ala Lys Gly
465                 470                 475                 480

Ala Thr Gly Arg Pro Val Ala Leu Leu Ala Gln Phe Leu Leu Asn Arg
            485                 490                 495

Ala Gly Phe Asn Gly Glu Glu
            500

<210> SEQ ID NO 18
<211> LENGTH: 1284
<212> TYPE: DNA
<213> ORGANISM: Escherichia coli
<220> FEATURE:
<221> NAME/KEY: CDS
<222> LOCATION: (1)..(1284)

<400> SEQUENCE: 18 atg aca gaa gcg atg aag att acc ctc tct acc caa cct gcc gac gcg      48
Met Thr Glu Ala Met Lys Ile Thr Leu Ser Thr Gln Pro Ala Asp Ala
1               5                   10                  15 cgc tgg gga gaa aaa gca act tac agc att aat aat gac ggc att acc      96
Arg Trp Gly Glu Lys Ala Thr Tyr Ser Ile Asn Asn Asp Gly Ile Thr
            20                  25                  30 ctg cat ttg aac ggg gca gac gat ctg ggg ctg atc cag cgt gcg gcg     144
Leu His Leu Asn Gly Ala Asp Asp Leu Gly Leu Ile Gln Arg Ala Ala
        35                  40                  45 cgc aag att gac ggt ctg ggc atc aag cat gtt cag tta agc ggt gaa     192
Arg Lys Ile Asp Gly Leu Gly Ile Lys His Val Gln Leu Ser Gly Glu
```

```
          50                  55                  60
ggc tgg gat gcg gat cgc tgc tgg gca ttc tgg caa ggt tac aaa gcc         240
Gly Trp Asp Ala Asp Arg Cys Trp Ala Phe Trp Gln Gly Tyr Lys Ala
 65              70                  75                  80 ccg aaa ggc acg cgt aaa gtg gtg tgg ccg gat ctg gac gat gcc cag         288
Pro Lys Gly Thr Arg Lys Val Val Trp Pro Asp Leu Asp Asp Ala Gln
                 85                  90                  95 cgc cag gaa ctg gat aac cgc ctg atg atc atc gac tgg gtg cgt gac         336
Arg Gln Glu Leu Asp Asn Arg Leu Met Ile Ile Asp Trp Val Arg Asp
            100                 105                 110 acc atc aac gca ccg gca gaa gaa ttg gga cca tcg caa ctg gca cag         384
Thr Ile Asn Ala Pro Ala Glu Glu Leu Gly Pro Ser Gln Leu Ala Gln
        115                 120                 125 cgt gct gtt gat ctg atc agc aac gtc gcg ggc gat cgt gtg act tat         432
Arg Ala Val Asp Leu Ile Ser Asn Val Ala Gly Asp Arg Val Thr Tyr
    130                 135                 140 cgg atc acc aaa ggc gaa gat ctg cgt gag caa ggt tat atg ggg ctg         480
Arg Ile Thr Lys Gly Glu Asp Leu Arg Glu Gln Gly Tyr Met Gly Leu
145                 150                 155                 160 cac aca gtc gga cgc ggt tca gaa cgt tct ccg gta ttg ctg gcg ctg         528
His Thr Val Gly Arg Gly Ser Glu Arg Ser Pro Val Leu Leu Ala Leu
                165                 170                 175 gat tac aac cca act ggc gat aaa gaa gcg cca gtg tac gcg tgc ctg         576
Asp Tyr Asn Pro Thr Gly Asp Lys Glu Ala Pro Val Tyr Ala Cys Leu
            180                 185                 190 gta ggt aaa ggt atc act ttt gac tcc ggc ggc tac agc atc aaa cag         624
Val Gly Lys Gly Ile Thr Phe Asp Ser Gly Gly Tyr Ser Ile Lys Gln
        195                 200                 205 act gcg ttt atg gac tcg atg aag tcg gac atg ggc ggc gcg gca acg         672
Thr Ala Phe Met Asp Ser Met Lys Ser Asp Met Gly Gly Ala Ala Thr
    210                 215                 220 gtt acc ggg gcg ctg gca ttt gcc att acg cgc gga ctg aac aag cgc         720
Val Thr Gly Ala Leu Ala Phe Ala Ile Thr Arg Gly Leu Asn Lys Arg
225                 230                 235                 240 gtg aag ctg ttc ctc tgc tgt gcg gat aac ctg att agc ggc aat gcg         768
Val Lys Leu Phe Leu Cys Cys Ala Asp Asn Leu Ile Ser Gly Asn Ala
                245                 250                 255 ttc aag ctg ggc gat atc atc acc tat cgc aac ggt aaa aaa gtt gaa         816
Phe Lys Leu Gly Asp Ile Ile Thr Tyr Arg Asn Gly Lys Lys Val Glu
            260                 265                 270 gtg atg aac act gat gcc gaa ggg cgt ctg gtg ctt gcc gat ggt ctg         864
Val Met Asn Thr Asp Ala Glu Gly Arg Leu Val Leu Ala Asp Gly Leu
        275                 280                 285 att gat gcc agt gcg cag aaa ccg gaa atg atc att gat gcg gcg acc         912
Ile Asp Ala Ser Ala Gln Lys Pro Glu Met Ile Ile Asp Ala Ala Thr
    290                 295                 300 ctc acc ggg gcg gcg aaa act gcg ctg ggt aat gat tat cac gcg ctg         960
Leu Thr Gly Ala Ala Lys Thr Ala Leu Gly Asn Asp Tyr His Ala Leu
305                 310                 315                 320 ttc agt ttt gac gat gcg ctg gcc ggt cgc ttg ctg gcg agt gcc gcg        1008
Phe Ser Phe Asp Asp Ala Leu Ala Gly Arg Leu Leu Ala Ser Ala Ala
                325                 330                 335 cag gag aac gaa ccg ttc tgg cgt ctg ccg ctg gcg gag ttc cac cgc        1056
Gln Glu Asn Glu Pro Phe Trp Arg Leu Pro Leu Ala Glu Phe His Arg
            340                 345                 350 agc cag ctg ccg tct aac ttt gcc gaa ctg aac aat acc gga agc gcg        1104
Ser Gln Leu Pro Ser Asn Phe Ala Glu Leu Asn Asn Thr Gly Ser Ala
        355                 360                 365 gcg tat ccg gca ggc gcg agc acg gcg gcg ggc ttc ctg tcg cac ttt        1152
```

```
Ala Tyr Pro Ala Gly Ala Ser Thr Ala Ala Gly Phe Leu Ser His Phe
        370                 375                 380 gtt gag aac tat cag caa ggc tgg ctg cat atc gac tgc tcg gcg act         1200
Val Glu Asn Tyr Gln Gln Gly Trp Leu His Ile Asp Cys Ser Ala Thr
385                 390                 395                 400 tac cgt aaa gcg ccg gtt gaa cag tgg tct gcg ggc gct acg gga ctt         1248
Tyr Arg Lys Ala Pro Val Glu Gln Trp Ser Ala Gly Ala Thr Gly Leu
                405                 410                 415 ggt gtg cgc acg ata gct aat ctg tta acg gcg taa                         1284
Gly Val Arg Thr Ile Ala Asn Leu Leu Thr Ala
                420                 425

<210> SEQ ID NO 19
<211> LENGTH: 427
<212> TYPE: PRT
<213> ORGANISM: Escherichia coli

<400> SEQUENCE: 19

Met Thr Glu Ala Met Lys Ile Thr Leu Ser Thr Gln Pro Ala Asp Ala
1               5                   10                  15

Arg Trp Gly Glu Lys Ala Thr Tyr Ser Ile Asn Asn Asp Gly Ile Thr
            20                  25                  30

Leu His Leu Asn Gly Ala Asp Asp Leu Gly Leu Ile Gln Arg Ala Ala
        35                  40                  45

Arg Lys Ile Asp Gly Leu Gly Ile Lys His Val Gln Leu Ser Gly Glu
    50                  55                  60

Gly Trp Asp Ala Asp Arg Cys Trp Ala Phe Trp Gln Gly Tyr Lys Ala
65                  70                  75                  80

Pro Lys Gly Thr Arg Lys Val Val Trp Pro Asp Leu Asp Asp Ala Gln
                85                  90                  95

Arg Gln Glu Leu Asp Asn Arg Leu Met Ile Ile Asp Trp Val Arg Asp
            100                 105                 110

Thr Ile Asn Ala Pro Ala Glu Glu Leu Gly Pro Ser Gln Leu Ala Gln
        115                 120                 125

Arg Ala Val Asp Leu Ile Ser Asn Val Ala Gly Asp Arg Val Thr Tyr
    130                 135                 140

Arg Ile Thr Lys Gly Glu Asp Leu Arg Glu Gln Gly Tyr Met Gly Leu
145                 150                 155                 160

His Thr Val Gly Arg Gly Ser Glu Arg Ser Pro Val Leu Leu Ala Leu
                165                 170                 175

Asp Tyr Asn Pro Thr Gly Asp Lys Glu Ala Pro Val Tyr Ala Cys Leu
            180                 185                 190

Val Gly Lys Gly Ile Thr Phe Asp Ser Gly Gly Tyr Ser Ile Lys Gln
        195                 200                 205

Thr Ala Phe Met Asp Ser Met Lys Ser Asp Met Gly Gly Ala Ala Thr
    210                 215                 220

Val Thr Gly Ala Leu Ala Phe Ala Ile Thr Arg Gly Leu Asn Lys Arg
225                 230                 235                 240

Val Lys Leu Phe Leu Cys Cys Ala Asp Asn Leu Ile Ser Gly Asn Ala
                245                 250                 255

Phe Lys Leu Gly Asp Ile Ile Thr Tyr Arg Asn Gly Lys Lys Val Glu
            260                 265                 270

Val Met Asn Thr Asp Ala Glu Gly Arg Leu Val Leu Ala Asp Gly Leu
        275                 280                 285

Ile Asp Ala Ser Ala Gln Lys Pro Glu Met Ile Ile Asp Ala Ala Thr
    290                 295                 300
```

```
Leu Thr Gly Ala Ala Lys Thr Ala Leu Gly Asn Asp Tyr His Ala Leu
305                 310                 315                 320

Phe Ser Phe Asp Asp Ala Leu Ala Gly Arg Leu Leu Ala Ser Ala Ala
                325                 330                 335

Gln Glu Asn Glu Pro Phe Trp Arg Leu Pro Leu Ala Glu Phe His Arg
            340                 345                 350

Ser Gln Leu Pro Ser Asn Phe Ala Glu Leu Asn Asn Thr Gly Ser Ala
        355                 360                 365

Ala Tyr Pro Ala Gly Ala Ser Thr Ala Ala Gly Phe Leu Ser His Phe
    370                 375                 380

Val Glu Asn Tyr Gln Gln Gly Trp Leu His Ile Asp Cys Ser Ala Thr
385                 390                 395                 400

Tyr Arg Lys Ala Pro Val Glu Gln Trp Ser Ala Gly Ala Thr Gly Leu
                405                 410                 415

Gly Val Arg Thr Ile Ala Asn Leu Leu Thr Ala
                420                 425

<210> SEQ ID NO 20
<211> LENGTH: 690
<212> TYPE: DNA
<213> ORGANISM: Escherichia coli
<220> FEATURE:
<221> NAME/KEY: CDS
<222> LOCATION: (1)..(690)

<400> SEQUENCE: 20
```

| | | | | | | | | | | | | | | | | |
|---|---|---|---|---|---|---|---|---|---|---|---|---|---|---|---|---|
| atg | gaa | ctg | ctt | tta | ttg | agt | aac | tcg | acg | ctg | ccg | ggt | aaa | gcc | tgg | 48 |
| Met | Glu | Leu | Leu | Leu | Leu | Ser | Asn | Ser | Thr | Leu | Pro | Gly | Lys | Ala | Trp | |
| 1 | | | | 5 | | | | | 10 | | | | | 15 | | |
| ctg | gaa | cat | gca | ctg | ccg | cta | att | gct | gaa | cag | ttg | cag | ggt | cgc | cgc | 96 |
| Leu | Glu | His | Ala | Leu | Pro | Leu | Ile | Ala | Glu | Gln | Leu | Gln | Gly | Arg | Arg | |
| | | | 20 | | | | | 25 | | | | | 30 | | | |
| tca | gcg | gtg | ttt | atc | cct | ttc | gct | ggc | gta | acg | cag | acc | tgg | gat | gat | 144 |
| Ser | Ala | Val | Phe | Ile | Pro | Phe | Ala | Gly | Val | Thr | Gln | Thr | Trp | Asp | Asp | |
| | | | 35 | | | | | 40 | | | | | 45 | | | |
| tac | aca | gcg | aaa | acg | gct | gcg | gtt | ctc | gct | ccg | ctg | ggt | gtt | tct | gtc | 192 |
| Tyr | Thr | Ala | Lys | Thr | Ala | Ala | Val | Leu | Ala | Pro | Leu | Gly | Val | Ser | Val | |
| | 50 | | | | | 55 | | | | | 60 | | | | | |
| acc | ggt | att | cat | agc | gtt | gtc | gat | ccc | gtt | gcc | gcg | att | gaa | aat | gct | 240 |
| Thr | Gly | Ile | His | Ser | Val | Val | Asp | Pro | Val | Ala | Ala | Ile | Glu | Asn | Ala | |
| 65 | | | | | 70 | | | | | 75 | | | | | 80 | |
| gag | atc | gtg | att | gtc | ggc | ggc | ggg | aat | act | ttc | cag | ttg | ctg | aaa | cag | 288 |
| Glu | Ile | Val | Ile | Val | Gly | Gly | Gly | Asn | Thr | Phe | Gln | Leu | Leu | Lys | Gln | |
| | | | | 85 | | | | | 90 | | | | | 95 | | |
| tgc | cgc | gag | cgc | ggg | ctg | ctg | gca | cca | att | act | gac | gtg | gtt | aaa | cgt | 336 |
| Cys | Arg | Glu | Arg | Gly | Leu | Leu | Ala | Pro | Ile | Thr | Asp | Val | Val | Lys | Arg | |
| | | | 100 | | | | | 105 | | | | | 110 | | | |
| ggc | gct | ctg | tat | att | ggc | tgg | agc | gca | ggc | gct | aac | ctt | gct | tgc | cca | 384 |
| Gly | Ala | Leu | Tyr | Ile | Gly | Trp | Ser | Ala | Gly | Ala | Asn | Leu | Ala | Cys | Pro | |
| | | | 115 | | | | | 120 | | | | | 125 | | | |
| act | att | cgt | acc | acc | aac | gat | atg | ccg | att | gtc | gat | ccg | caa | ggt | ttc | 432 |
| Thr | Ile | Arg | Thr | Thr | Asn | Asp | Met | Pro | Ile | Val | Asp | Pro | Gln | Gly | Phe | |
| | | 130 | | | | | 135 | | | | | 140 | | | | |
| gat | gcg | cta | aat | ctg | ttc | ccg | ctg | caa | atc | aac | ccg | cac | ttc | acc | aac | 480 |
| Asp | Ala | Leu | Asn | Leu | Phe | Pro | Leu | Gln | Ile | Asn | Pro | His | Phe | Thr | Asn | |
| 145 | | | | | 150 | | | | | 155 | | | | | 160 | |
| gcg | ctg | ccg | gaa | ggc | cat | aaa | ggt | gaa | acc | cgt | gag | cag | cgt | att | cgc | 528 |
| Ala | Leu | Pro | Glu | Gly | His | Lys | Gly | Glu | Thr | Arg | Glu | Gln | Arg | Ile | Arg | |
| | | | | 165 | | | | | 170 | | | | | 175 | | |

```
gaa ctg ctg gtc gtc gcg cca gaa ctg acg att att ggt cta ccg gaa      576
Glu Leu Leu Val Val Ala Pro Glu Leu Thr Ile Ile Gly Leu Pro Glu
            180                 185                 190 ggt aac tgg atc aca gtg agt aaa ggt cac gct acg ctg ggt ggc ccg      624
Gly Asn Trp Ile Thr Val Ser Lys Gly His Ala Thr Leu Gly Gly Pro
        195                 200                 205 aac acc act tat gtg ttt aag gct ggt gaa gaa gcg gtt ccg ctg gaa      672
Asn Thr Thr Tyr Val Phe Lys Ala Gly Glu Glu Ala Val Pro Leu Glu
    210                 215                 220 gct ggt cac cgt ttt taa                                              690
Ala Gly His Arg Phe
225
```

<210> SEQ ID NO 21
<211> LENGTH: 229
<212> TYPE: PRT
<213> ORGANISM: Escherichia coli

<400> SEQUENCE: 21

```
Met Glu Leu Leu Leu Leu Ser Asn Ser Thr Leu Pro Gly Lys Ala Trp
1               5                   10                  15

Leu Glu His Ala Leu Pro Leu Ile Ala Glu Gln Leu Gln Gly Arg Arg
            20                  25                  30

Ser Ala Val Phe Ile Pro Phe Ala Gly Val Thr Gln Thr Trp Asp Asp
        35                  40                  45

Tyr Thr Ala Lys Thr Ala Ala Val Leu Ala Pro Leu Gly Val Ser Val
    50                  55                  60

Thr Gly Ile His Ser Val Val Asp Pro Val Ala Ala Ile Glu Asn Ala
65                  70                  75                  80

Glu Ile Val Ile Val Gly Gly Gly Asn Thr Phe Gln Leu Leu Lys Gln
                85                  90                  95

Cys Arg Glu Arg Gly Leu Leu Ala Pro Ile Thr Asp Val Val Lys Arg
            100                 105                 110

Gly Ala Leu Tyr Ile Gly Trp Ser Ala Gly Ala Asn Leu Ala Cys Pro
        115                 120                 125

Thr Ile Arg Thr Thr Asn Asp Met Pro Ile Val Asp Pro Gln Gly Phe
    130                 135                 140

Asp Ala Leu Asn Leu Phe Pro Leu Gln Ile Asn Pro His Phe Thr Asn
145                 150                 155                 160

Ala Leu Pro Glu Gly His Lys Gly Glu Thr Arg Glu Gln Arg Ile Arg
                165                 170                 175

Glu Leu Leu Val Val Ala Pro Glu Leu Thr Ile Ile Gly Leu Pro Glu
            180                 185                 190

Gly Asn Trp Ile Thr Val Ser Lys Gly His Ala Thr Leu Gly Gly Pro
        195                 200                 205

Asn Thr Thr Tyr Val Phe Lys Ala Gly Glu Glu Ala Val Pro Leu Glu
    210                 215                 220

Ala Gly His Arg Phe
225
```

<210> SEQ ID NO 22
<211> LENGTH: 2613
<212> TYPE: DNA
<213> ORGANISM: Escherichia coli
<220> FEATURE:
<221> NAME/KEY: CDS
<222> LOCATION: (1)..(2613)

-continued

```
<400> SEQUENCE: 22 atg act caa cag cca caa gcc aaa tac cgt cac gat tat cgt gcg ccg      48
Met Thr Gln Gln Pro Gln Ala Lys Tyr Arg His Asp Tyr Arg Ala Pro
1               5                  10                  15 gat tac cag att act gat att gac ttg acc ttt gac ctc gac gcg caa      96
Asp Tyr Gln Ile Thr Asp Ile Asp Leu Thr Phe Asp Leu Asp Ala Gln
            20                  25                  30 aag acg gtc gtt acc gcg gtc agc cag gct gtc cgt cat ggt gca tca     144
Lys Thr Val Val Thr Ala Val Ser Gln Ala Val Arg His Gly Ala Ser
        35                  40                  45 gat gct ccc ctt cgt ctc aac ggc gaa gac ctc aaa ctg gtt tct gtt     192
Asp Ala Pro Leu Arg Leu Asn Gly Glu Asp Leu Lys Leu Val Ser Val
    50                  55                  60 cat att aat gat gag ccg tgg acc gcc tgg aaa gaa gaa gag ggc gca     240
His Ile Asn Asp Glu Pro Trp Thr Ala Trp Lys Glu Glu Glu Gly Ala
65                  70                  75                  80 ctg gtt atc agt aat ttg ccg gag cgt ttt acg ctt aag atc att aat     288
Leu Val Ile Ser Asn Leu Pro Glu Arg Phe Thr Leu Lys Ile Ile Asn
                85                  90                  95 gaa ata agc ccg gcg gcg aat acc gcg ctg gaa ggg ctt tat cag tca     336
Glu Ile Ser Pro Ala Ala Asn Thr Ala Leu Glu Gly Leu Tyr Gln Ser
            100                 105                 110 ggc gat gcg ctt tgc acc cag tgt gaa gcc gaa ggt ttc cgc cat att     384
Gly Asp Ala Leu Cys Thr Gln Cys Glu Ala Glu Gly Phe Arg His Ile
        115                 120                 125 acg tat tat ctc gac cgc ccg gac gtg ctg gcg cgt ttt acc acc aaa     432
Thr Tyr Tyr Leu Asp Arg Pro Asp Val Leu Ala Arg Phe Thr Thr Lys
    130                 135                 140 att att gcc gat aaa atc aaa tat ccc ttc ctg ctt tcc aat ggt aac     480
Ile Ile Ala Asp Lys Ile Lys Tyr Pro Phe Leu Leu Ser Asn Gly Asn
145                 150                 155                 160 cgc gtt gcg caa ggc gaa ctg gaa aac gga cgc cat tgg gta cag tgg     528
Arg Val Ala Gln Gly Glu Leu Glu Asn Gly Arg His Trp Val Gln Trp
                165                 170                 175 cag gac ccg ttc ccg aaa ccg tgc tac ctg ttt gcg ctg gtg gca ggc     576
Gln Asp Pro Phe Pro Lys Pro Cys Tyr Leu Phe Ala Leu Val Ala Gly
            180                 185                 190 gac ttt gat gta ctg cgc gat acc ttt acc acg cgt tct ggt cgc gaa     624
Asp Phe Asp Val Leu Arg Asp Thr Phe Thr Thr Arg Ser Gly Arg Glu
        195                 200                 205 gta gca ctg gag ctg tac gtc gat cgc ggc aac ctt gat cgc gcg ccg     672
Val Ala Leu Glu Leu Tyr Val Asp Arg Gly Asn Leu Asp Arg Ala Pro
    210                 215                 220 tgg gcg atg acc tcg ctg aaa aac tcc atg aaa tgg gat gaa gaa cgc     720
Trp Ala Met Thr Ser Leu Lys Asn Ser Met Lys Trp Asp Glu Glu Arg
225                 230                 235                 240 ttt ggc ctg gag tat gac ctc gac atc tat atg atc gtc gcg gtg gat     768
Phe Gly Leu Glu Tyr Asp Leu Asp Ile Tyr Met Ile Val Ala Val Asp
                245                 250                 255 ttc ttc aat atg ggc gca atg gag aat aag ggg ctg aat atc ttt aac     816
Phe Phe Asn Met Gly Ala Met Glu Asn Lys Gly Leu Asn Ile Phe Asn
            260                 265                 270 tcc aaa tat gtg ctg gcc cgc acc gac acc gcc acc gac aaa gat tac     864
Ser Lys Tyr Val Leu Ala Arg Thr Asp Thr Ala Thr Asp Lys Asp Tyr
        275                 280                 285 ctc gat att gaa cgc gtt atc ggc cat gaa tat ttc cat aac tgg acc     912
Leu Asp Ile Glu Arg Val Ile Gly His Glu Tyr Phe His Asn Trp Thr
    290                 295                 300 ggt aac cga gtg acc tgt cgc gac tgg ttc cag ctc agc ctg aaa gaa     960
```

```
        Gly Asn Arg Val Thr Cys Arg Asp Trp Phe Gln Leu Ser Leu Lys Glu
        305                 310                 315                 320 gtt tta acc gtc ttc cgc gat cag gag ttc agc tct gac ctt ggt tcc          1008
Gly Leu Thr Val Phe Arg Asp Gln Glu Phe Ser Ser Asp Leu Gly Ser
            325                 330                 335 cgc gca gtt aac cgc atc aat aat gta cgc acc atg cgc gga ttg cag          1056
Arg Ala Val Asn Arg Ile Asn Asn Val Arg Thr Met Arg Gly Leu Gln
                340                 345                 350 ttt gca gaa gac gcc agc ccg atg gcg cac ccg atc cgc ccg gat atg          1104
Phe Ala Glu Asp Ala Ser Pro Met Ala His Pro Ile Arg Pro Asp Met
            355                 360                 365 gtc att gag atg aac aac ttc tac acc ctg acc gtt tac gag aag ggc          1152
Val Ile Glu Met Asn Asn Phe Tyr Thr Leu Thr Val Tyr Glu Lys Gly
        370                 375                 380 gcg gaa gtg att cgc atg atc cac acc ctg ctt ggc gaa gaa aac ttc          1200
Ala Glu Val Ile Arg Met Ile His Thr Leu Leu Gly Glu Glu Asn Phe
385                 390                 395                 400 cag aaa ggg atg cag ctt tat ttc gag cgt cat gat ggt agt gca gcg          1248
Gln Lys Gly Met Gln Leu Tyr Phe Glu Arg His Asp Gly Ser Ala Ala
                405                 410                 415 acc tgt gac gac ttt gtg cag gcg atg gaa gat gcg tcg aat gtc gat          1296
Thr Cys Asp Asp Phe Val Gln Ala Met Glu Asp Ala Ser Asn Val Asp
            420                 425                 430 ctc tcc cat ttc cgc cgt tgg tac agc cag tcc ggt aca ccg att gtg          1344
Leu Ser His Phe Arg Arg Trp Tyr Ser Gln Ser Gly Thr Pro Ile Val
        435                 440                 445 acc gtc aaa gac gac tac aat ccg gaa acc gag cag tac acc ctg acc          1392
Thr Val Lys Asp Asp Tyr Asn Pro Glu Thr Glu Gln Tyr Thr Leu Thr
    450                 455                 460 atc agc cag cgc acg cca gcc acg ccg gat cag gca gaa aaa cag ccg          1440
Ile Ser Gln Arg Thr Pro Ala Thr Pro Asp Gln Ala Glu Lys Gln Pro
465                 470                 475                 480 ctg cat att ccg ttt gcc atc gaa ctg tat gat aac gaa ggc aaa gtg          1488
Leu His Ile Pro Phe Ala Ile Glu Leu Tyr Asp Asn Glu Gly Lys Val
                485                 490                 495 atc ccg ttg cag aaa ggc ggt cat ccg gtg aat tcc gtg ctg aac gtc          1536
Ile Pro Leu Gln Lys Gly Gly His Pro Val Asn Ser Val Leu Asn Val
            500                 505                 510 act cag gcg gaa cag acc ttt gtc ttt gat aat gtc tac ttc cag ccg          1584
Thr Gln Ala Glu Gln Thr Phe Val Phe Asp Asn Val Tyr Phe Gln Pro
        515                 520                 525 gtg cct gcg ctg ctg tgc gaa ttc tct gcg cca gtg aaa ctg gaa tat          1632
Val Pro Ala Leu Leu Cys Glu Phe Ser Ala Pro Val Lys Leu Glu Tyr
    530                 535                 540 aag tgg agc gat cag caa ctg acc ttc ctg atg cgt cat gcg cgt aat          1680
Lys Trp Ser Asp Gln Gln Leu Thr Phe Leu Met Arg His Ala Arg Asn
545                 550                 555                 560 gat ttc tcc cgc tgg gat gcg gcg caa agt ttg ctg gca acc tac atc          1728
Asp Phe Ser Arg Trp Asp Ala Ala Gln Ser Leu Leu Ala Thr Tyr Ile
                565                 570                 575 aag ctg aac gtc gcg cgt cat cag caa ggt cag ccg ctg tct ctg ccg          1776
Lys Leu Asn Val Ala Arg His Gln Gln Gly Gln Pro Leu Ser Leu Pro
            580                 585                 590 gtg cat gtg gct gat gct ttc cgc gcg gta ctg ctt gat gag aag att          1824
Val His Val Ala Asp Ala Phe Arg Ala Val Leu Leu Asp Glu Lys Ile
        595                 600                 605 gat cca gcg ctg gcg gca gaa atc ctg acg ctg cct tct gtc aat gaa          1872
Asp Pro Ala Leu Ala Ala Glu Ile Leu Thr Leu Pro Ser Val Asn Glu
    610                 615                 620
```

```
atg gct gaa ttg ttc gat atc atc gac ccg att gct att gcc gaa gta      1920
Met Ala Glu Leu Phe Asp Ile Ile Asp Pro Ile Ala Ile Ala Glu Val
625                 630                 635                 640 cgc gaa gca ctc act cgt act ctg gcg act gaa ctg gcg gat gag cta      1968
Arg Glu Ala Leu Thr Arg Thr Leu Ala Thr Glu Leu Ala Asp Glu Leu
                645                 650                 655 ctg gct att tac aac gcg aat tac cag agc gag tac cgt gtt gag cat      2016
Leu Ala Ile Tyr Asn Ala Asn Tyr Gln Ser Glu Tyr Arg Val Glu His
            660                 665                 670 gaa gat att gca aaa cgc act ctg cgt aat gcc tgc ctg cgt ttc ctc      2064
Glu Asp Ile Ala Lys Arg Thr Leu Arg Asn Ala Cys Leu Arg Phe Leu
        675                 680                 685 gct ttt ggt gaa acg cat ctg gct gat gtg ctg gtg agc aag cag ttc      2112
Ala Phe Gly Glu Thr His Leu Ala Asp Val Leu Val Ser Lys Gln Phe
    690                 695                 700 cac gaa gca aac aat atg act gat gcg ctg gcg gcg ctt tct gcg gcg      2160
His Glu Ala Asn Asn Met Thr Asp Ala Leu Ala Ala Leu Ser Ala Ala
705                 710                 715                 720 gtt gcc gca cag ctg cct tgc cgt gac gcg ctg atg cag gag tac gac      2208
Val Ala Ala Gln Leu Pro Cys Arg Asp Ala Leu Met Gln Glu Tyr Asp
                725                 730                 735 gac aag tgg cat cag aac ggt ctg gtg atg gat aaa tgg ttt atc ctg      2256
Asp Lys Trp His Gln Asn Gly Leu Val Met Asp Lys Trp Phe Ile Leu
            740                 745                 750 caa gcc acc agc ccg gcg gcg aat gtg ctg gag acg gtg cgc ggc ctg      2304
Gln Ala Thr Ser Pro Ala Ala Asn Val Leu Glu Thr Val Arg Gly Leu
        755                 760                 765 ttg cag cat cgc tca ttt acc atg agc aac ccg aac cgt att cgt tcg      2352
Leu Gln His Arg Ser Phe Thr Met Ser Asn Pro Asn Arg Ile Arg Ser
    770                 775                 780 ttg att ggc gcg ttt gcg ggc agc aat ccg gca gcg ttc cat gcc gaa      2400
Leu Ile Gly Ala Phe Ala Gly Ser Asn Pro Ala Ala Phe His Ala Glu
785                 790                 795                 800 gat ggc agc ggt tac ctg ttc ctg gtg gaa atg ctt acc gac ctc aac      2448
Asp Gly Ser Gly Tyr Leu Phe Leu Val Glu Met Leu Thr Asp Leu Asn
                805                 810                 815 agc cgt aac ccg cag gtg gct tca cgt ctg att gaa ccg ctg att cgc      2496
Ser Arg Asn Pro Gln Val Ala Ser Arg Leu Ile Glu Pro Leu Ile Arg
            820                 825                 830 ctg aaa cgt tac gat gcc aaa cgt cag gag aaa atg cgc gcg gcg ctg      2544
Leu Lys Arg Tyr Asp Ala Lys Arg Gln Glu Lys Met Arg Ala Ala Leu
        835                 840                 845 gaa cag ttg aaa ggg ctg gaa aat ctc tct ggc gat ctg tac gag aag      2592
Glu Gln Leu Lys Gly Leu Glu Asn Leu Ser Gly Asp Leu Tyr Glu Lys
    850                 855                 860 ata act aaa gca ctg gct tga                                          2613
Ile Thr Lys Ala Leu Ala
865                 870

<210> SEQ ID NO 23
<211> LENGTH: 870
<212> TYPE: PRT
<213> ORGANISM: Escherichia coli

<400> SEQUENCE: 23

Met Thr Gln Gln Pro Gln Ala Lys Tyr Arg His Asp Tyr Arg Ala Pro
1               5                   10                  15

Asp Tyr Gln Ile Thr Asp Ile Asp Leu Thr Phe Asp Leu Asp Ala Gln
            20                  25                  30

Lys Thr Val Val Thr Ala Val Ser Gln Ala Val Arg His Gly Ala Ser
```

```
              35                  40                  45
Asp Ala Pro Leu Arg Leu Asn Gly Glu Asp Leu Lys Leu Val Ser Val
 50                  55                  60

His Ile Asn Asp Glu Pro Trp Thr Ala Trp Lys Glu Glu Gly Ala
 65                  70                  75                  80

Leu Val Ile Ser Asn Leu Pro Glu Arg Phe Thr Leu Lys Ile Ile Asn
                 85                  90                  95

Glu Ile Ser Pro Ala Ala Asn Thr Ala Leu Glu Gly Leu Tyr Gln Ser
                100                 105                 110

Gly Asp Ala Leu Cys Thr Gln Cys Glu Ala Glu Gly Phe Arg His Ile
                115                 120                 125

Thr Tyr Tyr Leu Asp Arg Pro Asp Val Leu Ala Arg Phe Thr Thr Lys
                130                 135                 140

Ile Ile Ala Asp Lys Ile Lys Tyr Pro Phe Leu Leu Ser Asn Gly Asn
145                 150                 155                 160

Arg Val Ala Gln Gly Glu Leu Glu Asn Gly Arg His Trp Val Gln Trp
                165                 170                 175

Gln Asp Pro Phe Pro Lys Pro Cys Tyr Leu Phe Ala Leu Val Ala Gly
                180                 185                 190

Asp Phe Asp Val Leu Arg Asp Thr Phe Thr Thr Arg Ser Gly Arg Glu
                195                 200                 205

Val Ala Leu Glu Leu Tyr Val Asp Arg Gly Asn Leu Asp Arg Ala Pro
                210                 215                 220

Trp Ala Met Thr Ser Leu Lys Asn Ser Met Lys Trp Asp Glu Arg
225                 230                 235                 240

Phe Gly Leu Glu Tyr Asp Leu Asp Ile Tyr Met Ile Val Ala Val Asp
                245                 250                 255

Phe Phe Asn Met Gly Ala Met Glu Asn Lys Gly Leu Asn Ile Phe Asn
                260                 265                 270

Ser Lys Tyr Val Leu Ala Arg Thr Asp Thr Ala Thr Asp Lys Asp Tyr
                275                 280                 285

Leu Asp Ile Glu Arg Val Ile Gly His Glu Tyr Phe His Asn Trp Thr
                290                 295                 300

Gly Asn Arg Val Thr Cys Arg Asp Trp Phe Gln Leu Ser Leu Lys Glu
305                 310                 315                 320

Gly Leu Thr Val Phe Arg Asp Gln Glu Phe Ser Ser Asp Leu Gly Ser
                325                 330                 335

Arg Ala Val Asn Arg Ile Asn Asn Val Arg Thr Met Arg Gly Leu Gln
                340                 345                 350

Phe Ala Glu Asp Ala Ser Pro Met Ala His Pro Ile Arg Pro Asp Met
                355                 360                 365

Val Ile Glu Met Asn Asn Phe Tyr Thr Leu Thr Val Tyr Glu Lys Gly
                370                 375                 380

Ala Glu Val Ile Arg Met Ile His Thr Leu Leu Gly Glu Glu Asn Phe
385                 390                 395                 400

Gln Lys Gly Met Gln Leu Tyr Phe Glu Arg His Asp Gly Ser Ala Ala
                405                 410                 415

Thr Cys Asp Asp Phe Val Gln Ala Met Glu Asp Ala Ser Asn Val Asp
                420                 425                 430

Leu Ser His Phe Arg Arg Trp Tyr Ser Gln Ser Gly Thr Pro Ile Val
                435                 440                 445

Thr Val Lys Asp Asp Tyr Asn Pro Glu Thr Glu Gln Tyr Thr Leu Thr
                450                 455                 460
```

-continued

```
Ile Ser Gln Arg Thr Pro Ala Thr Pro Asp Gln Ala Glu Lys Gln Pro
465                 470                 475                 480

Leu His Ile Pro Phe Ala Ile Glu Leu Tyr Asp Asn Glu Gly Lys Val
                485                 490                 495

Ile Pro Leu Gln Lys Gly Gly His Pro Val Asn Ser Val Leu Asn Val
            500                 505                 510

Thr Gln Ala Glu Gln Thr Phe Val Phe Asp Asn Val Tyr Phe Gln Pro
        515                 520                 525

Val Pro Ala Leu Leu Cys Glu Phe Ser Ala Pro Val Lys Leu Glu Tyr
    530                 535                 540

Lys Trp Ser Asp Gln Leu Thr Phe Leu Met Arg His Ala Arg Asn
545                 550                 555                 560

Asp Phe Ser Arg Trp Asp Ala Ala Gln Ser Leu Leu Ala Thr Tyr Ile
                565                 570                 575

Lys Leu Asn Val Ala Arg His Gln Gln Gly Gln Pro Leu Ser Leu Pro
            580                 585                 590

Val His Val Ala Asp Ala Phe Arg Ala Val Leu Leu Asp Glu Lys Ile
        595                 600                 605

Asp Pro Ala Leu Ala Ala Glu Ile Leu Thr Leu Pro Ser Val Asn Glu
    610                 615                 620

Met Ala Glu Leu Phe Asp Ile Ile Asp Pro Ile Ala Ile Ala Glu Val
625                 630                 635                 640

Arg Glu Ala Leu Thr Arg Thr Leu Ala Thr Glu Leu Ala Asp Glu Leu
                645                 650                 655

Leu Ala Ile Tyr Asn Ala Asn Tyr Gln Ser Glu Tyr Arg Val Glu His
            660                 665                 670

Glu Asp Ile Ala Lys Arg Thr Leu Arg Asn Ala Cys Leu Arg Phe Leu
        675                 680                 685

Ala Phe Gly Glu Thr His Leu Ala Asp Val Leu Val Ser Lys Gln Phe
    690                 695                 700

His Glu Ala Asn Asn Met Thr Asp Ala Leu Ala Ala Leu Ser Ala Ala
705                 710                 715                 720

Val Ala Ala Gln Leu Pro Cys Arg Asp Ala Leu Met Gln Glu Tyr Asp
                725                 730                 735

Asp Lys Trp His Gln Asn Gly Leu Val Met Asp Lys Trp Phe Ile Leu
            740                 745                 750

Gln Ala Thr Ser Pro Ala Ala Asn Val Leu Glu Thr Val Arg Gly Leu
        755                 760                 765

Leu Gln His Arg Ser Phe Thr Met Ser Asn Pro Asn Arg Ile Arg Ser
    770                 775                 780

Leu Ile Gly Ala Phe Ala Gly Ser Asn Pro Ala Ala Phe His Ala Glu
785                 790                 795                 800

Asp Gly Ser Gly Tyr Leu Phe Leu Val Glu Met Leu Thr Asp Leu Asn
                805                 810                 815

Ser Arg Asn Pro Gln Val Ala Ser Arg Leu Ile Glu Pro Leu Ile Arg
            820                 825                 830

Leu Lys Arg Tyr Asp Ala Lys Arg Gln Glu Lys Met Arg Ala Ala Leu
        835                 840                 845

Glu Gln Leu Lys Gly Leu Glu Asn Leu Ser Gly Asp Leu Tyr Glu Lys
    850                 855                 860

Ile Thr Lys Ala Leu Ala
865                 870
```

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
cacaccgcat aaggtgcact ctc                                          23

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
gagagtgcac cttatgcggt gtg                                          23

<210> SEQ ID NO 26
<211> LENGTH: 27
<212> TYPE: DNA
<213> ORGANISM: Artificial Sequence
<220> FEATURE:
<223> OTHER INFORMATION: primer

<400> SEQUENCE: 26
gtaaggagga atgcatatga aaaatac                                      27

<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27 gtattttca tatgcattcc tccttac                                       27

<210> SEQ ID NO 28
<211> LENGTH: 29
<212> TYPE: DNA
<213> ORGANISM: Artificial Sequence
<220> FEATURE:
<223> OTHER INFORMATION: primer

<400> SEQUENCE: 28
gctctagaag tttgatatca atggcttat                                    29

<210> SEQ ID NO 29
<211> LENGTH: 45
<212> TYPE: DNA
<213> ORGANISM: Artificial Sequence
<220> FEATURE:
<223> OTHER INFORMATION: primer

<400> SEQUENCE: 29
gggaattcca tatgcattcc tccttaatcg atatcttctg gcgct                  45

<210> SEQ ID NO 30
<211> LENGTH: 37
<212> TYPE: DNA
<213> ORGANISM: Artificial Sequence
<220> FEATURE:
<223> OTHER INFORMATION: primer

<400> SEQUENCE: 30
gggaattcca tatgataaaa ccgacgtttt tacgccg                                    37

<210> SEQ ID NO 31
<211> LENGTH: 37
<212> TYPE: DNA
<213> ORGANISM: Artificial Sequence
<220> FEATURE:
<223> OTHER INFORMATION: primer

<400> SEQUENCE: 31
aaaactgcag ttagtacccc gccgttaaat catccac                                    37

<210> SEQ ID NO 32
<211> LENGTH: 68
<212> TYPE: DNA
<213> ORGANISM: Artificial Sequence
<220> FEATURE:
<223> OTHER INFORMATION: primer

<400> SEQUENCE: 32
atggagttta gtgtaaaaag cggtagcccg gagaaacagc ggagtgcctg tgaagcctgc           60
tttttat                                                                    68

<210> SEQ ID NO 33
<211> LENGTH: 68
<212> TYPE: DNA
<213> ORGANISM: Artificial Sequence
<220> FEATURE:
<223> OTHER INFORMATION: primer

<400> SEQUENCE: 33
ttactcttcg ccgttaaacc cagcgcggtt taacaggaac tgtgccagca cgctcaagtt           60
agtataaa                                                                   68

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
cgaatgctgg cagaacaaaa agtag                                                25

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tttagttatc cttctttgta                                                      20

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
actaatatgc cggatgcggc gtaaacgcct    30

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
ctctccggcg acaattactg gtggttaac    29

<210> SEQ ID NO 38
<211> LENGTH: 48
<212> TYPE: DNA
<213> ORGANISM: Artificial Sequence
<220> FEATURE:
<223> OTHER INFORMATION: primer

<400> SEQUENCE: 38
gcggcccttt tacaaagaag gataactaaa tgaagcctgc tttttttat    48

<210> SEQ ID NO 39
<211> LENGTH: 48
<212> TYPE: DNA
<213> ORGANISM: Artificial Sequence
<220> FEATURE:
<223> OTHER INFORMATION: primer

<400> SEQUENCE: 39
aggcgtttac gccgcatccg gcatattagt cgctcaagtt agtataaa    48

<210> SEQ ID NO 40
<211> LENGTH: 54
<212> TYPE: DNA
<213> ORGANISM: Artificial Sequence
<220> FEATURE:
<223> OTHER INFORMATION: primer

<400> SEQUENCE: 40
gtgtctgaac tgtctcaatt atctccacag ccgctgtgaa gcctgctttt ttat    54

<210> SEQ ID NO 41
<211> LENGTH: 54
<212> TYPE: DNA
<213> ORGANISM: Artificial Sequence
<220> FEATURE:
<223> OTHER INFORMATION: primer

<400> SEQUENCE: 41
cttcgccgga atttctttca gcagttcagt cagcagcgct caagttagta taaa    54

<210> SEQ ID NO 42
<211> LENGTH: 54
<212> TYPE: DNA
<213> ORGANISM: Artificial Sequence
<220> FEATURE:
<223> OTHER INFORMATION: primer

<400> SEQUENCE: 42
atggaactgc ttttattgag taactcgacg ctgccgtgaa gcctgctttt ttat    54

<210> SEQ ID NO 43
<211> LENGTH: 54
<212> TYPE: DNA
<213> ORGANISM: Artificial Sequence

```
<220> FEATURE:
<223> OTHER INFORMATION: primer

<400> SEQUENCE: 43
ggtgaccagc ttccagcgga accgcttctt caccagcgct caagttagta taaa          54

<210> SEQ ID NO 44
<211> LENGTH: 68
<212> TYPE: DNA
<213> ORGANISM: Artificial Sequence
<220> FEATURE:
<223> OTHER INFORMATION: primer

<400> SEQUENCE: 44
atgactcaac agccacaagc caaataccgt cacgattatc gtgcgccgga tgaagcctgc    60
tttttttat                                                            68

<210> SEQ ID NO 45
<211> LENGTH: 68
<212> TYPE: DNA
<213> ORGANISM: Artificial Sequence
<220> FEATURE:
<223> OTHER INFORMATION: primer

<400> SEQUENCE: 45
tcaagccagt gctttagtta tcttctcgta cagatcgcca gagagatttt cgctcaagtt    60
agtataaa                                                             68

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
ccgaacgttg cggggctggt gg                                             22

<210> SEQ ID NO 47
<211> LENGTH: 22
<212> TYPE: DNA
<213> ORGANISM: Artificial Sequence
<220> FEATURE:
<223> OTHER INFORMATION: primer

<400> SEQUENCE: 47
ccaccagccc cgcaacgttc gg                                             22

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
ccgaacgttg atgggctggt gg                                             22

<210> SEQ ID NO 49
<211> LENGTH: 22
<212> TYPE: DNA
<213> ORGANISM: Artificial Sequence
<220> FEATURE:
<223> OTHER INFORMATION: primer
```

<400> SEQUENCE: 49
ccaccagccc atcaacgttc gg                                              22

<210> SEQ ID NO 50
<211> LENGTH: 22
<212> TYPE: DNA
<213> ORGANISM: Artificial Sequence
<220> FEATURE:
<223> OTHER INFORMATION: primer

<400> SEQUENCE: 50
ccgaacgttg aagggctggt gg                                              22

<210> SEQ ID NO 51
<211> LENGTH: 22
<212> TYPE: DNA
<213> ORGANISM: Artificial Sequence
<220> FEATURE:
<223> OTHER INFORMATION: primer

<400> SEQUENCE: 51
ccaccagccc ttcaacgttc gg                                              22

<210> SEQ ID NO 52
<211> LENGTH: 22
<212> TYPE: DNA
<213> ORGANISM: Artificial Sequence
<220> FEATURE:
<223> OTHER INFORMATION: primer

<400> SEQUENCE: 52
ccgaacgtta acgggctggt gg                                              22

<210> SEQ ID NO 53
<211> LENGTH: 22
<212> TYPE: DNA
<213> ORGANISM: Artificial Sequence
<220> FEATURE:
<223> OTHER INFORMATION: primer

<400> SEQUENCE: 53
ccaccagccc gttaacgttc gg                                              22

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54
gcttaataac gcgatggatg atttc                                           25

<210> SEQ ID NO 55
<211> LENGTH: 25
<212> TYPE: DNA
<213> ORGANISM: Artificial Sequence
<220> FEATURE:
<223> OTHER INFORMATION: primer

<400> SEQUENCE: 55
gaaatcatcc atcgcgttat taagc                                           25

<210> SEQ ID NO 56
<211> LENGTH: 25

```
<212> TYPE: DNA
<213> ORGANISM: Artificial Sequence
<220> FEATURE:
<223> OTHER INFORMATION: primer

<400> SEQUENCE: 56
gcttaataac tgcatggatg atttc                                              25

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
gaaatcatcc atgcagttat taagc                                              25

<210> SEQ ID NO 58
<211> LENGTH: 25
<212> TYPE: DNA
<213> ORGANISM: Artificial Sequence
<220> FEATURE:
<223> OTHER INFORMATION: primer

<400> SEQUENCE: 58
gcttaataac gatatggatg atttc                                              25

<210> SEQ ID NO 59
<211> LENGTH: 25
<212> TYPE: DNA
<213> ORGANISM: Artificial Sequence
<220> FEATURE:
<223> OTHER INFORMATION: primer

<400> SEQUENCE: 59
gaaatcatcc atatcgttat taagc                                              25

<210> SEQ ID NO 60
<211> LENGTH: 25
<212> TYPE: DNA
<213> ORGANISM: Artificial Sequence
<220> FEATURE:
<223> OTHER INFORMATION: primer

<400> SEQUENCE: 60
gcttaataac gaaatggatg atttc                                              25

<210> SEQ ID NO 61
<211> LENGTH: 25
<212> TYPE: DNA
<213> ORGANISM: Artificial Sequence
<220> FEATURE:
<223> OTHER INFORMATION: primer

<400> SEQUENCE: 61
gaaatcatcc atttcgttat taagc                                              25

<210> SEQ ID NO 62
<211> LENGTH: 25
<212> TYPE: DNA
<213> ORGANISM: Artificial Sequence
<220> FEATURE:
<223> OTHER INFORMATION: primer

<400> SEQUENCE: 62
```
gcttaataac tttatggatg atttc					25

<210> SEQ ID NO 63
<211> LENGTH: 25
<212> TYPE: DNA
<213> ORGANISM: Artificial Sequence
<220> FEATURE:
<223> OTHER INFORMATION: primer

<400> SEQUENCE: 63
gaaatcatcc ataaagttat taagc					25

<210> SEQ ID NO 64
<211> LENGTH: 25
<212> TYPE: DNA
<213> ORGANISM: Artificial Sequence
<220> FEATURE:
<223> OTHER INFORMATION: primer

<400> SEQUENCE: 64
gcttaataac ggcatggatg atttc					25

<210> SEQ ID NO 65
<211> LENGTH: 25
<212> TYPE: DNA
<213> ORGANISM: Artificial Sequence
<220> FEATURE:
<223> OTHER INFORMATION: primer

<400> SEQUENCE: 65
gaaatcatcc atgccgttat taagc					25

<210> SEQ ID NO 66
<211> LENGTH: 25
<212> TYPE: DNA
<213> ORGANISM: Artificial Sequence
<220> FEATURE:
<223> OTHER INFORMATION: primer

<400> SEQUENCE: 66
gcttaataac catatggatg atttc					25

<210> SEQ ID NO 67
<211> LENGTH: 25
<212> TYPE: DNA
<213> ORGANISM: Artificial Sequence
<220> FEATURE:
<223> OTHER INFORMATION: primer

<400> SEQUENCE: 67
gaaatcatcc atatggttat taagc					25

<210> SEQ ID NO 68
<211> LENGTH: 25
<212> TYPE: DNA
<213> ORGANISM: Artificial Sequence
<220> FEATURE:
<223> OTHER INFORMATION: primer

<400> SEQUENCE: 68
gcttaataac attatggatg atttc					25

<210> SEQ ID NO 69
<211> LENGTH: 25
<212> TYPE: DNA
<213> ORGANISM: Artificial Sequence
<220> FEATURE:
<223> OTHER INFORMATION: primer

<400> SEQUENCE: 69
gaaatcatcc ataatgttat taagc                                         25

<210> SEQ ID NO 70
<211> LENGTH: 25
<212> TYPE: DNA
<213> ORGANISM: Artificial Sequence
<220> FEATURE:
<223> OTHER INFORMATION: primer

<400> SEQUENCE: 70
gcttaataac aaaatggatg atttc                                         25

<210> SEQ ID NO 71
<211> LENGTH: 25
<212> TYPE: DNA
<213> ORGANISM: Artificial Sequence
<220> FEATURE:
<223> OTHER INFORMATION: primer

<400> SEQUENCE: 71
gaaatcatcc attttgttat taagc                                         25

<210> SEQ ID NO 72
<211> LENGTH: 25
<212> TYPE: DNA
<213> ORGANISM: Artificial Sequence
<220> FEATURE:
<223> OTHER INFORMATION: primer

<400> SEQUENCE: 72
gcttaataac ctgatggatg atttc                                         25

<210> SEQ ID NO 73
<211> LENGTH: 25
<212> TYPE: DNA
<213> ORGANISM: Artificial Sequence
<220> FEATURE:
<223> OTHER INFORMATION: primer

<400> SEQUENCE: 73
gaaatcatcc atcaggttat taagc                                         25

<210> SEQ ID NO 74
<211> LENGTH: 25
<212> TYPE: DNA
<213> ORGANISM: Artificial Sequence
<220> FEATURE:
<223> OTHER INFORMATION: primer

<400> SEQUENCE: 74
gcttaataac atgatggatg atttc                                         25

<210> SEQ ID NO 75
<211> LENGTH: 25
<212> TYPE: DNA
<213> ORGANISM: Artificial Sequence
<220> FEATURE:
<223> OTHER INFORMATION: primer

<400> SEQUENCE: 75
gaaatcatcc atcatgttat taagc                                         25

```
<210> SEQ ID NO 76
<211> LENGTH: 25
<212> TYPE: DNA
<213> ORGANISM: Artificial Sequence
<220> FEATURE:
<223> OTHER INFORMATION: primer

<400> SEQUENCE: 76
gcttaataac aacatggatg atttc                                      25

<210> SEQ ID NO 77
<211> LENGTH: 25
<212> TYPE: DNA
<213> ORGANISM: Artificial Sequence
<220> FEATURE:
<223> OTHER INFORMATION: primer

<400> SEQUENCE: 77
gaaatcatcc atgttgttat taagc                                      25

<210> SEQ ID NO 78
<211> LENGTH: 25
<212> TYPE: DNA
<213> ORGANISM: Artificial Sequence
<220> FEATURE:
<223> OTHER INFORMATION: primer

<400> SEQUENCE: 78
gcttaataac ccgatggatg atttc                                      25

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
gaaatcatcc atcgggttat taagc                                      25

<210> SEQ ID NO 80
<211> LENGTH: 25
<212> TYPE: DNA
<213> ORGANISM: Artificial Sequence
<220> FEATURE:
<223> OTHER INFORMATION: primer

<400> SEQUENCE: 80
gcttaataac cgcatggatg atttc                                      25

<210> SEQ ID NO 81
<211> LENGTH: 25
<212> TYPE: DNA
<213> ORGANISM: Artificial Sequence
<220> FEATURE:
<223> OTHER INFORMATION: primer

<400> SEQUENCE: 81
gaaatcatcc atgcggttat taagc                                      25

<210> SEQ ID NO 82
<211> LENGTH: 25
<212> TYPE: DNA
<213> ORGANISM: Artificial Sequence
<220> FEATURE:
<223> OTHER INFORMATION: primer
```

```
<400> SEQUENCE: 82
gcttaataac agcatggatg atttc                                              25

<210> SEQ ID NO 83
<211> LENGTH: 25
<212> TYPE: DNA
<213> ORGANISM: Artificial Sequence
<220> FEATURE:
<223> OTHER INFORMATION: primer

<400> SEQUENCE: 83
gaaatcatcc atgctgttat taagc                                              25

<210> SEQ ID NO 84
<211> LENGTH: 25
<212> TYPE: DNA
<213> ORGANISM: Artificial Sequence
<220> FEATURE:
<223> OTHER INFORMATION: primer

<400> SEQUENCE: 84
gcttaataac accatggatg atttc                                              25

<210> SEQ ID NO 85
<211> LENGTH: 25
<212> TYPE: DNA
<213> ORGANISM: Artificial Sequence
<220> FEATURE:
<223> OTHER INFORMATION: primer

<400> SEQUENCE: 85
gaaatcatcc atggtgttat taagc                                              25

<210> SEQ ID NO 86
<211> LENGTH: 25
<212> TYPE: DNA
<213> ORGANISM: Artificial Sequence
<220> FEATURE:
<223> OTHER INFORMATION: primer

<400> SEQUENCE: 86
gcttaataac gtgatggatg atttc                                              25

<210> SEQ ID NO 87
<211> LENGTH: 25
<212> TYPE: DNA
<213> ORGANISM: Artificial Sequence
<220> FEATURE:
<223> OTHER INFORMATION: primer

<400> SEQUENCE: 87
gaaatcatcc atcacgttat taagc                                              25

<210> SEQ ID NO 88
<211> LENGTH: 25
<212> TYPE: DNA
<213> ORGANISM: Artificial Sequence
<220> FEATURE:
<223> OTHER INFORMATION: primer

<400> SEQUENCE: 88
gcttaataac tggatggatg atttc                                              25

<210> SEQ ID NO 89
```

```
<211> LENGTH: 25
<212> TYPE: DNA
<213> ORGANISM: Artificial Sequence
<220> FEATURE:
<223> OTHER INFORMATION: primer

<400> SEQUENCE: 89
gaaatcatcc atccagttat taagc                                    25

<210> SEQ ID NO 90
<211> LENGTH: 25
<212> TYPE: DNA
<213> ORGANISM: Artificial Sequence
<220> FEATURE:
<223> OTHER INFORMATION: primer

<400> SEQUENCE: 90
gcttaataac tatatggatg atttc                                    25

<210> SEQ ID NO 91
<211> LENGTH: 25
<212> TYPE: DNA
<213> ORGANISM: Artificial Sequence
<220> FEATURE:
<223> OTHER INFORMATION: primer

<400> SEQUENCE: 91
gaaatcatcc atatagttat taagc                                    25

<210> SEQ ID NO 92
<211> LENGTH: 22
<212> TYPE: DNA
<213> ORGANISM: Artificial Sequence
<220> FEATURE:
<223> OTHER INFORMATION: primer

<400> SEQUENCE: 92
ccagatggat gcgttctccg cc                                       22

<210> SEQ ID NO 93
<211> LENGTH: 22
<212> TYPE: DNA
<213> ORGANISM: Artificial Sequence
<220> FEATURE:
<223> OTHER INFORMATION: primer

<400> SEQUENCE: 93
ggcggagaac gcatccatct gg                                       22

<210> SEQ ID NO 94
<211> LENGTH: 22
<212> TYPE: DNA
<213> ORGANISM: Artificial Sequence
<220> FEATURE:
<223> OTHER INFORMATION: primer

<400> SEQUENCE: 94
ccagatggat tgcttctccg cc                                       22

<210> SEQ ID NO 95
<211> LENGTH: 22
<212> TYPE: DNA
<213> ORGANISM: Artificial Sequence
<220> FEATURE:
<223> OTHER INFORMATION: primer

<400> SEQUENCE: 95
```
ggcggagaag caatccatct gg                                              22

<210> SEQ ID NO 96
<211> LENGTH: 22
<212> TYPE: DNA
<213> ORGANISM: Artificial Sequence
<220> FEATURE:
<223> OTHER INFORMATION: primer

<400> SEQUENCE: 96
ccagatggat gaattctccg cc                                              22

<210> SEQ ID NO 97
<211> LENGTH: 22
<212> TYPE: DNA
<213> ORGANISM: Artificial Sequence
<220> FEATURE:
<223> OTHER INFORMATION: primer

<400> SEQUENCE: 97
ggcggagaat tcatccatct gg                                              22

<210> SEQ ID NO 98
<211> LENGTH: 22
<212> TYPE: DNA
<213> ORGANISM: Artificial Sequence
<220> FEATURE:
<223> OTHER INFORMATION: primer

<400> SEQUENCE: 98
ccagatggat tttttctccg cc                                              22

<210> SEQ ID NO 99
<211> LENGTH: 22
<212> TYPE: DNA
<213> ORGANISM: Artificial Sequence
<220> FEATURE:
<223> OTHER INFORMATION: primer

<400> SEQUENCE: 99
ggcggagaaa aaatccatct gg                                              22

<210> SEQ ID NO 100
<211> LENGTH: 22
<212> TYPE: DNA
<213> ORGANISM: Artificial Sequence
<220> FEATURE:
<223> OTHER INFORMATION: primer

<400> SEQUENCE: 100
ccagatggat ggcttctccg cc                                              22

<210> SEQ ID NO 101
<211> LENGTH: 22
<212> TYPE: DNA
<213> ORGANISM: Artificial Sequence
<220> FEATURE:
<223> OTHER INFORMATION: primer

<400> SEQUENCE: 101
ggcggagaag ccatccatct gg                                              22

<210> SEQ ID NO 102
<211> LENGTH: 22
<212> TYPE: DNA

```
<213> ORGANISM: Artificial Sequence
<220> FEATURE:
<223> OTHER INFORMATION: primer

<400> SEQUENCE: 102
ccagatggat catttctccg cc                                              22

<210> SEQ ID NO 103
<211> LENGTH: 22
<212> TYPE: DNA
<213> ORGANISM: Artificial Sequence
<220> FEATURE:
<223> OTHER INFORMATION: primer

<400> SEQUENCE: 103
ggcggagaaa tgatccatct gg                                              22

<210> SEQ ID NO 104
<211> LENGTH: 22
<212> TYPE: DNA
<213> ORGANISM: Artificial Sequence
<220> FEATURE:
<223> OTHER INFORMATION: primer

<400> SEQUENCE: 104
ccagatggat attttctccg cc                                              22

<210> SEQ ID NO 105
<211> LENGTH: 22
<212> TYPE: DNA
<213> ORGANISM: Artificial Sequence
<220> FEATURE:
<223> OTHER INFORMATION: primer

<400> SEQUENCE: 105
ggcggagaaa atatccatct gg                                              22

<210> SEQ ID NO 106
<211> LENGTH: 22
<212> TYPE: DNA
<213> ORGANISM: Artificial Sequence
<220> FEATURE:
<223> OTHER INFORMATION: primer

<400> SEQUENCE: 106
ccagatggat aaattctccg cc                                              22

<210> SEQ ID NO 107
<211> LENGTH: 22
<212> TYPE: DNA
<213> ORGANISM: Artificial Sequence
<220> FEATURE:
<223> OTHER INFORMATION: primer

<400> SEQUENCE: 107
ggcggagaat ttatccatct gg                                              22

<210> SEQ ID NO 108
<211> LENGTH: 22
<212> TYPE: DNA
<213> ORGANISM: Artificial Sequence
<220> FEATURE:
<223> OTHER INFORMATION: primer

<400> SEQUENCE: 108
ccagatggat ctgttctccg cc                                              22
```

```
<210> SEQ ID NO 109
<211> LENGTH: 22
<212> TYPE: DNA
<213> ORGANISM: Artificial Sequence
<220> FEATURE:
<223> OTHER INFORMATION: primer

<400> SEQUENCE: 109
ggcggagaac agatccatct gg                                                22

<210> SEQ ID NO 110
<211> LENGTH: 22
<212> TYPE: DNA
<213> ORGANISM: Artificial Sequence
<220> FEATURE:
<223> OTHER INFORMATION: primer

<400> SEQUENCE: 110
ccagatggat atgttctccg cc                                                22

<210> SEQ ID NO 111
<211> LENGTH: 22
<212> TYPE: DNA
<213> ORGANISM: Artificial Sequence
<220> FEATURE:
<223> OTHER INFORMATION: primer

<400> SEQUENCE: 111
ggcggagaac atatccatct gg                                                22

<210> SEQ ID NO 112
<211> LENGTH: 22
<212> TYPE: DNA
<213> ORGANISM: Artificial Sequence
<220> FEATURE:
<223> OTHER INFORMATION: primer

<400> SEQUENCE: 112
ccagatggat aacttctccg cc                                                22

<210> SEQ ID NO 113
<211> LENGTH: 22
<212> TYPE: DNA
<213> ORGANISM: Artificial Sequence
<220> FEATURE:
<223> OTHER INFORMATION: primer

<400> SEQUENCE: 113
ggcggagaag ttatccatct gg                                                22

<210> SEQ ID NO 114
<211> LENGTH: 22
<212> TYPE: DNA
<213> ORGANISM: Artificial Sequence
<220> FEATURE:
<223> OTHER INFORMATION: primer

<400> SEQUENCE: 114
ccagatggat ccgttctccg cc                                                22

<210> SEQ ID NO 115
<211> LENGTH: 22
<212> TYPE: DNA
<213> ORGANISM: Artificial Sequence
<220> FEATURE:
```

<223> OTHER INFORMATION: primer

<400> SEQUENCE: 115
ggcggagaac ggatccatct gg                                              22

<210> SEQ ID NO 116
<211> LENGTH: 22
<212> TYPE: DNA
<213> ORGANISM: Artificial Sequence
<220> FEATURE:
<223> OTHER INFORMATION: primer

<400> SEQUENCE: 116
ccagatggat cagttctccg cc                                              22

<210> SEQ ID NO 117
<211> LENGTH: 22
<212> TYPE: DNA
<213> ORGANISM: Artificial Sequence
<220> FEATURE:
<223> OTHER INFORMATION: primer

<400> SEQUENCE: 117
ggcggagaac tgatccatct gg                                              22

<210> SEQ ID NO 118
<211> LENGTH: 22
<212> TYPE: DNA
<213> ORGANISM: Artificial Sequence
<220> FEATURE:
<223> OTHER INFORMATION: primer

<400> SEQUENCE: 118
ccagatggat cgcttctccg cc                                              22

<210> SEQ ID NO 119
<211> LENGTH: 22
<212> TYPE: DNA
<213> ORGANISM: Artificial Sequence
<220> FEATURE:
<223> OTHER INFORMATION: primer

<400> SEQUENCE: 119
ggcggagaag cgatccatct gg                                              22

<210> SEQ ID NO 120
<211> LENGTH: 22
<212> TYPE: DNA
<213> ORGANISM: Artificial Sequence
<220> FEATURE:
<223> OTHER INFORMATION: primer

<400> SEQUENCE: 120
ccagatggat agcttctccg cc                                              22

<210> SEQ ID NO 121
<211> LENGTH: 22
<212> TYPE: DNA
<213> ORGANISM: Artificial Sequence
<220> FEATURE:
<223> OTHER INFORMATION: primer

<400> SEQUENCE: 121
ggcggagaag ctatccatct gg                                              22

```
<210> SEQ ID NO 122
<211> LENGTH: 22
<212> TYPE: DNA
<213> ORGANISM: Artificial Sequence
<220> FEATURE:
<223> OTHER INFORMATION: primer

<400> SEQUENCE: 122
ccagatggat accttctccg cc                                              22

<210> SEQ ID NO 123
<211> LENGTH: 22
<212> TYPE: DNA
<213> ORGANISM: Artificial Sequence
<220> FEATURE:
<223> OTHER INFORMATION: primer

<400> SEQUENCE: 123
ggcggagaag gtatccatct gg                                              22

<210> SEQ ID NO 124
<211> LENGTH: 22
<212> TYPE: DNA
<213> ORGANISM: Artificial Sequence
<220> FEATURE:
<223> OTHER INFORMATION: primer

<400> SEQUENCE: 124
ccagatggat gtgttctccg cc                                              22

<210> SEQ ID NO 125
<211> LENGTH: 22
<212> TYPE: DNA
<213> ORGANISM: Artificial Sequence
<220> FEATURE:
<223> OTHER INFORMATION: primer

<400> SEQUENCE: 125
ggcggagaac acatccatct gg                                              22

<210> SEQ ID NO 126
<211> LENGTH: 22
<212> TYPE: DNA
<213> ORGANISM: Artificial Sequence
<220> FEATURE:
<223> OTHER INFORMATION: primer

<400> SEQUENCE: 126
ccagatggat tggttctccg cc                                              22

<210> SEQ ID NO 127
<211> LENGTH: 22
<212> TYPE: DNA
<213> ORGANISM: Artificial Sequence
<220> FEATURE:
<223> OTHER INFORMATION: primer

<400> SEQUENCE: 127
ggcggagaac caatccatct gg                                              22

<210> SEQ ID NO 128
<211> LENGTH: 22
<212> TYPE: DNA
<213> ORGANISM: Artificial Sequence
<220> FEATURE:
<223> OTHER INFORMATION: primer
```

```
<400> SEQUENCE: 128
ccagatggat tatttctccg cc                                          22

<210> SEQ ID NO 129
<211> LENGTH: 22
<212> TYPE: DNA
<213> ORGANISM: Artificial Sequence
<220> FEATURE:
<223> OTHER INFORMATION: primer

<400> SEQUENCE: 129
ggcggagaaa taatccatct gg                                          22

<210> SEQ ID NO 130
<211> LENGTH: 24
<212> TYPE: DNA
<213> ORGANISM: Artificial Sequence
<220> FEATURE:
<223> OTHER INFORMATION: primer

<400> SEQUENCE: 130
gcagcccgcg gcgaaactgg cacg                                        24

<210> SEQ ID NO 131
<211> LENGTH: 24
<212> TYPE: DNA
<213> ORGANISM: Artificial Sequence
<220> FEATURE:
<223> OTHER INFORMATION: primer

<400> SEQUENCE: 131
cgtgccagtt tcgccgcggg ctgc                                        24

<210> SEQ ID NO 132
<211> LENGTH: 24
<212> TYPE: DNA
<213> ORGANISM: Artificial Sequence
<220> FEATURE:
<223> OTHER INFORMATION: primer

<400> SEQUENCE: 132
gcagcccgcg attaaactgg cacg                                        24

<210> SEQ ID NO 133
<211> LENGTH: 24
<212> TYPE: DNA
<213> ORGANISM: Artificial Sequence
<220> FEATURE:
<223> OTHER INFORMATION: primer

<400> SEQUENCE: 133
cgtgccagtt taatcgcggg ctgc                                        24

<210> SEQ ID NO 134
<211> LENGTH: 24
<212> TYPE: DNA
<213> ORGANISM: Artificial Sequence
<220> FEATURE:
<223> OTHER INFORMATION: primer

<400> SEQUENCE: 134
gcagcccgcg ctgaaactgg cacg                                        24

<210> SEQ ID NO 135
<211> LENGTH: 24
```

-continued

```
<212> TYPE: DNA
<213> ORGANISM: Artificial Sequence
<220> FEATURE:
<223> OTHER INFORMATION: primer

<400> SEQUENCE: 135
cgtgccagtt tcagcgcggg ctgc                                              24

<210> SEQ ID NO 136
<211> LENGTH: 24
<212> TYPE: DNA
<213> ORGANISM: Artificial Sequence
<220> FEATURE:
<223> OTHER INFORMATION: primer

<400> SEQUENCE: 136
gcagcccgcg atgaaactgg cacg                                              24

<210> SEQ ID NO 137
<211> LENGTH: 24
<212> TYPE: DNA
<213> ORGANISM: Artificial Sequence
<220> FEATURE:
<223> OTHER INFORMATION: primer

<400> SEQUENCE: 137
cgtgccagtt tcatcgcggg ctgc                                              24

<210> SEQ ID NO 138
<211> LENGTH: 24
<212> TYPE: DNA
<213> ORGANISM: Artificial Sequence
<220> FEATURE:
<223> OTHER INFORMATION: primer

<400> SEQUENCE: 138
gcagcccgcg gtgaaactgg cacg                                              24

<210> SEQ ID NO 139
<211> LENGTH: 24
<212> TYPE: DNA
<213> ORGANISM: Artificial Sequence
<220> FEATURE:
<223> OTHER INFORMATION: primer

<400> SEQUENCE: 139
cgtgccagtt tcaccgcggg ctgc                                              24

<210> SEQ ID NO 140
<211> LENGTH: 24
<212> TYPE: DNA
<213> ORGANISM: Artificial Sequence
<220> FEATURE:
<223> OTHER INFORMATION: primer

<400> SEQUENCE: 140
gcagcccgcg tggaaactgg cacg                                              24

<210> SEQ ID NO 141
<211> LENGTH: 24
<212> TYPE: DNA
<213> ORGANISM: Artificial Sequence
<220> FEATURE:
<223> OTHER INFORMATION: primer

<400> SEQUENCE: 141
```
cgtgccagtt tccacgcggg ctgc                                                24

<210> SEQ ID NO 142
<211> LENGTH: 24
<212> TYPE: DNA
<213> ORGANISM: Artificial Sequence
<220> FEATURE:
<223> OTHER INFORMATION: primer

<400> SEQUENCE: 142
gcagcccgcg tataaactgg cacg                                                24

<210> SEQ ID NO 143
<211> LENGTH: 24
<212> TYPE: DNA
<213> ORGANISM: Artificial Sequence
<220> FEATURE:
<223> OTHER INFORMATION: primer

<400> SEQUENCE: 143
cgtgccagtt tatacgcggg ctgc                                                24

<210> SEQ ID NO 144
<211> LENGTH: 23
<212> TYPE: DNA
<213> ORGANISM: Artificial Sequence
<220> FEATURE:
<223> OTHER INFORMATION: primer

<400> SEQUENCE: 144
gtggtgaaaa ttggtaaaac ctg                                                 23

<210> SEQ ID NO 145
<211> LENGTH: 23
<212> TYPE: DNA
<213> ORGANISM: Artificial Sequence
<220> FEATURE:
<223> OTHER INFORMATION: primer

<400> SEQUENCE: 145
caggttttac caattttcac cac                                                 23

<210> SEQ ID NO 146
<211> LENGTH: 23
<212> TYPE: DNA
<213> ORGANISM: Artificial Sequence
<220> FEATURE:
<223> OTHER INFORMATION: primer

<400> SEQUENCE: 146
ctataaaggc cgcattgcgg aac                                                 23

<210> SEQ ID NO 147
<211> LENGTH: 23
<212> TYPE: DNA
<213> ORGANISM: Artificial Sequence
<220> FEATURE:
<223> OTHER INFORMATION: primer

<400> SEQUENCE: 147
gttccgcaat gcggccttta tag                                                 23

<210> SEQ ID NO 148
<211> LENGTH: 29
<212> TYPE: DNA
<213> ORGANISM: Artificial Sequence -continued
<220> FEATURE:
<223> OTHER INFORMATION: primer

<400> SEQUENCE: 148
gatccatatc ctgcaaatcc tcaatattc                                29

<210> SEQ ID NO 149
<211> LENGTH: 29
<212> TYPE: DNA
<213> ORGANISM: Artificial Sequence
<220> FEATURE:
<223> OTHER INFORMATION: primer

<400> SEQUENCE: 149
gaatattgag gatttgcagg atatggatc                                29

<210> SEQ ID NO 150
<211> LENGTH: 23
<212> TYPE: DNA
<213> ORGANISM: Artificial Sequence
<220> FEATURE:
<223> OTHER INFORMATION: primer

<400> SEQUENCE: 150
gctgaacacc aacttcggta cgg                                      23

<210> SEQ ID NO 151
<211> LENGTH: 23
<212> TYPE: DNA
<213> ORGANISM: Artificial Sequence
<220> FEATURE:
<223> OTHER INFORMATION: primer

<400> SEQUENCE: 151
ccgtaccgaa gttggtgttc agc                                      23

<210> SEQ ID NO 152
<211> LENGTH: 26
<212> TYPE: DNA
<213> ORGANISM: Artificial Sequence
<220> FEATURE:
<223> OTHER INFORMATION: primer

<400> SEQUENCE: 152
gtagcccagg cagcagccgg atcatc                                   26

<210> SEQ ID NO 153
<211> LENGTH: 26
<212> TYPE: DNA
<213> ORGANISM: Artificial Sequence
<220> FEATURE:
<223> OTHER INFORMATION: primer

<400> SEQUENCE: 153
gatgatccgg ctgctgcctg ggctac                                   26

<210> SEQ ID NO 154
<211> LENGTH: 26
<212> TYPE: DNA
<213> ORGANISM: Artificial Sequence
<220> FEATURE:
<223> OTHER INFORMATION: primer

<400> SEQUENCE: 154
gtgatgccaa cagcgtcggg ccgaac                                   26

<210> SEQ ID NO 155
<211> LENGTH: 26
<212> TYPE: DNA
<213> ORGANISM: Artificial Sequence
<220> FEATURE:
<223> OTHER INFORMATION: primer

<400> SEQUENCE: 155
gttcggcccg acgctgttgg catcac                                        26

<210> SEQ ID NO 156
<211> LENGTH: 23
<212> TYPE: DNA
<213> ORGANISM: Artificial Sequence
<220> FEATURE:
<223> OTHER INFORMATION: primer

<400> SEQUENCE: 156
cgtaccgaac gcggaagggc tgg                                           23

<210> SEQ ID NO 157
<211> LENGTH: 23
<212> TYPE: DNA
<213> ORGANISM: Artificial Sequence
<220> FEATURE:
<223> OTHER INFORMATION: primer

<400> SEQUENCE: 157
ccagcccttc cgcgttcggt acg                                           23

<210> SEQ ID NO 158
<211> LENGTH: 23
<212> TYPE: DNA
<213> ORGANISM: Artificial Sequence
<220> FEATURE:
<223> OTHER INFORMATION: primer

<400> SEQUENCE: 158
gctgaacacc gcgttcggta cgg                                           23

<210> SEQ ID NO 159
<211> LENGTH: 23
<212> TYPE: DNA
<213> ORGANISM: Artificial Sequence
<220> FEATURE:
<223> OTHER INFORMATION: primer

<400> SEQUENCE: 159
ccgtaccgaa cgcggtgttc agc                                           23

<210> SEQ ID NO 160
<211> LENGTH: 23
<212> TYPE: DNA
<213> ORGANISM: Artificial Sequence
<220> FEATURE:
<223> OTHER INFORMATION: primer

<400> SEQUENCE: 160
gctgaacacc catttcggta cgg                                           23

<210> SEQ ID NO 161
<211> LENGTH: 23
<212> TYPE: DNA
<213> ORGANISM: Artificial Sequence
<220> FEATURE:
<223> OTHER INFORMATION: primer -continued

<400> SEQUENCE: 161
ccgtaccgaa atgggtgttc agc                                                    23

<210> SEQ ID NO 162
<211> LENGTH: 26
<212> TYPE: DNA
<213> ORGANISM: Artificial Sequence
<220> FEATURE:
<223> OTHER INFORMATION: primer

<400> SEQUENCE: 162
gtagcccagg cgcgagccgg atcatc                                                 26

<210> SEQ ID NO 163
<211> LENGTH: 26
<212> TYPE: DNA
<213> ORGANISM: Artificial Sequence
<220> FEATURE:
<223> OTHER INFORMATION: primer

<400> SEQUENCE: 163
gatgatccgg ctcgcgcctg ggctac                                                 26

<210> SEQ ID NO 164
<211> LENGTH: 26
<212> TYPE: DNA
<213> ORGANISM: Artificial Sequence
<220> FEATURE:
<223> OTHER INFORMATION: primer

<400> SEQUENCE: 164
gtagcccagg cgaaagccgg atcatc                                                 26

<210> SEQ ID NO 165
<211> LENGTH: 26
<212> TYPE: DNA
<213> ORGANISM: Artificial Sequence
<220> FEATURE:
<223> OTHER INFORMATION: primer

<400> SEQUENCE: 165
gatgatccgg ctttcgcctg ggctac                                                 26

<210> SEQ ID NO 166
<211> LENGTH: 21
<212> TYPE: DNA
<213> ORGANISM: Artificial Sequence
<220> FEATURE:
<223> OTHER INFORMATION: primer

<400> SEQUENCE: 166
ggtgtggaga aagatgtctt c                                                      21

<210> SEQ ID NO 167
<211> LENGTH: 21
<212> TYPE: DNA
<213> ORGANISM: Artificial Sequence
<220> FEATURE:
<223> OTHER INFORMATION: primer

<400> SEQUENCE: 167
gaagacatct ttctccacac c                                                      21

<210> SEQ ID NO 168

-continued

<210> SEQ ID NO 168
<211> LENGTH: 23
<212> TYPE: DNA
<213> ORGANISM: Artificial Sequence
<220> FEATURE:
<223> OTHER INFORMATION: primer

<400> SEQUENCE: 168
cgatatgttc gtggatgatc agg                                          23

<210> SEQ ID NO 169
<211> LENGTH: 23
<212> TYPE: DNA
<213> ORGANISM: Artificial Sequence
<220> FEATURE:
<223> OTHER INFORMATION: primer

<400> SEQUENCE: 169
cctgatcatc cacgaacata tcg                                          23

<210> SEQ ID NO 170
<211> LENGTH: 23
<212> TYPE: DNA
<213> ORGANISM: Artificial Sequence
<220> FEATURE:
<223> OTHER INFORMATION: primer

<400> SEQUENCE: 170
ggtggtgaat tgcatcgatt atg                                          23

<210> SEQ ID NO 171
<211> LENGTH: 23
<212> TYPE: DNA
<213> ORGANISM: Artificial Sequence
<220> FEATURE:
<223> OTHER INFORMATION: primer

<400> SEQUENCE: 171
cataatcgat gcaattcacc acc                                          23

<210> SEQ ID NO 172
<211> LENGTH: 25
<212> TYPE: DNA
<213> ORGANISM: Artificial Sequence
<220> FEATURE:
<223> OTHER INFORMATION: primer

<400> SEQUENCE: 172
gaagcaaaag gtcataaagt ggcgc                                        25

<210> SEQ ID NO 173
<211> LENGTH: 25
<212> TYPE: DNA
<213> ORGANISM: Artificial Sequence
<220> FEATURE:
<223> OTHER INFORMATION: primer

<400> SEQUENCE: 173
gcgccacttt atgacctttt gcttc                                        25

<210> SEQ ID NO 174
<211> LENGTH: 23
<212> TYPE: DNA
<213> ORGANISM: Artificial Sequence
<220> FEATURE:
<223> OTHER INFORMATION: primer

<400> SEQUENCE: 174
ggtcgaacgc aacccgataa gcg                          23

<210> SEQ ID NO 175
<211> LENGTH: 23
<212> TYPE: DNA
<213> ORGANISM: Artificial Sequence
<220> FEATURE:
<223> OTHER INFORMATION: primer

<400> SEQUENCE: 175
cgcttatcgg gttgcgttcg acc                          23

<210> SEQ ID NO 176
<211> LENGTH: 28
<212> TYPE: DNA
<213> ORGANISM: Artificial Sequence
<220> FEATURE:
<223> OTHER INFORMATION: primer

<400> SEQUENCE: 176
ccgacccgcg caaagtggat gatttaac                     28

<210> SEQ ID NO 177
<211> LENGTH: 28
<212> TYPE: DNA
<213> ORGANISM: Artificial Sequence
<220> FEATURE:
<223> OTHER INFORMATION: primer

<400> SEQUENCE: 177
gttaaatcat ccactttgcg cgggtcgg                     28

<210> SEQ ID NO 178
<211> LENGTH: 23
<212> TYPE: DNA
<213> ORGANISM: Artificial Sequence
<220> FEATURE:
<223> OTHER INFORMATION: primer

<400> SEQUENCE: 178
ctatacgctg cagaccacct tcg                          23

<210> SEQ ID NO 179
<211> LENGTH: 23
<212> TYPE: DNA
<213> ORGANISM: Artificial Sequence
<220> FEATURE:
<223> OTHER INFORMATION: primer

<400> SEQUENCE: 179
cgaaggtggt ctgcagcgta tag                          23

<210> SEQ ID NO 180
<211> LENGTH: 22
<212> TYPE: DNA
<213> ORGANISM: Artificial Sequence
<220> FEATURE:
<223> OTHER INFORMATION: primer

<400> SEQUENCE: 180
ccgggcgtag cgaacgttga ag                           22

<210> SEQ ID NO 181
<211> LENGTH: 22
<212> TYPE: DNA

```
<213> ORGANISM: Artificial Sequence
<220> FEATURE:
<223> OTHER INFORMATION: primer

<400> SEQUENCE: 181
cttcaacgtt cgctacgccc gg                                              22

<210> SEQ ID NO 182
<211> LENGTH: 22
<212> TYPE: DNA
<213> ORGANISM: Artificial Sequence
<220> FEATURE:
<223> OTHER INFORMATION: primer

<400> SEQUENCE: 182
gtaccgaacg aagaagggct gg                                              22

<210> SEQ ID NO 183
<211> LENGTH: 22
<212> TYPE: DNA
<213> ORGANISM: Artificial Sequence
<220> FEATURE:
<223> OTHER INFORMATION: primer

<400> SEQUENCE: 183
ccagcccttc ttcgttcggt ac                                              22

<210> SEQ ID NO 184
<211> LENGTH: 22
<212> TYPE: DNA
<213> ORGANISM: Artificial Sequence
<220> FEATURE:
<223> OTHER INFORMATION: primer

<400> SEQUENCE: 184
gtaccgaacg gcgaagggct gg                                              22

<210> SEQ ID NO 185
<211> LENGTH: 22
<212> TYPE: DNA
<213> ORGANISM: Artificial Sequence
<220> FEATURE:
<223> OTHER INFORMATION: primer

<400> SEQUENCE: 185
ccagcccttc gccgttcggt ac                                              22

<210> SEQ ID NO 186
<211> LENGTH: 22
<212> TYPE: DNA
<213> ORGANISM: Artificial Sequence
<220> FEATURE:
<223> OTHER INFORMATION: primer

<400> SEQUENCE: 186
gtaccgaacc tggaagggct gg                                              22

<210> SEQ ID NO 187
<211> LENGTH: 22
<212> TYPE: DNA
<213> ORGANISM: Artificial Sequence
<220> FEATURE:
<223> OTHER INFORMATION: primer

<400> SEQUENCE: 187
ccagcccttc caggttcggt ac                                              22
```

```
<210> SEQ ID NO 188
<211> LENGTH: 22
<212> TYPE: DNA
<213> ORGANISM: Artificial Sequence
<220> FEATURE:
<223> OTHER INFORMATION: primer

<400> SEQUENCE: 188
gtaccgaaca acgaagggct gg                                              22

<210> SEQ ID NO 189
<211> LENGTH: 21
<212> TYPE: DNA
<213> ORGANISM: Artificial Sequence
<220> FEATURE:
<223> OTHER INFORMATION: primer

<400> SEQUENCE: 189
cagcccttcg ttgttcggta c                                               21

<210> SEQ ID NO 190
<211> LENGTH: 22
<212> TYPE: DNA
<213> ORGANISM: Artificial Sequence
<220> FEATURE:
<223> OTHER INFORMATION: primer

<400> SEQUENCE: 190
gtaccgaacc aggaagggct gg                                              22

<210> SEQ ID NO 191
<211> LENGTH: 22
<212> TYPE: DNA
<213> ORGANISM: Artificial Sequence
<220> FEATURE:
<223> OTHER INFORMATION: primer

<400> SEQUENCE: 191
ccagcccttc ctggttcggt ac                                              22

<210> SEQ ID NO 192
<211> LENGTH: 22
<212> TYPE: DNA
<213> ORGANISM: Artificial Sequence
<220> FEATURE:
<223> OTHER INFORMATION: primer

<400> SEQUENCE: 192
gttgaagggg cggtgggcgg tg                                              22

<210> SEQ ID NO 193
<211> LENGTH: 22
<212> TYPE: DNA
<213> ORGANISM: Artificial Sequence
<220> FEATURE:
<223> OTHER INFORMATION: primer

<400> SEQUENCE: 193
caccgcccac cgccccttca ac                                              22

<210> SEQ ID NO 194
<211> LENGTH: 25
<212> TYPE: DNA
<213> ORGANISM: Artificial Sequence
<220> FEATURE:
```

```
<223> OTHER INFORMATION: primer

<400> SEQUENCE: 194
ggttgggccg aacggtgagt tgtac                                               25

<210> SEQ ID NO 195
<211> LENGTH: 25
<212> TYPE: DNA
<213> ORGANISM: Artificial Sequence
<220> FEATURE:
<223> OTHER INFORMATION: primer

<400> SEQUENCE: 195
gtacaactca ccgttcggcc caacc                                               25

<210> SEQ ID NO 196
<211> LENGTH: 23
<212> TYPE: DNA
<213> ORGANISM: Artificial Sequence
<220> FEATURE:
<223> OTHER INFORMATION: primer

<400> SEQUENCE: 196
gccgccgcgc atcctgcgcc gcc                                                 23

<210> SEQ ID NO 197
<211> LENGTH: 23
<212> TYPE: DNA
<213> ORGANISM: Artificial Sequence
<220> FEATURE:
<223> OTHER INFORMATION: primer

<400> SEQUENCE: 197
ggcggcgcag gatgcgcggc ggc                                                 23

<210> SEQ ID NO 198
<211> LENGTH: 26
<212> TYPE: DNA
<213> ORGANISM: Artificial Sequence
<220> FEATURE:
<223> OTHER INFORMATION: primer

<400> SEQUENCE: 198
gtaatcaaac ttgccattac tcagtg                                              26

<210> SEQ ID NO 199
<211> LENGTH: 26
<212> TYPE: DNA
<213> ORGANISM: Artificial Sequence
<220> FEATURE:
<223> OTHER INFORMATION: primer

<400> SEQUENCE: 199
cactgagtaa tggcaagttt gattac                                              26
```